US007029847B2

(12) United States Patent
Joung et al.

(10) Patent No.: US 7,029,847 B2
(45) Date of Patent: Apr. 18, 2006

(54) METHODS AND COMPOSITIONS FOR INTERACTION TRAP ASSAYS

(75) Inventors: J. Keith Joung, Winchester, MA (US); Jeffrey Miller, Cambridge, MA (US); Carl O. Pabo, Newton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 253 days.

(21) Appl. No.: 09/990,762

(22) Filed: Nov. 14, 2001

(65) Prior Publication Data
US 2002/0119498 A1 Aug. 29, 2002

Related U.S. Application Data

(63) Continuation-in-part of application No. 09/858,852, filed on May 16, 2001, now abandoned.

(60) Provisional application No. 60/204,509, filed on May 16, 2000.

(51) Int. Cl.
*C12Q 1/68* (2006.01)
*G01N 33/53* (2006.01)
*G01N 33/567* (2006.01)

(52) U.S. Cl. .............................. 435/6; 435/7.1; 435/7.2; 435/455; 435/DIG. 1; 435/DIG. 2; 435/DIG. 3

(58) Field of Classification Search .................... 435/6, 435/7.1, 455, DIG. 1, DIG. 2, DIG. 3
See application file for complete search history.

(56) References Cited

U.S. PATENT DOCUMENTS

| 5,580,736 | A | * | 12/1996 | Brent et al. ..................... 435/6 |
| 5,925,523 | A | | 7/1999 | Dove et al. |
| 6,326,150 | B1 | * | 12/2001 | Golemis et al. ............... 435/6 |
| 2002/0061512 | A1 | | 5/2002 | Kim et al. |
| 2003/0003449 | A1 | * | 1/2003 | Menzel et al. ................. 435/6 |

FOREIGN PATENT DOCUMENTS

| WO | WO 96/32503 A1 | 10/1996 |
| WO | WO 98/07845 A1 | 2/1998 |
| WO | WO 98/25947 A1 | 6/1998 |
| WO | WO 99/14319 | 3/1999 |
| WO | WO 99/28744 | 6/1999 |
| WO | WO 99/28745 | 6/1999 |
| WO | WO 99/31509 | 6/1999 |
| WO | WO 01/60970 | 8/2001 |

OTHER PUBLICATIONS

Komacker et al., Molecular Microbiology 30(3):615-624, 1998.*
Jappelli et al., Biochem. Biophys. Res. Commun. (1999) vol. 266, pp. 243-247.*
Allen et al., "Finding Prospective Partners in the Library: The Two-Hybrid System and Phage Display Find a Match," *Trends Biol. Sci* 20:511-516 (1995).
Brent et al., "A Eukaryotic Transcriptional Activator Bearing the DNA Specificity of a Prokaryotic Repressor," *Cell* 43:729-736 (1985).
Chien et al., "The Two-Hybrid System: A Method to Identify and Clone Genes for Proteins that Interact with a Protein of Interest," *PNAS* 88:9578-9582 (1991).
Durfee et al., "The Retinoblastoma Protein Associates With the Protein Phosphatase Type 1 Catalytic Subunit," *Genes & Development* 7:555-569 (1993).
Grossel et al., "A Yeast Two-Hybrid System for Discerning Differential Interactions Using Multiple Baits," *Nature Biotechnology* 17:1232-1233 (1999).
Gyuris et al., "Cdi1, a Human G1 and S Phase Protein Phosphatase That Associates with Cdk2," *Cell* 75:791-803 (1993).
Huang et al., " A Permutational Approach Toward Protein-DNA Recognition," *PNAS* 91:3969-3973 (1994).
Joung et al., "A Bacterial Two-Hybrid Selection System for Studying Protein-DNA and Protein-Protein Interactions," *Proc. Natl. Acad. Sci. U.S.A.* 97:7382-7387 (2000).
Joung et al., "Identifying and Modifying Protein-DNA and Protein-Protein Interactions Using a Bacterial Two-Hybrid Selection System," *J. Cell. Biochem. Suppl.* 37: pp. 53-57 (2001).
Keegan et al., "Separation of DNA Binding from the Transcription-Activating Function of Eukaryotic Regulatory Protein," *Science* 231:699-704 (1986).
Ma et al., "Converting a Eukaryotic Transcriptional Inhibitor into an Activator," *Cell* 55:443-446.
Phizicky et al., "Protein-Protein Interactions: Methods for Detection and Analysis," *Microbiol. Rev.* 59:94-123 (1995).
Rebar et al., "Phage Display Methods for Selecting Zinc Finger Proteins with Novel DNA-Binding Specificities," *Methods Enzymol.* 267:129-149 (1996).

(Continued)

*Primary Examiner*—Padmashri Ponnaluri
*Assistant Examiner*—Mark L. Shibuya
(74) *Attorney, Agent, or Firm*—Robins & Pasternak

(57) ABSTRACT

The present invention provides methods and compositions for interaction trap assays for detecting protein-protein, protein-DNA, or protein-RNA interactions. The methods and compositions of the invention may also be used to identify agents which may agonize or antagonize a protein-protein, protein-DNA, or protein-RNA interaction. In certain embodiments, the interaction trap system of the invention is useful for screening libraries with greater than $10^7$ members. In other embodiments, the interaction trap system of the invention is used in conjunction with flow cytometry. The invention further provides a means for simultaneously screening a target protein or nucleic acid sequence for the ability to interact with two or more test proteins or nucleic acids.

8 Claims, 18 Drawing Sheets

OTHER PUBLICATIONS

Sera and Schultz, "In Vivo Selection of Basic Region-Leucine Zipper Proteins with Altered DNA-Binding Specificities," *PNAS* 93:2920-2925 (1996).

Serebriiskii et al., "A Two-Hybrid Dual Bait System to Discriminate Specificity of Protein Interactions," *J. Biol Chem.* 274:17,080-17,087 (1999).

Smith et al., "Phage Display," *Chem. Rev.* 97:391-410 (1997).

Uetz et al., "A Comprehensive Analysis of Protein-Protein Interactions in *Saccharomyces Cerevisiae*," *Nature* 403:623-627 (2000).

Vojtek et al., "Mammalian Ras Interacts Directly With the Serine/Threonine Kinase Raf," *Cell* 74:205-214 (1993).

* cited by examiner

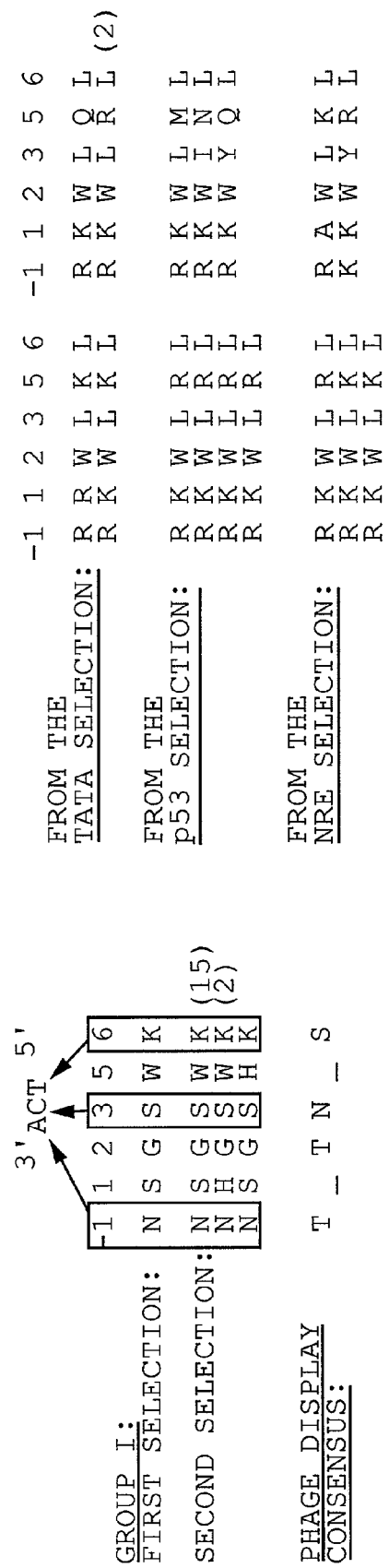

P53$^{ZF}$ *IN VITRO* SITE SELECTION CONSENSUS SEQUENCE:

CXGGA<u>CACGT</u>X (WHERE X = NO CLEAR PREFERENCE)

*IN VIVO* SITE SELECTION LIBRARY

CGGGA<u>NNNNN</u>G (WHERE N = A MIXTURE OF A, G, C, AND T)

SELECTED CLONES:

| SEQUENCE | # OF CLONES |
|---|---|
| CGGGA<u>CACGT</u>G | 9 |
| CGGGA<u>CATGT</u>G | 5 |
| CGGGA<u>CACGG</u>G | 2 |

| SEQUENCE | FOLD ACTIVATION |
|---|---|
| CGGGA<u>CACGT</u>G | 18.6 ± 2.7 |
| CGGGA<u>CATGT</u>G | 12.0 ± 0.5 |
| CGGGA<u>CACGG</u>G | 12.6 ± 1.9 |

FIG. 9

METHODS AND COMPOSITIONS FOR INTERACTION TRAP ASSAYS

RELATED APPLICATIONS

This application is a continuation-in-part of U.S. patent application Ser. No. 09/858,852, filed May 16, 2001 abandoned; which claimed the benefit of U.S. Provisional Patent Application Ser. No. 60/204,509, filed May 16, 2000; the specifications of both applications are hereby incorporated by reference.

BACKGROUND OF THE INVENTION

Specific protein-DNA and protein-protein interactions are fundamental to most cellular functions. Protein-DNA interactions, for example, form the basis of important mechanisms by which the cell activates or represses gene expression and regulates DNA replication. Polypeptide interactions are involved in, inter alia, formation of functional transcription complexes, repression of certain genes, signal transduction pathways, cytoskeletal organization (e.g., microtubule polymerization), polypeptide hormone receptor-ligand binding, organization of multi-subunit enzyme complexes, and the like.

Investigation of protein-DNA and protein-protein interactions under physiological conditions has been problematic. Considerable effort has been made to identify proteins that bind to proteins of interest. Typically, these interactions have been detected by using co-precipitation experiments in which an antibody to a known protein is mixed with a cell extract and used to precipitate the known protein and any proteins that are stably associated with it. This method has several disadvantages, such as: (1) it only detects proteins which are associated in cell extract conditions rather than under physiological, intracellular conditions, (2) it only detects proteins which bind to the known protein with sufficient strength and stability for efficient co-immunoprecipitation, (3) it may not be able to detect oligomers of the target, and (4) it fails to detect associated proteins which are displaced from the known protein upon antibody binding. Additionally, precipitation techniques at best provide a molecular weight as the main identifying characteristic. Similar difficulties exist in the analysis of physiologically relevant protein-DNA interactions. For these reasons and others, improved methods for identifying proteins that interact with a known protein have been developed.

One approach to these problems has been to use a so-called interaction trap system or "ITS" (also referred to as the "two-hybrid assay") to identify polypeptide sequences which bind to a predetermined polypeptide sequence present in a fusion protein (Fields and Song (1989) *Nature* 340:245). This approach identifies protein-protein interactions in vivo through reconstitution of a eukaryotic transcriptional activator. The system has also been adapted for studying protein-DNA interactions.

The interaction trap systems of the prior art are based on the finding that most eukaryotic transcription activators are modular. Brent and Ptashne showed that the activation domain of yeast GAL4, a yeast transcription factor, could be fused to the DNA binding domain of *E. coli* LexA to create a functional transcription activator in yeast (Brent et al. (1985) *Cell* 43:729–736). There is evidence that transcription can be activated through the use of two functional domains of a transcription factor: a domain that recognizes and binds to a specific site on the DNA and a domain that is necessary for activation. The transcriptional activation domain is thought to function by contacting other proteins involved in transcription. The DNA-binding domain appears to function to position the transcriptional activation domain on the target gene that is to be transcribed. These and similar experiments (Keegan et al. (1986) *Science* 231:699–704) formally define activation domains as portions of proteins that activate transcription when brought to DNA by DNA-binding domains. Moreover, it was discovered that the DNA binding domain does not have to be physically on the same polypeptide as the activation domain, so long as the two separate polypeptides interact with one another. (Ma et al. (1988) *Cell* 55:443–446).

Fields and his coworkers made the seminal suggestion that protein interactions could be detected if two potentially interacting proteins were expressed as chimeras. In their suggestion, they devised a method based on the properties of the yeast Gal4 protein, which consists of separable domains responsible for DNA-binding and transcriptional activation. Polynucleotides encoding two hybrid proteins, one consisting of the yeast Gal4 DNA-binding domain fused to a polypeptide sequence of a known protein and the other consisting of the Gal4 activation domain fused to a polypeptide sequence of a second protein, are constructed and introduced into a yeast host cell. Intermolecular binding between the two fusion proteins reconstitutes the Gal4 DNA-binding domain with the Gal4 activation domain, which leads to the transcriptional activation of a reporter gene (e.g., lacZ, HIS3) which is operably linked to a Gal4 binding site.

All yeast-based interaction trap systems in the art share common elements (Chien et al. (1991) *PNAS* 88:9578–82; Durfee et al. (1993) *Genes & Development* 7:555–69; Gyuris et al. (1993) *Cell* 75:791–803; and Vojtek et al. (1993) *Cell* 74:205–14). All use (1) a plasmid that directs the synthesis of a "bait": a known protein which is brought to DNA by being fused to a DNA binding domain, (2) one or more reporter genes ("reporters") with upstream binding sites for the bait fusion, and (3) a plasmid that directs the synthesis of proteins fused to activation domains and other useful moieties ("prey"). All current systems direct the synthesis of proteins that carry the activation domain at the amino terminus of the fusion, facilitating the expression of open reading frames encoded by, for example, cDNAs.

Due to an upper limit on the transformation efficiency of yeast cells of $\sim 10^6$, the yeast-based one-hybrid and two-hybrid systems are not practical for use in the analysis of libraries larger than $10^7$ in size. For the analysis of most cDNA libraries, the ability to cover libraries $10^6$ to $10^7$ in size is adequate. However, there are a number of situations in which the inability to search a library larger than $10^7$ in size is problematic. One example is the challenge of searching libraries containing randomized sequences. For example, a strategy for randomizing at just six different residues in a test polypeptide can produce a library of variants which exceeds the practical use of the yeast interaction trap systems. To illustrate, if one employs a strategy using 24 different codons (encoding 19 different amino acids) at each of the six positions, the resulting library will have a potential DNA sequence space of $24^6$ or $\sim 2 \times 10^8$ and an amino acid sequence space of $19^6$ or $\sim 5 \times 10^7$. To ensure nearly complete coverage of such a library, one needs to oversample by a factor of at least three-fold (i.e.—one must sample $3 \times 2 \times 10^8$ candidates). The difficulty with library size becomes exponentially more problematic with each additional residue that is randomized.

Another approach used to study protein-DNA and protein-protein interactions is the method of phage display. In this system, proteins are displayed on the surface of filamentous bacteriophage (e.g.—M13) that harbor the DNA encoding the displayed protein. Target proteins or DNA sequences of interest are immobilized on a solid support (typically plates or beads) and used to affinity-enrich libraries of phage-displayed proteins for candidates that bind to the target. Because these phage libraries are constructed in *E. coli*, this system can create libraries larger than $10^7$ (and as large as $10^{11}$) in size. This method has been used successfully to identify and characterize both protein-DNA and protein-protein interactions. See, for example, Allen et al. (1995) *Trends Biol. Sci.* 20: 511–516; Phizicky et al. (1995) *Microbiol. Rev.* 59:94–123; Rebar et al. (1996) *Mthds. Enzymol.* 267:129–149; and Smith et al. (1997) *Chem. Rev.* 97:391–410. However, phage display does have certain significant limitations. Unlike direct, single-step selection methods (e.g.—the yeast one—and two-hybrid systems), phage display is an enrichment process that requires multiple cycles to obtain desired candidates from a library. In addition, phage display enrichments are performed in vitro (and not in vivo as in yeast one- and two-hybrid methods). Finally, because proteins must be exported to the bacterial cell membrane in order to be displayed on the phage surface, certain proteins (particularly larger ones) are not well suited for analysis by phage display. This last limitation can be particularly significant if this biological phenomenon artifactually removes certain candidates from a library.

More recently, a prokaryote-based interaction trap assay has been developed. See, for example, U.S. Pat. No. 5,925,523. The prokaryotic ITS derives in part from the unexpected finding that the natural interaction between a transcriptional activator and subunit(s) of an RNA polymerase complex can be replaced by a heterologous protein-protein interaction which is capable of activating transcription. Because bacteria (*E. coli* in particular) have a much higher relative transformation efficiency (typically $10^9$ or greater) than yeast, the description of prokaryotic-based one- and two-hybrid systems would appear to address the library size restrictions of the yeast systems. However, although higher transformation efficiencies are possible in *E. coli*, a significant deficiency of the prior art is that it does not make clear which, if any, reporter gene(s) have the characteristics required for use in the analysis of libraries larger than $10^7$ in size. Desirable reporter genes should have one or more of the following characteristics: 1) The reporter gene should readily facilitate the rapid analysis of very large numbers of candidates. Thus, reporter genes (e.g.—the lacZ gene encoding beta-galactosidase) that must be screened by a visual colony phenotype (e.g.—color) are not useful because no more than $10^3$ to $10^4$ colonies can be screened on a single agar plate and it is not practical to manually plate and assess $10^3$ or more plates for each experiment. 2) The reporter gene system must be sufficiently stringent or selective so that spurious, randomly arising background mutations do not complicate the analysis. For example, a selection based on expression of the spectinomycin resistance gene (aadA) would not be suitable for the analysis of large libraries because randomly occurring mutations that result in spectinomycin resistance arise at a frequency of approximately $10^{-4}$ to $10^{-5}$ (Sera and Schultz, PNAS, 93: 2920–2925 (1996); Huang et al., PNAS, 91: 3969–3973 (1994)). Thus, if one were to examine a library of $10^8$ members using the aadA system, one should expect to receive $10^3$ or more false positives due solely to spontaneous spectinomycin resistance. This can pose a significant problem particularly if true positives occur with low frequency in the $10^8$ member library. 3) Expression of the reporter gene should be quantifiable and should easily facilitate the selection of candidates based on any specific criteria. For example, an ideal reporter system would allow one to isolate library members that meet specific quantitative cutoffs (e.g. expression of reporter >50 or <50) and/or windows (e.g. expression of reporter >25 AND <75, or <25 OR >75).

There are at least two additional deficiencies in the prior art describing the prokaryotic ITS:

A) The ability to simultaneously monitor the expression of multiple reporter genes in a single cell. U.S. Pat. Nos. 5,925,523 and 5,580,736 and others (PCT applications WO 99/14319; WO 99/28745; WO 99/31509 and WO 99/28744; and Grossle et al., Nature Biotechnology 17: 1232–1233 (1999) have noted the usefulness of having the interaction between the bait and prey constructs activate more than one reporter gene in a single cell to reduce the occurrence of false positives. Additionally, Grossle et al., Nature Biotechnology 17:1232–1233 (1999) and Serebriiskii et al., J. Biol Chem. 274: 17,080–17,087 (1999) demonstrate a "dual bait" version of the yeast two hybrid system capable of monitoring the interaction of two different bait proteins with a single prey protein. This system can be used to screen for cells which have a desired combination of interactions between a single prey protein and two bait proteins by utilizing a combination of growth selection screens and visual lacZ screens. However, in contrast to the present invention, those references do not teach or suggest simultaneous and independent monitoring of the expression of multiple reporter genes in a single cell where the expression of each reporter gene is regulated by the interaction of a single protein of interest with different partners. For example, one may wish to select a protein (from a large library) that interacts with Target Protein A but does NOT interact with Target Protein B. In this case, if the system was set up such that binding of the interactor protein with Target Protein A increased the expression of Reporter Gene A and the binding of the interactor protein with Target Protein A increased the expression of Reporter Gene B, we would want to select those cells that had very high expression of Reporter Gene A AND very low expression of Reporter Gene B. Selections of this type (based on the strengths of multiple interactions) would also be especially useful for selecting very specific DNA-binding proteins that bind well to the desired target site but do NOT bind well to even closely related sites. We note that U.S. Pat. No. 5,925,523 does not teach how one could easily monitor multiple reporters in a single cell and that, to our knowledge, no reference describes how to simultaneously monitor the differential expression of multiple reporters in a single cell.

B) Methods for practicing library vs library screening. With the wealth of genomic information currently becoming available, a number of groups have begun to address the challenges in library vs. library screening of large collections of coding sequences. Ideally, a method for performing such a comprehensive library vs. library search should: 1) provide an efficient method for crossing two large libraries and 2) be amenable to partial or complete automation. The use of transformation as a method to effect the simultaneous (or sequential) introduction of two libraries into either yeast or bacterial cells fails to meet either of these criteria. Even in bacteria where very high transformation efficiencies are possible, examination of $10^9$ combinations would only allow one to examine two libraries each comprised of only 33,000 candidates. In addition, since transformation requires pre-treatment of cells (e.g.—washing and resuspension in divalent cation solutions) and multiple protocol steps (e.g.—heat shock, addition of medium, recovery), it is not easily adaptable for automation. For library vs. library experiments conducted in yeast, investigators have exploited the fact that yeast can exist as one of two sexes (a and α) in haploid form. Mating of a and α cells leads to the formation of a diploid a/α cell harboring the DNA from both the starting haploid cells. Thus, a cells harboring a library of prey hybrids can be easily mated with α cells harboring a test bait hybrid(s) simply by mixing the cells together and selecting for diploid cells. In this way, a large number of combinations can be simply and rapidly tested, bypassing the need for labor-intensive transformation experiments when crossing the libraries. See Uetz et al. (2000) Nature 403:623–627 and Walhout et al. (2000) Science 287:116–122. Prokaryotes (and E. coli in particular) replicate asexually, and U.S. Pat. No. 5,925,523 and the existing literature do not teach how to perform analogous library mating experiments in the prokaryotic ITS.

It is an object of the present invention to describe the following improvements to the ITS: 1) reporter genes (and methods for detecting their expression) that readily permit the analysis of large libraries (>$10^7$ in size) and whose selectivity can be easily "tuned," modified, and/or monitored, 2) methods for the simultaneous and independent measurement of multiple interactions (as judged by expression of different reporter genes), and 3) construction of libraries using a phagemid-based system that provides a) an efficient, automatable method for performing library vs. library experiments and b) a method to simplify the analysis of positive candidates from ANY screen/selection performed in the prokaryotic ITS.

SUMMARY OF THE INVENTION

The present invention relates to methods and reagents for identifying, analyzing, modifying, and/or optimizing the affinity and/or specificity of protein-DNA and protein-protein interactions (collectively, "interacting pairs") in cell-based systems.

In certain aspects, the subject invention provides an interaction trap assay for selecting interacting pairs from large libraries of potential interactors, e.g., greater than $10^7$ in size (diversity) and more preferably greater than $10^8$, $10^9$, $10^{10}$, or $10^{11}$ in size. In one embodiment, we have discovered that the use of reporter genes which confer selective growth traits, rather than reporters which encode photometrically active labels or otherwise require visual inspection for detection, allows the use of libraries large enough to significantly improve the chance of finding interacting partners, i.e., from libraries in the range of $10^{7-10^{11}}$ members. In other embodiments, the use of flow cytometry for quantitating reporter gene expression permits the screening of large libraries, i.e., in the range of $10^7$ to $10^{11}$ members and allows one to simultaneously and independently assess in a single cell the affinity and/or specificity of any given interaction being tested. When designing or optimizing interactions, additional rounds of 1) mutatgenesis, and 2) selection or sorting can be used to further optimize interactions.

In certain preferred embodiments, the subject method is used to identify or optimize protein-DNA interactions. For example, the subject method can be used to identify mutant or composite DNA binding domains having desired sequence binding preferences. It can also be used to identify DNA sequences which are selectively bound by a given DNA binding protein and/or to determine the sequence specificity of a DNA binding protein. In some cases, the method may allow simultaneous variation of both 1) the target site and 2) the binding protein to find pairs that work well together.

For example, the method can be used to identify protein-DNA interactions by providing a host cell which contains a reporter gene encoding a growth selective marker, operably linked to a target DNA sequence. The cell is also engineered to include a first chimeric gene which encodes a first fusion protein including (a) a first interacting domain, and (b) a test DNA binding domain. The cell also expresses a second chimeric gene encoding a second fusion protein including (a) a second interacting domain that binds to the first interacting domain, and (b) an activation tag (such as a polymerase interaction domain) which activates transcription of the selective marker gene when localized in the vicinity of the target DNA sequence. One or both of the test DNA binding domains and/or the target DNA sequence are provided in the host cell populations as variegated libraries (with respect to sequence) to yield a library complexity of at least $10^7$ members. Cells in which interaction of a test DNA binding domain and a target DNA sequence occur can be selected and/or amplified based on the resulting favorable growth trait conferred by the growth selective marker.

For example, certain embodiments relate to a method for detecting an interaction between a first test polypeptide and a second test polypeptide. The method comprises a step of providing an interaction trap system including a host cell which contains one or more reporter genes operably linked to transcriptional regulatory sequences which include one or more binding sites ("DBD recognition element") for a DNA-binding domain. The reporter encodes a growth selection marker (defined infra). The cell is engineered to include a first chimeric gene which encodes a first fusion protein (the "bait" protein), the first fusion protein including a DNA-binding domain and first test polypeptide. The cell also includes a second chimeric gene which encodes a second fusion protein (the "prey" protein) including an activation tag (such as a polymerase interaction domain (PID) in the prokaryotic embodiments) which activates transcription of the reporter gene when localized to the vicinity of the DBD recognition element. Interaction of the first fusion protein and second fusion protein in the host cell results in a growth advantage which permits the isolation of cells including the interacting pair. Either or both of the first and second test polypeptides can be provided as part of a variegated library of coding sequences.

In other embodiments, the subject method can be used to detect the interactions between a potential DNA binding domain and a nucleic acid. The format described above for detecting protein-protein interactions can be readily modified as follows: the first and second test polypeptide portions of the bait and prey proteins are chosen from known interacting pairs, and one or both of the DNA binding domains and DBD recognition element(s) are provided as part of a variegated library of coding sequences or potential recognition sequences. Thus the system can be used to obtain: 1) DNA binding domains that recognize a desired target site; 2) functional binding sites for a given DNA-binding domain; or 3) sets of functionally interacting proteins and target sites. Alternatively, when analyzing protein-DNA interactions, the DNA binding domain can be fused directly to the activation tag, e.g., to consolidate the bait and prey protein functions of DNA interaction and transcriptional activation, into a single protein. In a preferred embodiment, the reporter gene is selected on the basis of its ability to provide a stringency to the detection/isolation step which reduces the occurrence rate of breakthrough false positives to less than $1:10^7$, and even more preferably less than $1:10^8$, $1:10^9$ or even $1:10^{10}$ Another aspect of the present invention provides methods and reagents for practicing various forms of interaction trap assays using flow cytometry, preferably as a high throughput means (supra), for detecting and isolating genes encoding interacting proteins or desired DNA binding domains. The subject "flow ITS" can be used, for example, to screen libraries of potential protein-protein or protein-nucleic acid interactions.

For example, certain embodiments relate to a method for detecting interaction between a first test polypeptide and a second test polypeptide. The method comprises a step of providing an interaction trap system including a host cell which contains one or more reporter genes operably linked to transcriptional regulatory sequences which include one or more binding sites ("DBD recognition element") for a DNA-binding domain. The reporter encodes a FACS tag polypeptide (defined infra). The cell is engineered to include a first chimeric gene which encodes a first fusion protein (the "bait" protein), the first fusion protein including a DNA-binding domain and first test polypeptide. The cell also includes a second chimeric gene which encodes a second fusion protein (the "prey" protein) including an activation tag (such as a polymerase interaction domain (PID) in the prokaryotic embodiments) which activates transcription of the reporter gene when localized to the vicinity of the DBD recognition element. Interaction of the first fusion protein and second fusion protein in the host cell results in measurably greater expression of the FACS tag polypeptide. Either or both of the first and second test polypeptides can be provided as part of a variegated library of coding sequences. Accordingly, the method also includes the steps of isolating cells expressing the FACS tag polypeptide by fluorescence activated cell sorting techniques.

In certain embodiments, the present invention provides a kit for detecting interaction between a first test polypeptide and a second test polypeptide, or between a DNA binding domain and a DBD recognition sequence.

In one version of this embodiment, the kit can include a first vector for encoding a first fusion protein ("bait fusion protein"), which vector comprises a first gene including (1) transcriptional and translational elements which direct expression in a host cell, (2) a DNA sequence that encodes a DNA-binding domain and which is functionally associated with the transcriptional and translational elements of the first gene, and (3) a means for inserting a DNA sequence encoding a first test polypeptide into the first vector in such a manner that the first test polypeptide is capable of being expressed in-frame as part of a bait fusion protein containing the DNA binding domain. The kit will also include a second vector for encoding a second fusion protein ("prey fusion protein"), which comprises a second gene including (1) transcriptional and translational elements which direct expression in a host cell, (2) a DNA sequence that encodes an activation tag, such as a polymerase interaction domain (PID), the activation tag DNA sequence being functionally associated with the transcriptional and translational elements of the second gene, and (3) a means for inserting a DNA sequence encoding the second test polypeptide into the second vector in such a manner that the second test polypeptide is capable of being expressed in-frame as part of a prey fusion protein containing the polymerase interaction domain. Additionally, the kit will include a prokaryotic host cell containing a reporter gene having a binding site ("DBD recognition element") for the DNA-binding domain, wherein the reporter gene expresses a FACS tag polypeptide or a growth selection marker (as defined herein) when a prey fusion protein interacts with a bait fusion protein bound to the DBD recognition element.

In another version, the kit can include a first vector for encoding the bait fusion protein, wherein the bait fusion gene includes (1) transcriptional and translational elements which direct expression in a host cell, (2) a DNA sequence that encodes a polypeptide (an "interacting domain") having a known interacting partner, and (3) a means for inserting a DNA sequence encoding a potential DNA-binding domain into the first vector in such a manner that the potential DNA-binding domain is expressed in-frame as part of a bait fusion protein containing the interacting domain. In certain embodiments, the kit will also include a second vector for encoding the prey fusion protein, which comprises a second gene including (1) transcriptional and translational elements which direct expression in a host cell, (2) a DNA sequence that encodes an activation tag, and (3) a coding sequence for a polypeptide which binds the interacting domain of the bait protein. However, in other embodiments (as when studying protein-DNA interactions), the interacting domain of the bait protein can be the activation tag, e.g., avoiding the need to generate the prey protein. Additionally, the kit will include a prokaryotic host cell containing one or more reporter genes having binding sites ("DBD recognition elements") for which binding or selectivity in binding by the potential DNA-binding domain of the bait protein is sought. The host cell population, in certain instances, can provide a library of reporter gene constructs wherein the DBD recognition element of a reporter gene is variegated to produce a library of potential recognition elements against which the bait protein binding is to be assessed. At least one of the reporter genes expresses a FACS tag polypeptide or a growth selection marker (as defined herein) when a prey fusion protein interacts with a bait fusion protein bound to the DBD recognition element.

In certain embodiments, the subject flow ITS can be carried out using a host engineered with two or more different reporter genes constructs encoding different FACS tag polypeptides which can be independently and simultaneously measured. In certain preferred embodiments, the transcriptional regulatory elements, and specifically the DBD recognition elements, of at least two of the reporter gene constructs are different. In such embodiments, DNA binding domains can be identified which selectively bind only a subset of the DBD recognition elements of the reporter gene constructs. The various reporter gene constructs can be provided on the same or separate vectors. The simultaneous expression of the various reporter genes (whether provided on the same or separate plasmids) provides a means for distinguishing actual interaction of the bait and prey proteins from, e.g., mutations or other spurious activation of the reporter gene, as well as to examine the specificity of interaction between the interacting pair. In certain embodiments in which the subject flow-ITS is being used to identify a DNA binding domain (as described in further detail below), multiple reporter gene constructs can be used in order to permit isolation of domains with selective binding activity. For example, the ITS host cell can include one or more reporter genes having transcriptional regulatory sequences for which a DNA binding domain is sought. At the same time, the cells can also include one or more reporter genes, encoding different FACS markers than above (see below), under the control of transcriptional regulatory sequences for which the DBD being sought does not bind to or activate expression. Thus, cells harboring desired candidates can be sorted on the basis of differential expression of the multiple classes of reporter genes. Differential protein-protein interactions could also be distinguished in this way if: 1) the DNA-binding domain of one fusion directs it to a particular promoter, and 2) the DNA-binding domain of the second fusion directs it to another promoter, but 3) these two proteins have different versions of the "interacting partner" and one wishes to 4) isolate proteins that recognize one interacting partner preferable to another. Similar methods could be used for cell-based selections in yeast cells and mammalian cells.

The interaction trap assays of the present invention can be used, inter alia, for identifying protein-protein and/or protein-DNA interactions, e.g., for generating protein linkage maps, for identifying therapeutic targets, and/or for general cloning strategies.

The ability to test very large libraries using one or more of the selection/screening methods described in this application permits not only the analysis of large scale library-versus-single bait or DNA target sequence experiments, but also large-scale library-versus-library experiments. Another aspect of the present invention describes a method for constructing protein-encoding libraries that can be introduced into bacterial cells without the need for transformation. Members of this library can then be "rescued" from bacterial cells without the need to perform labor-intensive plasmid extraction, then introduced into bacterial cells again without the need for transformation. This method is particularly useful for library vs. library screening/selection experiments, for directed or continuous evolution strategies, for serial selection protocols designed to reduce background false positives, and for automating the processing and re-testing of positive candidates from a screen/selection.

In still other embodiments, the ITS can be designed for the isolation of genes encoding proteins which physically interact with a protein/drug or DNA/drug complex. The method relies on detecting the reconstitution of a transcriptional activator in the presence of the drug, such as rapamycin, FK506 or cyclosporin. In the protein-protein format, if the bait and prey fusion proteins are able to interact in a drug-dependent manner, the interaction may be detected by reporter gene expression. In the DNA-protein format, if the bait and DBD recognition sequence of the reporter gene are able to interact in a drug-dependent manner, the interaction may be detected by reporter gene expression.

Yet another aspect of the present invention relates to the use of the subject ITS formats in the development of assays which can be used to screen for drugs which are either agonists or antagonists of a protein-protein or protein-DNA interaction of therapeutic consequence. In a general sense, the assay evaluates the ability of a compound to modulate binding between a bait protein and either a prey protein or a DBD recognition sequence, as the case may be. Exemplary compounds which can be screened include peptides, nucleic acids, carbohydrates, small organic molecules, and natural product extract libraries, such as isolated from animals, plants, fungus and/or microbes. The method may also be used to screen for compounds that regulate folding, processing, or activation of relevant proteins (e.g. by regulating phosphorylation, ubiquitination, proteolytic processing or other post-translational modification).

In many drug screening programs which test libraries of compounds and natural extracts, high throughput assays are desirable in order to maximize the number of compounds surveyed in a given period of time. The subject ITS-derived screening assays can be carried out in such a format, and accordingly may be used as a "primary" screen. Accordingly, in an exemplary screening assay of the present invention, an ITS is generated to include specific bait and prey pairs or bait and DBD recognition element pairs known to interact, and compound(s) of interest. Detection and quantification of reporter gene expression provides a means for determining a compound's efficacy at inhibiting (or potentiating) interaction between the interacting pairs. In certain embodiments, the approximate efficacy of the compound can be assessed by generating dose response curves from reporter gene expression data obtained using various concentrations of the test compound.

In order to make the cells permeable to certain small molecule compounds, it may be necessary alter the medium in which cells grow or to introduce mutations that affect the permeability of the cell membrane (see, for example, Vaara (1992) *Microbiol. Rev.* 56: 395–411; Sampson et al. (1989) *Genetics* 122: 491–501). For example, Vaara describes the use of various polycations and chelators for increasing the outer membrane permeability of gram negative bacteria. Sampson et al. describes the construction of an increased membrane permeability (imp) strain of *E. coli* which contains a mutation causing increased permeability of the outer membrane.

Particular aspects and embodiments of the invention are described in more detail below.

In a first aspect, the invention features a method for selecting a dimerizing test polypeptide, comprising:
i providing a population of host cells wherein each host cell contains
  (a) a chimeric gene which encodes a fusion protein, including one or more DNA-binding domains, an activation domain, and a test polypeptide,
  (b) a reporter gene operably linked to a transcriptional regulatory sequence which includes two or more binding sites (DBD recognition elements) for the DNA-binding domain of (a),
wherein binding of a single copy of the fusion protein to the transcriptional regulatory sequence of the reporter gene does not result in a desired level of expression of the reporter gene;
wherein dimerization and binding of the fusion protein to the transcriptional regulatory sequence of the reporter gene results in a desired level of expression of the reporter gene;
ii isolating host cells exhibiting a desired level of expression of the reporter gene thereby selecting a dimerizing test polypeptide.

In certain embodiments, the host cell further comprises a second reporter gene operably linked to a transcriptional regulatory sequence comprising one binding site for the DNA binding domain of (a).

In certain embodiments, the method may further comprising isolating a polynucleotide comprising a sequence encoding the dimerizing test polypeptide. In other embodiments, the method may further comprising linking the sequence encoding the dimerizing test polypeptide to a heterologous sequence.

In certain embodiments, the chimeric gene is a member of a library comprising a plurality of sequences encoding for random test polypeptides.

In another aspect, the invention features a method for selecting a composite transcription factor, comprising:
i providing a population of host cells wherein each host cell contains
  (a) a chimeric gene which encodes a fusion protein, including one or more DNA-binding domains, an activation domain, and a test polypeptide,
  (b) a gene which encodes for a DNA-binding domain of known specificity, (c) a reporter gene operably linked to a transcriptional regulatory sequence which includes at least one binding site (DBD recognition elements) for the DNA-binding domain of (a) and at least one binding site for the DNA-binding domain of (b), wherein binding of either of the DNA-binding domain of (a) or (b) to the transcriptional regulatory sequence of the reporter gene does not result in a desired level of expression of the reporter gene;

wherein formation of a dimer between (a) and (b) and binding of the dimer to the transcriptional regulatory sequence of the reporter gene results in a desired level of expression of the reporter gene; and ii isolating host cells exhibiting a desired level of expression of the reporter gene thereby selecting a composite transcription factor.

In certain embodiments, the host cell further comprises a second reporter gene operably linked to a transcriptional regulatory sequencing comprising one binding site for the DNA binding domain of (a).

In another aspect, the invention features a method for detecting an interaction between a test polypeptide and a DNA sequence, comprising:

i providing a population of host cells wherein each cell contains (a) a first reporter gene operably linked to a transcriptional regulatory sequence which includes one or more binding sites (DBD recognition elements) for a DNA-binding domain, (b) a second reporter gene operably linked to a transcriptional regulatory sequence which includes one or more binding sites (DBD recognition elements) for a DNA-binding domain, (c) a chimeric gene which encodes a fusion protein, the fusion protein including a test polypeptide, a weak DNA-binding domain and an activation tag, wherein binding of the weak DNA-binding domain of (c) to the binding sites of (a) or (b) does not cause a significant increase in the expression of the first reporter gene or the second reporter gene;

wherein expression of the first reporter gene results in a first detectable signal;

wherein expression of the second reporter gene results in a second detectable signal;

wherein a non-specific interaction between a test polypeptide of the fusion protein and a DBD recognition element of the first and second reporter genes results in an increased level of expression of the first and second reporter genes;

wherein a specific interaction between a test polypeptide of the fusion protein and a DBD recognition element of the first or second reporter gene results in a desired level of expression of either the first or second reporter gene; and ii isolating host cells comprising a fusion protein that specifically interacts with a DBD recognition element of the first or second reporter gene exhibiting a desired level of expression of the first or second reporter gene using FACS, thereby detecting an interaction between the test polypeptide and a DBD recognition element DNA sequence.

In certain embodiments, the chimeric gene is a member of a library comprising a plurality of sequences encoding for random test polypeptides or the DNA-binding domain recognition element of one of the reporter genes is a member of a library.

In other embodiments, the weak DNA-binding domain comprises two $Cys_2His_2$ (SEQ ID NO: 4) zinc fingers.

In various embodiments, the reporter gene encodes a gene product that gives rise to a detectable signal selected from the group consisting of color, fluorescence, luminescence, a cell surface tag, cell viability, relief of a cell nutritional requirement, cell growth and drug resistance.

In certain embodiments, expression of the reporter gene confers a growth advantage and the degree of the growth advantage is controllable by varying the growth conditions of the host cell. In first particular embodiment, the reporter gene is the yeast His3 gene and the degree of the growth advantage is controllable by exposing the host cell to varying concentrations of 3-aminotriazole. In a second particular embodiment, the reporter gene is a β-lactamase gene and the degree of the growth advantage is controllable by exposing the host cell to a β-lactam antibiotic or to a β-lactam antibiotic and a β-lactamase inhibitor. Examples of β-lactamase genes which may be used in accord with the invention include TEM-1, TEM-2, OXA-1, OXA-2, OXA-3, SHV-1, PSE-1, PSE-2, PSE-3, PSE-4 and CTX-1, and functional fragments thereof. Examples of β-lactam antibiotics which may be used in accord with the invention include penicillins, cephalosporins, monbactams and carbapenems. Examples of β-lactamase inhibitors which may be used in accord with the invention include Clavulanic acid, sulbactam, tazobactam, brobactam and β-lactamase inhibitory protein (BLIP). The β-lactam antibiotics and β-lactamase inhibitors are generally added to the growth medium of the host cells, however, in the case of BLIP, the inhibitory protein may be expressed within the cell in addition to being added to the growth medium.

In other embodiments, the reporter gene encodes a fluorescent protein. Examples of fluorescent proteins which may be used in accord with the invention include green fluorescent protein (GFP), enhanced green fluorescent protein (EGFP), Renilla Reniformis green fluorescent protein, GFP-mut2, GFPuv4, enhanced yellow fluorescent protein (EYFP), enhanced cyan fluorescent protein (ECFP), enhanced blue fluorescent protein (EBFP), citrine and red fluorescent protein from discosoma (dsRED).

In other embodiments, the reporter gene may encode a cell surface tag. In association with this embodiment, the method may further comprises the step of contacting the host cell with a fluorescently labeled antibody specific for the cell surface tag, thereby labeling the host cell, before isolation of host cells by FACS.

In various embodiments, the desired level of expression of at least one of the reporter genes is an increase, a decrease, or no change in the level of expression of the reporter gene as compared to the basal transcription level of the reporter gene. In a particular embodiment, the desired level of expression of one of the reporter genes is an increase in the level of expression of the reporter gene as compared to the basal transcription level of the reporter gene and the desired level of expression of the other reporter genes is no change in expression in any of the other reporter genes as compared to the basal transcription levels of the other reporter genes.

In various embodiments, the reporter genes encode unique detectable proteins which can be analyzed independently, simultaneously, or independently and simultaneously. In certain embodiments, at least one of the reporter genes encodes a fluorescent protein. In another embodiment, the expression level of at least one of the reporter genes may be analyzed by FACS.

In certain embodiments, the activation tag is an RNA polymerase, an RNA polymerase subunit, a functional fragment of an RNA polymerase, or a functional fragment of an RNA polymerase subunit. In other embodiments, the activation tag is a polypeptide, a nucleic acid, or a small molecule, and wherein the activation tag binds RNA polymerase, an RNA polymerase subunit, a functional fragment of an RNA polymerase, or a functional fragment of an RNA polymerase subunit. In still other embodiments, the activation tag interacts indirectly with RNA polymerase via at least one intermediary polypeptide, nucleic acid, or small molecule, which binds to the activation tag and to RNA polymerase. In a particular embodiment, the activation tag is a fragment of Gal 11P, and wherein the activation tag interacts with a fusion between Gal4 and the α subunit of RNA polymerase.

In other embodiments, the expression level of the fusion protein can be controlled by varying the growth conditions of the host cell. For example, in a particular embodiment, the expression level of the fusion protein can be controlled by varying the concentration of IPTG or anhydrotetracycline to which the host cell is exposed. In another embodiment, the fusion protein is expressed from a promoter comprising a binding site for the lac repressor or the tet repressor.

In other embodiments, the host cell may be a eukaryotic cell or a prokaryotic cell. Exemplary eukaryotic cells include yeast and mammalian cells. Exemplary prokaryotic cells include *Escherichia, Bacillus, Streptomyces, Pseudomonas, Salmonella, Serratia, Streptococcus, Lactobacillus, Enterococcus* and *shigella*.

In another embodiment, the reporter gene construct and/or the chimeric gene constructs may contained within a vector for introduction into the host cell. In particular embodiments, the vector may be a plasmid or a phagemid. Phagemid vectors are generally used in conjuction with a host cell that expresses a functional F pilus. Particular examples of phagemids which may be used in accord with the invention include pBluescriptIISK+ or pBR-GP-Z12BbsI, or derivatives or precursors thereof. When a phagemid vector is being utilized, the phagemid may be introduced into the host cell by infection of the host cell with infectious phage containing the phagemid vector in combination with a helper filamentous phage. Examples of helper filamentous phage which may be used in accord with the invention include M13K07, VCS-M13, M13, and f1, and derivatives thereof.

In certain embodiments, the method further comprises the step of identifying nucleic acids which encode fusion proteins resulting in a desired level of expression of the desired reporter genes.

In various embodiments, the DBD recognition element is a member of a library of at least $10^7$, $10^8$, $10^9$, $10^{10}$, $10^{11}$, or $10^{12}$ potential binding sites for a DNA binding domain, wherein host cells comprising a DBD recognition element bound by a test polypeptide are isolated. Alternatively, the DBD recognition element is a desired binding site for a DNA binding domain and the test polypeptide is a member of a library of at least $10^7$, $10^8$, $10^9$, $10^{10}$, $10^{11}$, or $10^{12}$ polypeptides, wherein host cells comprising a polypeptide which binds to the DBD recognition element are isolated. In a further embodiment, the DBD recognition element is a member of library of potential binding sites for a DNA binding domain and the test polypeptide is a member of a library of polypeptides, wherein host cells comprising a polypeptide that binds a DBD recognition element are isolated.

In certain embodiments, the polypeptides are zinc finger proteins. In other embodiments, binding sites for a DNA binding domain bind a zinc finger protein. The methods of the invention may be used to find DNA sequences which bind to a known or novel zinc finger protein. Alternatively, the methods of the invention may be used to isolate known or novel polypeptides which bind to a test DNA sequence.

In various embodiments, the fusion protein is assayed for the ability to interact with at least two, three, four or five different DNA sequences each operably linked to reporter genes. In certain embodiments, the reporter genes are operably linked to the same transcriptional regulatory sequence. Alternatively, the reporter genes are operably linked to separate copies of the same transcriptional regulatory sequence. Further, the reporter genes may be operably linked to different transcriptional regulatory sequences.

Other features and advantages of the invention will be apparent from the following detailed description, and from the claims. The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, *Molecular Cloning A Laboratory Manual*, 2nd Ed., ed. by Sambrook, Fritsch and Maniatis (Cold Spring Harbor Laboratory Press: 1989); *DNA Cloning*, Volumes I and II (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I–IV (D. M. Weir and C. C. Blackwell, eds., 1986); *Manipulating the Mouse Embryo*, (Cold Spring Harbor Laboratory Press, Cold Spring Harbor, N.Y., 1986).

BRIEF DESCRIPTION OF THE FIGURES

FIG. 9. This figure shows the results of a certain embodiment of the subject interaction trap assay wherein a DNA-sequence can be selected which interacts with a specific protein. (SEQ ID NOS 15–22, respectively, in order of appearance).

DETAILED DESCRIPTION OF THE INVENTION

Figure 1A:
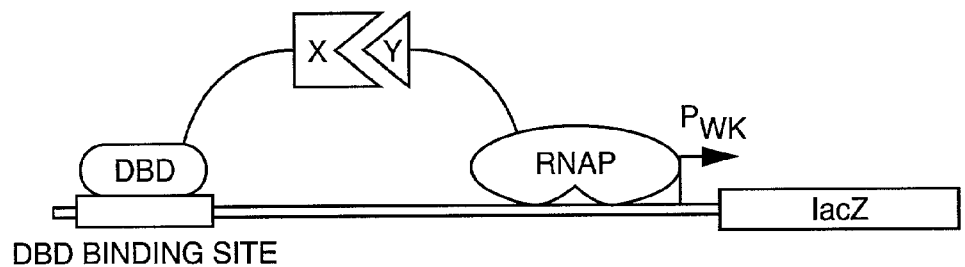
FIG. 1. (A) Transcriptional activation in a previously described *E. coli*-based genetic screen—developed by Hochschild and colleagues (refs 8,10)—for studying protein-DNA and protein-protein interactions. (B) Modified reporter template for our *E. coli*-based genetic selection system. (C) Model for transcriptional activation of the $P_{zif}$ promoter by fusion proteins Gal11P-Zif123 and αGal4. ZF1, ZF2, and ZF3 are the three zinc fingers of the Zif268 protein.

In order to address certain of the above-described deficiencies in the art, the inventors herein disclose various embodiments of the ITS which permit the use of interaction trap assays capable of analyzing libraries exceeding the current limitation of $10^7$ candidate sequences by several orders of magnitude. Certain versions of the subject assays are designed for detecting DNA-protein interactions (including tests of their specificity), while other embodiments are designed for detecting protein-protein interactions. Similar methods could be used to screen for drugs that facilitate or interfere with such interactions. One feature of the subject assay which facilitates the search of large libraries is that it permits a more exhaustive search of the sequence space for transcriptional regulatory sequences and useful naturally occurring and/or synthetic polypeptides. In addition, methods that permit the simultaneous and independent measurement of multiple reporters and the isolation of cells with desired reporter gene expression "profiles" are described (such methods can be in applied, in principle, to either prokaryotic or eukaryotic [e.g.—yeast or mammalian] cells). Finally, methods for constructing libraries of plasmids that can be introduce and "rescued" from cells without the need for transformation or plasmid isolation are described. This aspect of the subject invention also provides a means for producing combinations of interacting pairs that exceed current limits of cell transformation efficiency.

The goal of all of the methods described in this application is to identify, modify, or optimize proteins, small molecules (drugs), or nucleic acid sequences with affinities and specificities for their target interaction partner(s) that permit them to function effectively in vivo. We note that the output of one or more of the methods disclosed here may be one or more candidates (that is, a pool or enriched library of candidates) that have potentially desirable characteristics for use in in vivo contexts. Pools of candidates may also require additional testing in mammalian cells or other functional assays to determine which candidate(s) will be most useful in vivo.

I. Overview

A. High Throughput Analysis of Large Libraries.

The present invention provides several embodiments of detection techniques which facilitate the screening of large libraries of sequences, e.g., greater than $10^7$ different sequences, and more preferably greater than $10^8$, $10^9$, $10^{10}$, or $10^{11}$ different sequences.

One of those embodiments, the use of flow cytometry with (optionally) multiple FACS-active reporters, is discussed further in Section I(B) below.

In another embodiment of the subject assay, the reporter gene encodes a gene product which confers a growth advantage (which is "tunable" in the preferred embodiment) to a prokaryotic host cell, rather than merely a visual screening marker. By "tunable", it is meant that the activity of the reporter gene product, and therefore the stringency of the ITS, can be adjusted, such as by use of a competitive inhibitor of the reporter gene product. To further illustrate this strategy, we have discovered that, surprisingly, the HIS3 reporter gene, along with the use of 3AT, can be used to rescue a prokaryotic host cell in HIS selective media with sufficient stringency to be able to successfully isolate interacting pairs from a large library of variants. Lack of stringency in other systems can result in isolation of a significant population of background or breakthrough false positives, as described in the Background section above. In large libraries, a high percentage of false positives can make the isolation and identification of true interactors time consuming, if not impossible. In the case of the HIS3 reporter, the use of 3AT (a competitive inhibitor of HIS3) can facilitate the selection of cells in which the HIS3 reporter is highly expressed, and thereby lower the number of weak interactions/false positives in the enriched product.

Thus, the subject assay can be set up to utilize a reporter gene system that reduces the number of false positive interactions to less than 50% of an enriched library, and more preferably less than 25 percent, or even 10, 5 or 1 percent. In a preferred embodiment, the assay reduces the occurrence rate of breakthrough false positives to less than $1:10^7$, and even more preferably less than $1:10^8$, $1:10^9$ or even $1:10^{10}$.

B. Flow-ITS Embodiments

The flow-ITS technique of the present invention provides an interaction trap system having a detection step in which expression of the reporter gene permits selection of cells by flow cytometry. In preferred embodiments, the assay also includes a preselection step in which the population of cells subjected to FACS analysis is pre-enriched for interactors. The subject assay relies on the use of reporter genes which express gene products that are (i) localized to the cell surface (a cell surface protein) and include an extracellular domain which can be tagged with an antibody or other binding moiety, or (ii) fluorescently active, or both.

The first, though optional, step of the flow-ITS is a "pre-flow enrichment" step that permits throughput of extremely large numbers of cells from the interaction trap (the "ITS cells"). In this step, ITS cells that express a particular reporter cell surface protein are identified and isolated in an affinity separation step. To accomplish this, the ITS cells include a reporter gene which encodes a cell surface protein (referred to herein as a "surface FACS tag" protein). Upon development of the interaction trap, e.g., after sufficient time has elapsed such that expression of the reporter gene will have occurred in cells in which the bait and prey proteins interact, the ITS cells are applied to a matrix which can be sequestered and which includes a moiety that interacts with the surface FACS tag protein. In this manner, ITS cells expressing the surface FACS tag can be sequestered on the matrix and thereby separated from ITS cells which do not express at least a certain threshold level of the surface FACS tag. As described in further detail below, this pre-enrichment step permits the screening of initial ITS cell populations exceeding $10^{13}$ cells per day using conventional columns.

In other embodiments, a pre-flow enrichment step can be used wherein the host cell also includes a reporter gene construct encoding a growth selection marker, such as the HIS3 gene construct described above, which permits enrichment of the cell population by growth selection prior to the cytometric sorting step. In one embodiment, the reporter gene is a multicistronic reporter, e.g., the coding sequence for the FACS tag and growth selection marker being under the control of the same transcriptional regulatory sequence(s) and arranged such that a single mRNA transcript includes both coding sequence. In such embodiments, it may be necessary to include other elements well known in the art, such as internal ribosome entry sequences (IRES) and the like in order to obtain a suitable level of translation of the additional coding sequences found in the transcript.

The second step of the subject flow-ITS involves the use of fluorescence activated cell sorting (FACS) techniques. In this step, ITS cells expressing a reporter gene encoding a surface FACS tag or a fluorescently active polypeptide (whether localized to the cytoplasm or cell surface), can be detected and thus can be isolated by flow cytometry. As described in further detail below, state-of-the-art FACS techniques can sort cells at rates up to 70,000 cells/sec in "purity sort mode" (wherein the resultant sorted population of cells is relatively pure), and at rates of greater than 100,000 cells/sec in "enrich mode" (wherein the resultant sorted population of cells is less pure) (www.cytomation.com/noncomm/products/prod_cyto_mls.html). Thus, with currently available FACS technology, greater than $6 \times 10^9$ cells can be sorted per day.

In addition, modern FACS equipment can simultaneously sort based on fluorescence at different wavelengths, e.g., can detect the expression of two or more different reporter genes and gate cells for isolation accordingly.

In particular embodiments, it may be desirable to provide two or more reporter gene constructs which are chosen because of a desire to determine if their expression is regulated by interaction of the bait and prey proteins and transcriptional regulatory elements of each reporter. The reporter genes can both encode direct FACS tags, indirect FACS tags, or a combination thereof. One or more of the reporter genes can encode a polypeptide which can be used in the pre-flow enrichment step described below.

The simultaneous expression of the various reporter genes (whether provided on the same or separate plasmids) provides a means for distinguishing actual interaction of the bait and prey proteins and transcriptional regulatory elements from, e.g., mutations or other spurious activation of the reporter gene and also provides a means for selecting proteins with the desired specificity. In one embodiment of a multiple reporter assay, the subject flow-ITS can be used to identify a DNA binding domain (as described in further detail below). For instance, multiple reporter gene constructs can be used in order to permit isolation of domains with selective binding activity. For example, the ITS host cell can include one or more reporter genes having transcriptional regulatory sequences for which a DNA binding domain is sought. At the same time, the cells can also include one or more reporter genes, encoding different FACS markers than above, under the control of transcriptional regulatory sequences for which it is desired that the DBD being sought does not bind to or activate expression from. Thus, cells can be sorted on the basis of differential expression of the reporter genes. Extensions of this method could be developed to analyze the specificity of protein-protein interactions (see example in Background above).

The prokaryotic interaction trap systems described herein provide advantages over the conventional eukaryotic ITS. For example, the transformation frequency of prokaryotic cells permits the creation of host cells harboring libraries larger than $10^7$. The use of bacterial host cells to generate an interaction trap system also provides a system which is generally easier to manipulate genetically relative to the eukaryotic systems. Furthermore, bacterial host cells are easier to propagate. The shorter doubling times for bacteria will often provide for development of a FACS-detectable signal in the ITS in a shorter time period than would be obtained with a eukaryotic ITS.

Yet another benefit which may be realized by the use of the prokaryotic ITS is lower spurious activation relative to, e.g., the ITS fusion proteins employed in yeast. In eukaryotic cells, spurious transcription activation by a bait polypeptide having a high acidic residue content can be problematic. This is not expected to an impediment for the use of such bait polypeptides in the prokaryotic ITS.

Another benefit in the use of the prokaryotic ITS is that, in contrast to the eukaryotic systems, nuclear localization of the bait and prey polypeptides is not a concern in bacterial cells.

Still another advantage of the use of the prokaryotic ITS can be realized where the bait and/or prey polypeptides are derived from eukaryotic sources, such as human. One problem which can occur when using the yeast-based ITS of the prior art is that mammalian/eukaryotic derived bait or prey may retain sufficient biological activity in yeast cells so as to confound the results of the ITS. The greater evolutionary divergence between mammals and bacteria reduces the likelihood of a similar problem in the prokaryotic ITS of the present invention.

C. Directed Evolution

Moreover, the subject method can be used for directed evolution involving protein-protein interactions, protein-DNA interactions, protein-drug interactions, or drug-DNA interactions. For instance, identified interacting pairs can be improved by additional rounds of mutagenesis, selection, and amplification, e.g., diversity can be introduced into one or both of the identified interacting pair, and the resulting library screened according to the present invention. The goal may be, for instance, to use such a process to optimize the binding characteristics, e.g., for tighter binders and/or better selectivity in binding. Diversity can be introduced by most any standard mutagenesis technique, such as by irradiation, chemical treatment, low fidelity replication, use of randomized PCR primters, etc (see below). Moreover, the ability to selectively control (tune) the stringency of the isolation/detection step (and therefore provide the user with the ability to set specific cutoffs of windows) in the subject assay format or to use multiple FACS tags and thus directly test for specificity can be extremely beneficial for directed evolution approaches.

D. Selecting DNA-protein Interactions

In addition to protein-protein interactions, the various ITS embodiments described herein can be used to identify protein-DNA interactions. DNA-binding proteins, such as transcription factors, are critical regulators of gene expression. For example, transcriptional regulatory proteins are known to play a key role in cellular signal transduction pathways which convert extracellular signals into altered gene expression (Curran and Franza, (1988) Cell 55:395–397). DNA-binding proteins also play critical roles in the control of cell growth and in the expression of viral and bacterial genes. A large number of biological and clinical protocols, including among others, gene therapy, production of biological materials, and biological research, depend on the ability to elicit specific and high-level expression of genes encoding RNAs or proteins of therapeutic, commercial, or experimental value. Such gene expression is very often dependent on protein-DNA interactions.

E. Construction of Phagemid-Based Libraries

Another aspect of the present invention describes a method for constructing protein-encoding libraries that (once constructed using standard transformation procedures) can be introduced into bacterial cells without the need for additional transformation. Members of this library can then be "rescued" from bacterial cells without the need to perform labor-intensive plasmid extraction and introduced into bacterial cells again without the need for transformation. This method is particularly useful for library vs. library screening/selection experiments, for directed or continuous evolution strategies, for serial selection protocols designed to reduce background false positives, and for automating the processing and re-testing of positive candidates from a screen/selection.

One embodiment of this aspect of the invention is to construct protein-encoding libraries on phagemid vectors. Phagemid vectors (e.g.—pBluescriptIISK+ or pBR-GP-Z12BbsI [from Example 1 below]) harbor two origins of replication: one (e.g.—ColEI origin) permits replication as a standard multicopy, double-stranded plasmid and the second (e.g.—F1 origin) permits replication as a single-stranded filamentous phage genome IF phage-encoded proteins are also expressed in the cell. Infection of cells harboring the double-stranded phagemid with a filamentous helper phage (attenuated in its ability to replicate by mutations in its own origin of replication) results in the production of infectious phage particles containing single-stranded versions of the phagemid. Even if multiple plasmids are present in the cell (as is the case for most ITS experiments), the phagemid can be selectively rescued as phage using this system. These phage particles can be used to "infect" new bacterial cells resulting in the introduction of the single-stranded phagemid which then replicates as a standard double-stranded plasmid. (Note that cells can only be infected if they express an F pilus.) Thus, this methodology permits the rescue of phagemids from cells by infection with a helper phage and their subsequent introduction into fresh cells by simple infection.

This phagemid-based technology can be used to facilitate large library vs. library experiments. For example, one could create a library of $10^6$ or more prey proteins by introducing them into E. coli using standard transformation methods and then "rescuing" the library as phage by infecting the transformed cells with a helper phage. One could also create a library of $10^6$ or more bait proteins by introducing them into an E. coli strain harboring a measurable reporter gene by standard transformation techniques. To cross the libraries one would simply infect the bait library of cells with the prey library of phage (using an excess of cells over phage to ensure that each cell is on average only infected by one phage) and look for activated expression of the reporter gene. Since one is not limited by transformation efficiencies, in theory one should be able to use enough cells and phage to ensure coverage of nearly all possible $\sim 10^{12}$ or more pairwise combinations.

The phagemid-based method is also useful for experiments requiring serial selection/screening (e.g.—for directed evolution approaches). For example, one could create a library as phage, infect a reporter strain of interest, perform the selection/screen, and then rescue positives again as phage. This enriched pool of phage could then be mutagenized (e.g.—by infection of and replication in a mutator strain) and then reintroduced into a reporter strain for the next round of selection/screening. This process could be continued for many cycles to obtain the desired candidates.

In addition, phagemid rescue can be used to enrich a library when true positives are rare relative to the background breakthrough rate of a particular selection/screen (that is, spontaneously occurring false positives). As described in greater detail in Example 1 below (see NRE selection results), rescue of phagemids from an intial selection followed by reintroduction and reselection in fresh reporter strain cells can enrich for true positives relative to false positives whose phenotype is not linked to the presence of the phagemid.

The ability to easily rescue and reintroduce library phagemids also facilitates the analysis of potential interactors obtained from selections or screens in several ways: 1) Phagemid-linkage testing. An important test of whether a phagemid-encoded library candidate is a true positive is whether altered expression of the reporter gene is linked with the phagemid (that is, does the phagemid when isolated and reintroduced into the reporter strain still activate expression of the reporter?). Linkage testing is greatly facilitated when performed by the phagemid-based system. Infection of phagemid-containing cells with helper phage results in the selective "rescue" of only the phagemid and not other plasmids typically present in the ITS reporter strain. This rescue by phage infection is much faster than alternative protocols involving plasmid isolation followed by retransformation into an intermediate bacterial strain to separate the plasmid encoding the library candidate from other plasmids in the cell. 2) Tests of interaction specificity. Rescued phagemids can also be easily introduced into a number of reporter strains expressing different interaction targets to test their specificity of interaction. Simple infection of these reporter strains by phage is much easier than alternative methods involving transformation (which would require making all reporter strains competent and then performing multiple transformations). 3) Preparation of DNA for sequencing. Phage (harboring candidate phagemids) can also be used to infect standard cloning strains (e.g.—XL1-Blue) to prepare clonal DNA for sequencing. Again, no transformation is necessary to effect transfer of the phagemid to a strain suitable for preparing plasmid DNA. Example 1 below illustrates the use of phagemid rescue to facilitate phagemid-linkage testing, tests of interaction specificity, and preparation of DNA for sequencing.

II. Definitions

Before further description of the invention, certain terms employed in the specification, examples and appended claims are, for convenience, collected here.

The term "prokaryote" is art recognized and refers to a unicellular organism lacking a true nucleus and nuclear membrane, having genetic material composed of a single loop of naked double-stranded DNA. Prokaryotes with the exception of mycoplasmas have a rigid cell wall. In some systems of classification, a division of the kingdom Prokaryotae, Bacteria include all prokaryotic organisms that are not blue-green algae (Cyanophyceae). In other systems, prokaryotic organisms without a true cell wall are considered to be unrelated to the Bacteria and are placed in a separate class—the Mollicutes.

The term "bacteria" is art recognized and refers to certain single-celled microorganisms of about 1 micrometer in diameter; most species have a rigid cell wall. They differ from other organisms (eukaryotes) in lacking a nucleus and membrane-bound organelles and also in much of their biochemistry.

The term "eukaryote" is an art recognized term which refers to an organism whose cells have a distinct nucleus, multiple chromosomes, and a mitotic cycle. Eukaryotic cells include cell from animals, plants, and fungi, but not bacteria or algae.

As used herein, "recombinant cells" include any cells that have been modified by the introduction of heterologous DNA.

As used herein, the terms "heterologous DNA" or "heterologous nucleic acid" is meant to include a nucleic acid that comprises two or more subsequences that are not found in the same relationship to each other in nature. For instance, a nucleic acid that is recombinantly produced typically has two or more sequences from unrelated genes synthetically arranged to make a new functional nucleic acid, e.g., a promoter from one source and a coding region from another source or a fusion of coding sequences from two different genes. The two nucleic acids are thus heterologous to each other in this context. When added to a cell, the recombinant nucleic acids would also be heterologous to the endogenous genes of the cell. Thus, in a cell, a heterologous nucleic acid would include a nucleic acid that does not occur naturally as part of the genome in which it is present, or nucleic acid which is found in a location or locations in the genome that differs from that in which it occurs in nature, or occurs extra-chromasomally, e.g., as part of a plasmid.

By "protein" or "polypeptide" is meant a sequence of amino acids of any length, constituting all or a part of a naturally-occurring polypeptide or peptide, or constituting a non-naturally-occurring polypeptide or peptide (e.g., a randomly generated peptide sequence or one of an intentionally designed collection of peptide sequences).

The terms "chimeric", "fusion" and "composite" are used to denote a protein, peptide domain or nucleotide sequence or molecule containing at least two component portions which are mutually heterologous in the sense that they are not, otherwise, found directly (covalently) linked in nature. More specifically, the component portions are not found in the same continuous polypeptide or gene in nature, at least not in the same order or orientation or with the same spacing present in the chimeric protein or composite domain. Such materials contain components derived from at least two different proteins or genes or from at least two non-adjacent portions of the same protein or gene. Composite proteins, and DNA sequences which encode them, are recombinant in the sense that they contain at least two constituent portions which are not otherwise found directly linked (covalently) together in nature.

By a "DNA binding domain" or "DBD" is meant a polypeptide sequence which is capable of directing specific polypeptide binding to a particular DNA sequence (i.e., to a DBD recognition element). The term "domain" in this context is not intended to be limited to a single discrete folding domain. Rather, consideration of a polypeptide as a DBD for use in the bait fusion protein can be made simply by the observation that the polypeptide has a specific DNA binding activity. DNA binding domains, like activation tags, can be derived from proteins ranging from naturally occurring proteins to completely artificial sequences.

The term "activation tag" refers to a molecule capable of affecting transcriptional activation on its own or by assembling, or recruiting, an active polymerase complex. In various embodiments, the activation tag may be a polypeptide, a nucleic acid or a small moleucle. In certain embodiments, the activation tag is an RNA polymerase, an RNA polymerase subunit, a functional fragment of an RNA polymerase, or a functional fragment of an RNA polymerase subunit. In other embodiments, the activation tag is a polypeptide, nucleic acid or small moleucle, that can directly interact with RNA polymerase, an RNA polymerase subunit, a functional fragment of an RNA polymerase, a functional fragment of an RNA polymerase subunit, a molecule covalently fused to RNA polymerase, a molecule covalently fused to an RNA polymerase subunit, a molecule covalently fused to a functional fragment of RNA polymerase, or a molecule covalently fused to a functional fragment of an RNA polymerase subunit. In still other embodiments, the activation tag is a molecule (polypeptide, nucleic acid, or small molecule) which interacts indirectly with RNA polymerase, an RNA polymerase subunit, a functional fragment of an RNA polymerase, or a functional fragment of an RNA polymerase subunit, via at least one intermediary molecule (polypeptide, nucleic acid, or small molecule), wherein the intermediary molecule can functionally link the activation tag to RNA polymerase, an RNA polymerase subunit, a functional fragment of an RNA polymerase, or a functional fragment of an RNA polymerase subunit. Activation tags can be known sequences or molecules or can be derived from random libraries or polypeptide, nucleic acids, small molecules.

The terms "recombinant protein", "heterologous protein" and "exogenous protein" are used interchangeably throughout the specification and refer to a polypeptide which is produced by recombinant DNA techniques, wherein generally, DNA encoding the polypeptide is inserted into a suitable expression vector which is in turn used to transform a host cell to produce the heterologous protein. That is, the polypeptide is expressed from a heterologous nucleic acid.

As used herein, a "reporter gene construct" is a nucleic acid that includes a "reporter gene" operatively linked to transcriptional regulatory sequences. Transcription of the reporter gene is controlled by these sequences. The activity of at least one or more of these control sequences is directly or indirectly regulated by a transcriptional complex recruited by virtue of interaction of the DBD with its binding site and between the bait and prey fusion proteins. The transcriptional regulatory sequences can include a promoter and other regulatory regions that modulate the activity of the promoter, or regulatory sequences that modulate the activity or efficiency of the RNA polymerase that recognizes the promoter. Such sequences are herein collectively referred to as transcriptional regulatory elements or sequences. The reporter gene construct will also include a "DBD recognition element" which is a nucleotide sequence that is specifically bound by the DNA binding domain of the bait fusion protein. The DBD recognition element is located sufficiently proximal to the promoter sequence of the reporter gene so as to cause increased reporter gene expression upon recruitment of an RNA polymerase complex by a bait fusion protein bound at the recognition element.

As used herein, a "reporter gene" is a gene whose expression may be detected. For example, in the case of the subject flow-ITS, expression of the reporter may be detected by, e.g., flow cytometry and/or affinity chromatography; reporter genes may encode any protein or nucleic acid that provides a cell surface marker, e.g., a surface antigen for which specific antibodies/ligands are available, or a protein or nucleic acid otherwise detectable by FACS analysis. In other embodiments, the reporter gene encodes a protein or nucleic acid which confers a selectable growth phenotype to the host cell.

By "operably linked" is meant that a gene and transcriptional regulatory sequence(s) are connected in such a way as to permit expression of the gene in a manner dependent upon factors interacting with the regulatory sequence(s). In the case of the reporter gene, at least one DNA binding domain (DBD) recognition element will also be operably linked to the reporter gene such that transcription of the reporter gene will be dependent, at least in part, upon bait-prey complexes bound to the recognition element. Although, as explained, a single fusion protein with a covalently attached activation tag may be used when selecting DBDs on their binding sites.

The terms "basic promoter" or "minimal promoter", as used herein, are intended to refer to the minimal transcriptional regulatory sequence that is capable of initiating transcription of a selected DNA sequence to which it is operably linked. This term is intended to represent a promoter element providing basal transcription.

The term "transcription factor" refers to any protein or modified form thereof that is involved in the initiation of transcription but which is not itself a part of the polymerase. Transcription factors are proteins or modified forms thereof, which interact preferentially with specific nucleic acid sequences, i.e., regulatory elements, and which in appropriate conditions stimulate transcription ("transcriptional activators") or repress transcription ("transcriptional repressors"). Some transcription factors are active when they are in the form of a monomer. Alternatively, other transcription factors are active in the form of oligomers consisting of two or more identical proteins or different proteins (heterodimer). The factors have different actions during the transcription initiation: they may interact with other factors, with the RNA polymerase, with the entire complex, with activators, or with DNA. The factors are generally classifiable into two groups: (i) the general transcription factors, and (ii) the transcription activators. Transcription factors usually contain one or more regulatory domains. However, note that some constructs can use DBDs covalently attached to polymerase subunits.

The term "regulatory domain" refers to any domain which regulates transcription, and includes both activation and repression domains. The term "activation domain" denotes a domain in a transcription factor which positively regulates (increases) the rate of gene transcription. The term "repression domain" denotes a domain in a transcription factor which negatively regulates (inhibits or decreases) the rate of gene transcription.

The term "transcriptional activator" as used herein refers to a protein or protein complex which is capable of activating expression of a gene. Thus, as used herein, a transcriptional activator can be a single protein or alternatively it can be composed of several units at least some of which are not covalently linked to each other. A transcriptional activator typically has a modular structure, i.e., comprises various domains, such as a DNA binding domain, and one or more transcriptional activation tags.

The term "cofactor" which is used interchangeably herein with the terms "co-activator", "adaptor" and "mediator" refers to proteins which either enhance or repress transcription in a non-gene specific manner, e.g., which lack intrinsic DNA binding specificity. Thus, cofactors are general effectors. Positively acting cofactors do not stimulate basal transcription, but enhance the response to an activator.

A "dimerization domain" is defined as a domain that induces formation of dimers between two proteins having that domain, while a "tetramerization domain" is defined as a domain that induces formation of tetramers amongst proteins containing the tetramerization domain. An "oligomerization domain", generic for both dimerization and tetramerization domains, facilitates formation of oligomers, which can be of any subunit stoichiometry (of course greater than one).

The term "interact" as used herein is meant to include detectable interactions between molecules. Interactions may be, for example, protein-protein, protein-nucleic acid, drug-protein, or drug-nucleic acid.

By "covalently bonded" it is meant that two domains are joined by covalent bonds, directly or indirectly. That is, the "covalently bonded" proteins or protein moieties may be immediately contiguous or may be separated by stretches of one or more amino acids within the same fusion protein.

By "altering the expression of the reporter gene" is meant a statistically significant increase or decrease in the expression of the reporter gene to the extent required for detection of a change in the assay being employed. It will be appreciated that the degree of change will vary depending upon the type of reporter gene construct or reporter gene expression assay being employed, as between FACS sorting and growth selection.

The terms "fluorescently active" and "fluorescent label" refer to the ability to emit radiation of a given wavelength as a result of excitement with radiation of a different wavelength than that emitted. Typically, fluorescent reporter groups are detected by exciting the reporter group with a higher energy light and then detecting the emission of some of the absorbed energy as a lower energy light. The term is also intended herein to cover chemiluminescent, phosphorescent as well as fluorescent materials. The exciting radiation is conventionally ultraviolet or visible light but may be infrared or other electromagnetic radiation.

As used herein, the term "fluorophore" is inclusive of fluorophore and fluorescent compounds known to be useful in flow cytometry Preferably, the fluorophore is phycoerythrin (PE) or fluoresceinisothiocyanate (FITC), but other useful fluorophores are known in the art.

The terms "interactors", "interacting proteins" and "candidate interactors" are used interchangeably herein and refer to a set of proteins which are able to form complexes with one another, preferably non-covalent complexes.

By "test protein" or "test polypeptide" is meant all or a portion of one of a pair of interacting proteins provided as part of the bait or prey fusion proteins.

By "randomly generated" is meant sequences having no predetermined sequence; this is contrasted with "intentionally designed" sequences which have a DNA or protein sequence or motif determined prior to their synthesis.

The terms "directed evolution" and "creation by directed evolution" mean bringing forth a sequence not found in nature which, e.g., encodes a novel molecule or DBD binding domain by mutating or randomizing genes and then imposingrationally designed selection conditions and pressures. This may proceed through several cycles with increasingly stringent selection/screening criteria.

The term "mutagenesis" refers to techniques for the creation of heterogeneous population of genes, e.g., by irradiation, chemical treatment, low fidelity replication, etc.

By "amplification" or "clonal amplification" is meant a process whereby the density of host cells having a given phenotype is increased.

The terms "pool" of polypeptides, "polypeptide library" or "combinatorial polypeptide library" are used interchangeably herein to indicate a variegated ensemble of polypeptide sequences, where the diversity of the library may result from cloning or be generated by mutagenesis or randomization. The terms "pool" of genes , "gene library" or "combinatorial gene library" have a similar meaning, indicating a variegated ensemble of nucleic acids.

By "screening" is meant a process whereby a gene library is surveyed to determine whether there exists within this population one or more genes which encode a polypeptide having a particular binding characteristic(s) in the interaction trap assay.

By "selection" is meant a process whereby candidates from a library are expressed in specialized cells, and these cells are subjected to growth conditions (selective conditions) under which only those cells in which expression of a reporter gene is measurably altered will survive or grow.

The term "breakthrough false positive" or "background false positive" refers to host cells in which expression of the reporter gene occurs, e.g., by at least a statistically significant amount, in a manner which is independent on the interaction of the bait and prey proteins (in the case of a two hybrid assay) and the bait and DNA target sequence (in the case of a one hybrid assay).

The term "zinc finger protein" or "ZFPs" or "zinc finger polypeptide" refers to proteins that bind to DNA, RNA and/or protein, in a sequence-specific manner, by virtue of a metal stabilized domain known as a zinc finger. See, for example, Miller et al. (1985) *EMBO J.* 4:1609–1614; Rhodes et al. (1993) *Sci. Amer*. Feb:56–65; and Klug (1999) *J. Mol. Biol*. 293:215–218. The most widely represented class of ZFPs, known as the $C_2H_2$ (SEQ ID NO: 4) ZFPs, comprises proteins that are composed of zinc fingers that contain two conserved cysteine residues and two conserved histidine residues. Over 10,000 $C_2H_2$ (SEQ ID NO: 4) zinc fingers have been identified in several thousand known or putative transcription factors. Each $C_2H_2$ (SEQ ID NO: 4) zinc finger domain comprises a conserved sequence of approximately 30 amino acids that contains the invariant cysteines and histidines in the following arrangement: -Cys-$(X)_{2-4}$-Cys-$(X)_{12}$-His-$(X)_{3-5}$-His (SEQ ID NO: 1). In animal genomes, polynucleotide sequences encoding this conserved amino acid sequence motif are usually found as a series of tandem duplications, leading to the formation of multi-finger domains within a particular transcription factor. As used herein, "zinc finger protein" refers to known zinc finger proteins, or fragments thereof, or to novel polypeptides isolated by the methods of the invention.

The terms "phage vector" and "phagemid" are art-recognized and generally refer to a vector derived by modification of a phage genome, containing an origin of replication for a bacteriophage, and preferably, though optional, an origin (ori) for a bacterial plasmid. In certain embodiments, a library of replicable phage vectors, especially phagemids (as defined herein), encoding a library of fusion proteins and/or reporter gene constructs, is generated and used to transform suitable host cells.

The term "helper phage" refers to a phage which is impaired or defective in its ability to replicate. The defect can be one which results from removal, mutation, or inactivation of phage genomic sequence required for phage replication. Helper phage can be used to infect cells harboring a phagemid resulting in the production of infectious phage particles primarily harboring single-standed DNA forms of the phagemid. Examples of helper phage include M13K07, VCS-M13, M13 derivatives, and f1 derivatives.

The phrase "varying the growth conditions of the host cell," or the like, refers to changing or modifying any environmental factor which may affect the growth of a cell, including, for example, changing the composition of the growth medium, adding a drug to the growth medium, changing the temperature at which the cells are grown, changing the agitation rate to which the cells are exposed, changing the length of time the cells are grown, changing the amount of light to which the cells are exposed, changing the amount of $CO_2$ and/or $O_2$ to which the cells are exposed, etc.

The term "desired expression level," or the like, refers to the level of expression of a reporter gene which produces a useful means for selecting of a population of cells comprising a test polypeptide that may or may not interact with at least one other polypeptide or at least one nucleic acid (DNA or RNA) sequence. In various embodiments, a desired expression level refers to an increase, a decrease, or no change in the level of the reporter gene as compared to the basal level of expression of the reporter gene. In other embodiments, a desired expression level refers to an increase, a decrease, or no change in the level of the reporter gene upon application of an external factor as compared to the level of expression of the reporter gene before application of the external factor. The external factor can be anything which varies the growth conditions of the cell, as described herein, and in a particular embodiment refers to contacting the host cell with a test agent.

The term "translational element" refers to any nucleic acid sequence which is sufficient to permit translation of an RNA sequence into a polypeptide. In certain embodiments, the translational element refers only to a start codon (ATG), whereas in other embodiments, it refers to a sequence comprising a start codon, ribosome binding sites, etc.

The phrase "analyzed by FACS," or the like, as used herein, is meant to include monitoring and/or sorting of a population of cells using FACS.

The terms "agent" or "test agent" are used herein interchangeably and are meant to include, but are not limited to, peptides, nucleic acids, carbohydrates, small organic molecules, natural product extracts, and libraries thereof.

The term "agonize" as used herein, refers to an augmentation of the formation of a protein-protein or protein-DNA complex, wherein augmentation may mean an increase in the amount of, or the increase in the duration of, a complex.

The term "antagonize", as used herein, refers to an inhibition of the formation of a protein-protein or protein-DNA complex, wherein inhibition may mean a decrease in the amount or duration of a complex. tive site.

The term "tunable" or "tunable selection" refers to the ability to control the degree of growth advantage conferred by a reporter gene being expressed in a cell by varying the growth conditions of the cell.

The term "imp⁻ strain" refers to a strain of bacteria containing a mutation in the increased membrane permeability locus leading to increased permeability of the outer membrane of the cell (Sampson et al., Genetics 122(3): 491–501 (1989)).

The term "differentially interact," or the like, refers to the ability of a first molecule (a polypeptide, nucleic acid, or small molecule) to interact with at least two other test molecules (polypeptides, nucleic acids, or small molecules). In various embodiments, a first molecule will differentially interact with two other test molecules wherein it (i) interacts strongly with both test molecules, (ii) interacts strongly with one of the test molecules and weakly with the other test molecule, or (iii) interacts weakly with both test molecules.

The term "differentially modulates," or the like, as used herein, refers to the ability of a test agent to affect the interaction of a first molecule (a polypeptide, nucleic acid, or small molecule) with at least two other test molecules (polypeptides, nucleic acids, or small molecules). In various embodiments, a test agent will differentially modulate the interaction of a first molecule with two other test molecules wherein it (i) strongly affects the interaction of the first molecule with both test molecules, (ii) strongly affects the interaction of the first molecule with one of the test molecules and weakly affects the interaction of the first molecule with the other test molecule, or (iii) weakly affects the interaction of the first molecule with both test molecules.

The term "interacts to a desired extent," or the like, refers to an interaction between molecules (polypeptide-polypeptide or polypeptide-nucleic acid) which results in a desired level of expression of a reporter gene, in accord with the methods of the invention. A desired extent of interaction may be a strong interaction between two molecules, a weak interaction between two molecules, or no interaction between two molecules. Additionally, a desired extent of interaction may result in an increase, a decrease, or no change in the level of expression of the reporter gene as compared to the basal level of expression of the reporter gene in accord with the various embodiments of the invention.

The term "basal expression level" refers to the level of expression that occurs in the absence of a productive interaction between two polypeptides or a polypeptide and a DNA sequence.

III. Exemplary Embodiments for ITS Reagents

Before describing the various embodiments of the subject interaction trap assays, we first provide a generic description of the "bait" and "prey" proteins and reporter gene constructs used in the various assays formats. It is noted that the following description of particular arrangements of test polypeptide sequences in terms of being part of the bait or prey fusion proteins is, in general, arbitrary. As will be apparent from the description, the test polypeptide portions of any given pair of interacting bait and prey fusion proteins may, in certain embodiments, be swapped with each other.

A. Bait Protein Constructs for Two Hybrid Format

One of the first steps in the use of the interaction trap system of the present invention is to construct the bait fusion protein. Sequences encoding a first interacting domain are cloned in-frame to a sequence encoding, depending on the embodiment, a known or potential (test) DNA binding domain (DBD), e.g., a polypeptide which may specifically bind to a defined nucleotide sequence of a reporter gene construct. A basic requirement for the bait fusion protein is that it alone causes little or no transcriptional activation of the reporter gene in the absence of an interacting prey fusion protein or DNA sequence. In addition, the DBD and interacting domain should not affect the activity of the other. (However, when selecting DBDs or their binding sites from a variegated library, the DBD may be fused directly to the activation domain or the polymerase subunit.)

B. Prey protein Constructs for two Hybrid format

The subject assay also utilizes a chimeric prey protein. In preferred embodiments, the prey fusion protein comprises: (1) a second interacting domain, capable of forming an intermolecular association with the first interacting domain of the bait polypeptide, and (2) an activation tag, such as a polymerase interacting domain or a polymerase subunit. As described above, protein-protein contact between the bait and prey fusion proteins (via the interacting domains) links the DNA-binding domain of the bait fusion protein with the polymerase interaction domain (or a polymerase subunit) of the prey fusion protein, generating a protein complex capable of directly recruiting a functional RNA polymerase enzyme to promoter sequences proximal to the DNA-bound bait protein, i.e., activating transcription of the reporter gene.

DNA dependent RNA polymerase in *E. coli* and other bacteria consists of an enzymatic core composed of subunits $\alpha$, $\beta$, and $\beta'$ in the stoichiometry $\alpha_2\beta\beta'$, and one of several alternative $\sigma$ factors responsible for specific promoter recognition. In one embodiment, the prey fusion protein includes a sufficient portion of the amino-terminal domain of the α subunit to permit assembly of transcriptionally active RNA polymerase complexes which include the prey fusion protein. The α subunit, which initiates the assembly of RNA polymerase by forming a dimer, has two independently folded domains (Ebright et al. (1995) *Curr Opin Genet Dev* 5:197). The larger amino-terminal domain (α-NTD) mediates dimerization and the subsequent assembly of the polymerase complex. The prey polypeptide can be fused in frame to the α-NTD, or a fragment or mutant thereof, which retains the ability to assemble a functional RNA polymerase complex.

The present invention also contemplates the use of polymerase interaction domains containing portions of other RNA polymerase subunits or portions of molecules which associate with an RNA polymerase subunit or subunits. Contemporary models of the polymerase complex predict a substantial degree of intramolecular motion within the transcription complex. Movement of parts of the enzyme complex relative to each other is believed to be realized by structurally independent domains, such as the N-terminal and C-terminal domains of the α subunit described above. Accordingly, it is possible that the paradigm of transcriptional activation realized with fusion proteins incorporating only a portion of the subunit is also applicable to fusion proteins generated with portions of other polymerase subunits, e.g., with portions of the β, β', ω and/or σ subunits. The use of portions of such other subunits to generate a prey fusion protein are, like the α-NTD example above, useful if they provide fusion proteins which retain the ability to form active polymerase complexes. For example, Severinov et al. (1995) *PNAS* 92:4591 describes the ability of fragments of the β subunit (encoded by the *E. coli* rpoB gene) to reconstitute a functional polymerase enzyme. It is noted that it may be a formal requirement of embodiments utilizing prey fusion proteins including PIDS of the β, β', ω and/or σ subunits that other fragments of the subunit be provided, e.g., co-expressed, in the host cell. See also, Dove et al. (1997) *Nature* 386:627.

Additionally, given the general conservation of the polymerase subunits amongst bacteria, the present invention also specifically contemplates prey fusion proteins derived with polymerase interaction domains of RNA polymerase subunits from other bacteria, e.g., *Staphylococcus aureus* (Deora et al. (1995) *Biochem Biophys Res Commun* 208: 610), *Bacillus subtilis*, etc.

In an alternative embodiment, instead of a polymerase interaction domain, the prey fusion protein can include an activation domain of a transcriptional activator protein. The bait fusion protein, by forming DNA bound complexes with the prey fusion protein, can indirectly recruit RNA polymerase complexes to the promoter sequences of the reporter gene, thus activating transcription of the reporter gene. To illustrate, the activation domain can be derived from such transcription factors as PhoB or OmpR. The critical consideration in the choice of the activation domain is its ability to interact with RNA polymerase subunits or complexes in the host cell in such a way as to be able to activate transcription of the reporter gene.

C. Bait Protein Constructs for one Hybridformat

In certain embodiments of the subject invention, the interaction trap assay is designed to detect interaction between a potential DNA binding domain and a potential DBD recognition element. In those embodiments, it is not necessary that the transcriptional activiation activity be separated from the bait protein into the prey protein, as it is in the two hybrid format. Thus, in a one hybrid format, sequences encoding a known or potential (test) DNA binding domain (DBD), e.g., a polypeptide which may specifically bind to a defined nucleotide sequence of a reporter gene construct fused in frame to an activation domain, such as a PID. As above, the basic requirement for the bait fusion protein is that it alone causes little or no transcriptional activation of the reporter gene in the absence of interaction with the DBD recognition sequence of the reporter gene. In addition, the DBD and activation domain should not affect the activity of the other.

D. Reporter Gene Constructs

The level of reporter gene expression ultimately measures the end stage of the above described cascade of events, e.g., transcriptional modulation, and permits the isolation and/or amplification of ITS host cells in a manner dependent on the interaction of the bait and prey proteins and the transcriptional regulatory element of the reporter gene. Accordingly, in practicing one embodiment of the assay, a reporter gene construct is inserted into the reagent cell. Typically, the reporter gene construct will include one or more reporter genes in operative linkage with one or more transcriptional regulatory elements which include, or are linked to, at least one known or potential DBD recognition element for the DBD of the bait fusion protein. In various embodiments, the reporter gene construct may contain at least one, two, three, four, or five known or potential DBD recognition elements. Based on the teachings described herein, those of skill in the art could readily identify or synthesize reporter genes and transcriptional regulatory elements useful in the subject methods. (When testing specificity, one also may have reporters with binding sites that you would prefer the protein not recognize.) Further detail is provided below.

IV. Exemplary Embodiments for Analysis of Large Libraries by Growth Selection

We have discovered that use of selectable reporter genes which confer a growth advantage to a prokaryotic host cell, rather than merely a visual selection marker allows the interaction trap assay to be used to screen libraries of potential protein-protein or protein-DNA interactors exceeding $10^7$ members. In the prior art systems, lack of stringency can result in isolation of a significant population of non-specific interacting pairs, i.e., false positives. In large libraries, a high percentage of false positives can make the isolation and identification of true interactors from a large library time consuming, if not impossible.

In the ITS formats of the subject invention, we have shown that the use of reporter genes providing a highly stringent amplification profile can in fact reduce the number of false positives, especially breakthrough false positives, being amplified to the point that large scale library screening is in fact feasible. Thus, the subject assay can be set up to utilize a reporter gene system that reduces the number of false positive interactions to less than 50% of an enriched library, and more preferably less than 25 percent, or even 10, 5 or 1 percent. In a preferred embodiment, the assay reduces the occurrence rate of breakthrough false positives to less than $1:10^7$, and even more preferably less than $1:10^8$, $1:10^9$ or even $1:10^{10}$.

In this embodiment of the present invention, the reporter gene is chosen on the basis of its ability to facilitate isolation and/or amplification of ITS cells on the basis of a selective growth advantage, e.g., the ability to grow, and preferably can provide a highly stringent amplification profile which reduces the number of false positives being amplified. Accordingly, in practicing one embodiment of the assay, a reporter gene construct is inserted into the reagent cell in order to generate a selectable growth advantage dependent on interaction of the bait and prey fusion proteins with each other and the regulatory elements of the reporter gene. Typically, the reporter gene construct will include a reporter gene in operative linkage with one or more transcriptional regulatory elements which include, or are linked to, a potential DBD recognition element for the DBD of the bait fusion protein, with the level of expression of the reporter gene providing the prey protein interaction-dependent growth advantage (or the DBD-DNA interaction when selecting for DNA binding).

Based on the teachings described herein, those of skill in the art could readily identify or synthesize reporter genes and transcriptional regulatory elements useful in the subject methods. In general, the reporter gene is selected to provide a selection method such that cells in which the reporter gene is activated have a growth advantage. For example the reporter could enhance cell viability, e.g., by relieving a cell nutritional requirement, and/or provide resistance to a drug. To further illustrate, examples of suitable reporter genes include those which encode proteins conferring antibiotic resistance to the host bacterial cell, though more preferably are a gene which encodes a protein required to complement an auxotrophic phenotype. A preferred reporter gene is the HIS3 gene, which permits $E.\ coli$ cells bearing a deletion of the hisB gene to grow in the absence of histidine. 3-AT, a competitive inhibitor of HIS3, can be used to increase the level of HIS3 expression required for growth in the absence of histidine. Thus, 3AT can be used to increase the stringency of the selection.

In bacteria, suitable positively selectable (beneficial) genes include genes involved in biosynthesis or drug resistance. Countless genes are potential selective markers. Certain of the above are involved in well-characterized biosynthetic pathways. In the simplest case, the cell is auxotrophic for an amino acid or nucleotide precursor, such as histidine, uracil, leucine, tryptophane or adenine, in the absence of activation of the reporter gene. Auxotrophy means the inability of the micro-organism to synthesise certain growth factors, for example amino acids, from simple precursors. In contrast to the corresponding wild type strains, auxotrophic mutants therefore do not grow on minimal medium. On the contrary, they require a complete medium or minimal medium supplemented with components necessary for growth which they cannot synthesize themselves. Activation of the ITS leads to synthesis of an enzyme, encoded by the reporter gene, required for biosynthesis of the amino acid and the cell becomes prototrophic for that amino acid (does not require an exogenous source). Thus the selection is for growth in the absence of that amino acid in the culture media.

To further illustrate, we have discovered that, surprisingly, the HIS3 reporter gene can be used to rescue a prokaryotic host cell in HIS selective media with sufficient stringency to successfully isolate interacting pairs from a large library of variants. Lack of stringency in other systems can result in isolation of a significant population of non-specific interacting pairs, i.e., false positives. In large libraries, a high percentage of false positives can make the isolation and identification of true interactors time consuming, if not impossible. In the case of the HIS3 reporter, the use of 3-amino-triazole (3AT), a competitive inhibitor of HIS3, selects for cells in which the HIS3 reporter is highly expressed (i.e., increases the stringency of the selection), and thereby lowers the number of false positives due to breakthrough in the enriched product. Using different levels of 3-AT allows "tuning" or the selection stringency.

Another exemplary reporter gene which may be used in the subject assay is the β-lactamase system. β-lactams are antibiotics which act by interfering with cell wall biosynthesis in the bacteria resulting in impaired cellular function, altered cell morphology or lysis. Bacteria have developed the ability to resist β-lactam activity through the production of β-lactamases which are enzymes that irreversibly hydrolyze the amide bond of the β-lactam ring thus rendering the antibiotic inactive. A specific example of a β-lactamase enzyme is taught by Stemmer (Nature 1994 Aug 4;370 (6488):389) which provides a variant of TEM-1 which is more resistant to cefotaxime, e.g., has a higher minimum inhibitory concentration. Recently, various compounds capable of inhibiting β-lactamase activity have been developed thus permitting antibiotic growth selection of various bacterial strains even in the presence of β-lactamases. This system also provides a tunable selection method. A bacterial cell expressing a β-lactamase enzyme as the reporter gene can be grown in the presence of a constant level of β-lactam antibiotic and a variable concentration of β-lactamase inhibitor. Control of the level of β-lactamase inhibitor permits control of the stringency of the growth conditions—a high concentration of inhibitor results in more stringent growth conditions whereas a low concentration of inhibitor results in less stringent growth conditions. The gene encoding for the β-lactamase enzyme may be introduced into the bacteria such that it is constitutively or regulatably expressed. See for example, Liras et al., Appl. Microbiol. Biotechnol. 54(4): 467–475 (2000); Saves et al., J. biol. Chem. 270(31): 18240–18245 (1995); Thomson et al., J. Antimicrob. Chemother. 31(5): 655–64 (1993); Maddux, Pharmacotherapy 11(2(pt 2)): 40S–50S (1991); Selzer et al., Nat. Struct. Biol. 7(7): 537–41 (2000); Huang et al., J. Biol. Chem. 275(20): 14964–8 (2000); Shaywitz et al., Mol. Cell Biol. 20(24): 9409–9422 (2000).

Any combination of β-lactamase, β-lactam antiobiotic and β-lactamase inhibitor may be used in conjunction with the tunable selection system. Exemplary β-lactamase enzymes include TEM-1, TEM-2, OXA-1, OXA-2, OXA-3, SHV-1, PSE-1, PSE-2, PSE-3, PSE-4 and CTX-1. Exemplary β-lactam antibiotics include penicillins, cephalosporins, monobactams and carbapenems. Exemplary β-lactamase inhibitors include clavulanic acid, sulbactam, tazobactam, brobactam, β-lactamase inhibitor peptides (BLIP) and various mutants of BLIP. Examples of particular combinations of β-lactam antibiotics and b-lactamase inhibitors which have been used include ticarcillin and clavulanate, amoxicillin and clavulanate and ampicillin and sulbactam.

Thus, in preferred embodiments, the subject assay can be set up to utilize a reporter gene system which provides sufficient stringency for detecting interactions such that the number of false positive interactions is less than 50% of an enriched library, and more preferably less than 25 percent, or even 10, 5 or 1 percent.

V. Exemplary embodiments for flow-ITS

Another aspect of the present invention provides methods and reagents for practicing various forms of interaction trap assays using flow cytometry, preferably as a high throughput means (supra). The subject "flow ITS" can be used, for example, to screen libraries of potential protein-protein or protein-nucleic acid interactions. In preferred embodiments, the subject ITS system can be used to screen libraries of potential interactors exceeding $10^7$ members. See Daugherty et al., J. Immun. Methods 243: 211–227 (2000) for a review on screening of cell-based libraries using flow cytometry.

The reporter gene(s) used in this embodiment of the invention ultimately measure the end stage of the above described cascade of events, e.g., transcriptional modulation, with the level of expression of a product(s) which is fluorescently active. The reporter gene of the flow-ITS can be any gene that expresses a FACS detectable gene product, which may be RNA or protein.

There are at least two basic designs for the flow-ITS. In a "direct detection system" the reporter gene encodes a product which is readily detectable by flow cytometry due to its own fluorescence activity (a "direct FACS tag"). In the alternative, the flow-ITS is derived as an "indirect detection system" wherein the reporter gene product is detected by FACS upon combination with a fluorescently active agent which specifically binds to and/or is modified by the reporter gene product. Thus, the reporter gene may encode a "direct FACS tag", e.g., a fluorescent polypeptide or a polypeptide which may generate a fluorescent signal by enzymatic action, or an "indirect FACS tag", e.g., a polypeptide which binds and/or modifies a fluorescently active molecule to generate a fluorescent signal. Chemiluminescent reporter groups, which are for ease of reading referred to herein as fluorescent groups, are detected by allowing them to enter into a reaction, e.g., an enzymatic reaction, that results in energy in the form of light being emitted.

The reporter gene may also be included in the construct in the form of a fusion gene with a gene that includes desired transcriptional regulatory sequences or exhibits other desirable properties.

In one embodiment, the reporter gene encodes a fluorescently active polypeptide. Examples of such reporter genes include, but are not limited to firefly luciferase (deWet et al. (1987), *Mol. Cell. Biol.* 7:725–737); bacterial luciferase (Engebrecht and Silverman (1984), *PNAS* 1: 4154–4158; Baldwin et al. (1984), *Biochemistry* 23: 3663–3667); phycobiliproteins (especially phycoerythrin); green fluorescent protein (GFP: see Valdivia et al. (1996) *Mol Microbiol* 22: 367–78; Cormack et al. (1996) *Gene* 173 (1 Spec No): 33–8; and Fey et al. (1995) *Gene* 165:127–130. Both the GFPs and the phycobiliproteins have made an important contribution in FACS sorting generally because of their high extinction coefficient and high quantum yield, and are accordingly preferred products of the reporter gene.

A preferred embodiment utilizes a GFP which has been engineered to have a higher quantum yield (brighter) and/or altered excitation or emmision spectra relative to wild-type GFPs. In general, the fluorescence levels of intracellular wild-type GFP are not bright enough for flow cytometry. However, a wide variety of engineered GFPs are known in the art which show both improved brightness and signal-to-noise ratios. For instance, the subject reproter gene can encode a GFP-Bex1 (S65T, V163A) or GFP-Vex1 (S202F, T203I, V163A). See Anderson et al. (1996) *Genetics* 93:8508. Other modified GFPs are described, for example, in U.S. Pat. Nos. 5,360,728 and 5,541,309 which describe modified forms of apoaequorin with increased bioluminescence.

In other embodiments, the reporter gene encodes an enzyme which, by acting on a substrate, produces a fluorescently active product. For instance, fluoroscein-di-β-D-galactopyranoside (FDG) is a useful substrate for a reporter gene encoding a β-galactosidase in detection by flow cytometry, particularly in gram negative bacteria. See Plovins et al. (1994) *Applied Envir Micro* 60:4638; and Alvarez et al. (1993) *Biotechniques* 15:974.

In yet other embodiments, the reporter gene product is not itself sufficiently fluorescently active for FACS purposes. Rather, the reporter gene product is one which is able to bind to a molecule (or complex of molecules), referred to herein as a "secondary fluorescent tag", which provides a fluorescently active moiety for detection by FACS. A preferred criteria for the selection of the reporter gene product in these embodiments is that the host cell, except for the reporter gene product, does not produce any other protein, etc., which binds to the secondary fluorescent tag at any appreciable level which would confound the FACS sorting of the ITS cells.

In preferred embodiments of the indirect detection system, the reporter gene encodes a protein which is associated with the cellular membrane and is at least partially exposed to the extracellular milieu. For instance, the indirect FACS tag can be a transmembrane protein having an extracellular domain, or an extracellular protein with some other form of membrane localization signal which keeps the tag sequestered on the surface of the ITS cell, e.g., such as a myristol, farnesyl or other prenyl group. The indirect FACS tag can be a protein which is native to the host cell, but not normally expressed in the ITS cell either because of its strain or the conditions under which the ITS is run. In other embodiments, the indirect FACS tag is a protein which includes a portion that is non-native to the host cell, e.g., it is a naturally occurring polypeptide sequence from another species or it is man-made polypeptide sequence, and it is the heterologous portion of the fusion protein which is bound by the secondary fluorescent tag.

In an illustrative embodiment, the indirect FACS tag is a fusion protein including a polypeptide portion which is not native to the host cell. Recombinant proteins are able to cross bacterial membranes after the addition of bacterial leader sequences to the N-terminus of the protein (Better et al (1988) *Science* 240:1041–1043; and Skerra et al. (1988) *Science* 240:1038–1041). In addition, recombinant proteins have been fused to outer membrane proteins for surface presentation. For example, one strategy for displaying exogenous proteins on bacterial cells comprises generating a fusion protein by inserting the exogenous protein into cell surface exposed portions of an integral outer membrane protein (Fuchs et al. (1991) *Bio/Technology* 9:1370–1372).

In selecting a bacterial cell which can display such indirect FACS tags, any well-characterized bacterial strain will typically be suitable, provided the bacteria may be grown in culture, and engineered to display the reporter gene product on its surface. Among bacterial cells, the preferred display systems include *Salmonella typhirnurium, Bacillus subtilis, Pseudomonas aeruginosa, Vibrio cholerae, Klebsiella pneumonia, Neisseria gonorrhoeae, Neisseria meningitidis, Bacteroides nodosus, Moraxella bovis*, and especially *Escherichia coli*. Many bacterial cell surface proteins useful in the present invention have been characterized, and works on the localization of these proteins and the methods of determining their structure include Benz et al. (1988) *Ann Rev Microbiol* 42: 359–393; Balduyck et al. (1985) *Biol Chem Hoppe-Seyler* 366:9–14; Ehrmann et al (1990) *PNAS* 87:7574–7578; Heijne et al. (1990) *Protein Engineering* 4:109–112; Ladner et al. U.S. Pat. No. 5,223,409; Ladner et al. WO88/06630; Fuchs et al. (1991) *Bio/technology* 9:1370–1372; and Goward et al. (1992) *TIBS* 18:136–140.

To further illustrate, the LamB protein of *E coli* is a well understood surface protein that can be used to generate the indirect FACS tag product of a reporter gene on the surface of a bacterial cell (see, for example, Ronco et al. (1990) *Biochemie* 72:183–189; van der Weit et al. (1990) *Vaccine* 8:269–277; Charabit et al. (1988) *Gene* 70:181–189; and Ladner U.S. Pat. No. 5,222,409). LamB of *E. coli* is a porin for maltose and maltodextrin transport, and serves as the receptor for adsorption of bacteriophages λ and K10. LamB is transported to the outer membrane if a functional N-terminal signal sequence is present (Benson et al. (1984) *PNAS* 81:3830–3834). As with other cell surface proteins, LamB is synthesized with a typical signal-sequence which is subsequently removed. Thus, the indirect FACS tag can be generated as a fusion gene of LamB, such that the resulting fusion protein comprises a portion of LamB sufficient to anchor the protein to the cell membrane with the indirect FACS tag fragment oriented on the extracellular side of the membrane. Secretion of the extracellular portion of the fusion protein can be facilitated by inclusion of the LamB signal sequence, or other suitable signal sequence, as the N-terminus of the protein.

The *E. coli* LamB has also been expressed in functional form in *S. typhimurium* (Harkki et al. (1987) *Mol Gen Genet* 209:607–611), *V. cholerae* (Harkki et al. (1986) *Microb Pathol* 1:283–288), and *K. pneumonia* (Wehmeier et al. (1989) *Mol Gen Genet* 215:529–536), so that one could display an indirect FACS tag in any of these species as a fusion to *E. coli* LamB. Alternatively, the LamB protein itself can serve as the indirect FACS tag.

Moreover, *K. pneumonia* expresses a maltoporin similar to LamB which could also be used. In *P. aeruginosa*, the D1 protein (a homologue of LamB) can be used (Trias et al. (1988) *Biochem Biophys Acta* 938:493–496). Similarly, other bacterial surface proteins, such as PAL, OmpA, OmpC, OmpF, OprF, Lpp-OmpA, PhoE, pilin, BtuB, FepA, VirG, FliC, FIIC, Type I pili, Pap pili, FhuA, Iuta, FecA and FhuE, may be used in place of LamB to generate the indirect FACS tag, e.g., in a bacterial cell. For a general review, see Georgion et al. (1997) *Nature Biotech* 15:29. Cell surface proteins such as OmpA, OmpF, OmpC are present at greater than $10^4$ molecules/cell, often as much as $10^5$ molecules/cell, which can provide good signal-to-noise ratios in FACS.

Those skilled in the art will also readily recognize surface polypeptides in eukaryotic cells which can suitably serve as indirect FACS tags. For instance, the indirect FACS tag can be a subunit of the yeast agglutin, such as AGα1 or AGA2. See for example Schreuber et al. (1993) *Yeast* 9:399. Another useful surface protein for use as an indirect FACS tag is the IL-8 receptor from mammalian cells.

Where the flow-ITS utilizes an indirect FACS tag, a secondary fluorescent tag must be provided in order to label the cells of FACS. The secondary fluorescent tag can be a fluorescently-labeled antibody or other binding moiety which specifically binds to the indirect FACS tag on the surface of the ITS cell. Where the indirect FACS tag is a receptor, or at least ligand binding domain thereof, the secondary fluorescent tags can also be a fluorescently-labeled ligand of the receptor. Such ligands can be polypeptides or small molecules.

In general, for use in flow cytometry, the fluorescently active tag should preferably have the following characteristics:
  (i) the molecules of the secondary fluorecent tag must be of sufficient size and chemical reactivity to be conjugated to a suitable fluorescent dye or the secondary fluorecent tag must itself be fluorescent,
  (ii) after any necessary fluorescent labeling, the secondary fluorecent tag preferably does not react with water,
  (iii) after any necessary fluorescent labeling, the secondary fluorecent tag preferably does not bind or degrade proteins in a non-specific way, and
  (iv) the molecules of the secondary fluorecent tag must be sufficiently large that attaching a suitable dye allows enough unaltered surface area (generally at least 500 Å$^2$, excluding the atom that is connected to the linker) for binding to the indirect FACS tag on the ITS cell.

Fluorescent groups with which the process of this invention can be used include fluorescein derivatives (such as fluorescein isothiocyanate), coumarin derivatives (such as aminomethyl coumarin), rhodamine derivatives (such as tetramethyl rhodamine or Texas Red), peridinin chlorophyll complex (such as described in U.S. Pat. No. 4,876,190), and phycobiliproteins (especially phycoerythrin).

In one preferred embodiment of the process, when the reporter group is fluorescein, detection of the ITS cells by FACS is achieved by measuring light emitted at wavelengths between about 520 nm and 560 nm (especially at about 520 nm), most preferably where the excitation wavelengths is about or less than 520 nm.

Chemiluminescent groups with which the subject secondary fluorescent tags can be generated include isoluminol (or 4-aminophthalhydrazide).

In other instances, the reporter gene can encode a nucleic acid which can be detected by flow cytometry upon interaction with a FACS label. In one embodiment, the reporter gene can "encode" a ribozyme, and detection of fluorescently active nucleic acid fragments can be detected for flow sorting upon addition of an appropriately labeled substrate for the ribozyme. For instance, the substrate nucleic acid can include a fluorogenic donor radical, e.g., a fluorescence emitting radical, and an acceptor radical, e.g., an aromatic radical which absorbs the fluorescence energy of the fluorogenic donor radical when the acceptor radical and the fluorogenic donor radical are covalently held in close proximity. See, for example, U.S. Ser Nos. 5,527,681, 5,506,115, 5,429,766, 5,424,186, and 5,316,691; and Capobianco et al. (1992) Anal Biochem 204:96–102. For example, the substrate nucleic acid has a fluorescence donor group such as 1-aminobenzoic acid (anthranilic acid or ABZ) or aminomethylcoumarin (AMC) located at one position on the plymer and a fluorescence quencher group, such as lucifer yellow, methyl red or nitrobenzo-2-oxo-1,3-diazole (NBD), at a different position. A cleavage site for the ribozyme will be diposed between each of the sites for the donor and acceptor groups. The intramolecular resonance energy transfer from the fluorescence donor molecule to the quencher will quench the fluorescence of the donor molecule when the two are sufficiently proximate in space, e.g., when the substrate is intact. Upon cleavage of the substrate, however, the quencher is separated from the donor group, leaving behind a fluorescent fragment. Thus, expression of the ribozyme results in cleavage of the substrate nucleic acid, and dequenching of the fluorescent group. Similar embodiments can be generated for peptide-based substrates of enzymes.

In certain embodiments, the flow-ITS can be designed to detect proteins which disrupt the interaction of two proteins. For instance, cDNA libraries can be screened for products which disrupt the binding of such protein pairs as cyclins and cyclin-dependent kinases. To further illustrate, the bait and prey proteins can be generated using known interactors. The cDNA library can be expressed as a third recombinant protein. Loss of expression of the reporter gene indicates the expression of gene encoding a protein which disrupts the interaction of the bait and prey proteins. Such loss would register, in the flow-ITS, as loss of a fluorescent signal in the FACS. In order to avoid potentially confounding results of such embodiments, the flow-ITS format can be modified slightly to provide a "reverse flow-ITS". In the reverse ITS, the reporter gene encodes a transcriptional repressor which is expressed upon interaction of the bait and prey proteins.

However, the host cell also includes a second reporter gene which, but for an operator sequence responsive to the repressor protein produced by the first reporter gene, would otherwise be expressed as a FACS tag detectable in the FACS step of the present method. Thus, the gene product of the first reporter gene regulates expression of the second reporter gene, the expression of the latter provides a means for indirectly scoring by FACS analysis for the expression of the former. Essentially, the first reporter gene can be seen as a signal inverter.

In this exemplary system, the bait and prey proteins positively regulate expression of the first reporter gene. Accordingly, where the first reporter gene is a repressor of expression of the second reporter gene, relieving expression of the first reporter gene by inhibiting the formation of complexes between the bait and prey proteins concomitantly relieves inhibition of the second reporter gene. For example, the first reporter gene can include the coding sequences for λcI. The second reporter gene can accordingly encode a direct or indirect FACS tag, and is under the control of a promoter which is constitutively active, but can be repressed by λcI. In the absence of a polypeptide which inhibits the interaction of the bait and prey protein, the λcI protein is expressed. In turn, that protein represses expression of the second reporter gene. However, an agent which disrupts binding of the bait and prey proteins results in a decrease in λcI expression, and consequently an increase in expression of the second reporter gene as λcI repression is relieved. Hence, the signal is inverted.

Still another consideration in generating the reporter gene construct concerns the placement of the DBD recognition element relative to the reporter gene and other transcriptional elements with which it is associated. In most embodiments, it will be desirable to position the recognition element such that on its own it does not significantly activate transcription from the promoter. In some instances, the axial position of the DBD relative to the promoter sequences can be important.

In certain embodiments, the sensitivity of the ITS can be enhanced for detecting weak protein-protein interactions by placing the DBD recognition sequence at a position permitting secondary interactions (if any) between other portions of the bait fusion protein and the RNA polymerase complex. For example, an apparent synergistic effect was observed when the X operator was moved close to or at its normal position (Dove et al., supra . While not wishing to be bound by any particular theory, this synergism is speculated to be the result of a bait-prey interaction and second interaction between DBD of λcI and a second polymerase subunit (σ).

It will also be understood by those skilled in the art that the sensitivity to the strength of the interactions between the bait and prey proteins can be "tuned" by adjusting the sequence of the recognition element. For example, the use of a strong λ operator instead of weak can improve the sensitivity of the assay to weak bait-prey interactions, as well as help to overcome lack of dimerization if no dimerization signals are included in the bait fusion protein.

The flow sorting cutoff, e.g., the strength of the fluorescent signal required for gating of cells through the sorter, can also be used to tune the system with respect to the strength of the interactions for which it generally selects.

A. Use of Multiple Reporter Genes

In particular embodiments, it may desirable to provide two or more reporter gene constructs, particularly reporter genes encoding products with different emission or excitation specta (Hawley et al., Biotechniques 30: 1028–1034 (2001)). The reporter genes can both encode direct FACS tags, indirect FACS tags, or a combination thereof. One or more of the reporter genes could also encode a polypeptide which can be used in the pre-flow enrichment step described below.

The simultaneous monitoring of two or more reporter genes (whether provided on the same or separate plasmids) can be used for at least 2 purposes: 1) to reduce the number of false positives; and 2) to ensure specificity of interaction pairs. For example, when selecting DBDs, one might select a protein that recognizes sites in one reporter construct but that does not bind as well to sites in the other.

There are currently available, from commercial sources, fluorescent proteins that have distinct emission spectra (e.g. DsRed (RFP), EYFP, EGFP, ECFP, EBFP). Using some of these fluorescent proteins and commercially available FACS equipment it is possible, in principle, to simultaneously and independently measure up to five distinct fluorescent reporter genes. There are also commercially available fluorescent proteins which have similar emission spectra but distinct excitation spectra (e.g. EGFP and GFPuv). Modifications to FACS equipment that enable the separate measurement of the fluorescence of a single cell when excited by different wavelengths (as described in Anderson et. Al., PNAS 93 8508–8511-1996) coupled with the use of additional reporter genes with similar emission spectra and distinct excitiation spectra could further increase the number of FACS tags that could be independently measured. One possible caveat with using more than one of these proteins in a single cell is that the commercially available genes that encode some of the proteins have very similar DNA sequences- having regions with very similar seqeunces in the same cell could have undesired effects upon the reporter constructs (due, for example, to recombination). This problem can be easily overcome because the genetic code is redundant-mutations can be made to the offending DNA sequences that do not change the amino acid sequence in the expressed protein.

In certain embodiments in which the subject flow-ITS is being used to identify a DNA binding domain (as described in further detail below), multiple reporter gene constructs can be used in order to faciliate isolation of domains with specific DNA binding activity. For example, the ITS host cell can include one or more reporter genes having transcriptional regulatory sequences for which a DNA binding domain is sought. At the same time, the cells can also include one or more reporter genes, encoding different FACS markers than above, under the control of transcriptional regulatory sequences which the DBD being sought should not bind to or activate expression from. Thus, cells encoding and expressing desired candidates can be isolated on the basis of differential expression of the reporter genes. This could be used to obtain proteins with desired site specificities or desired binding constants.

In certain embodiments it may be desirable to monitor the interactions of a DBD with a number of DNA sites greater than the number of independently measurably FACS tags in a given system. This could be accomplished by having multiple reporter constructs (on the same or different vectors) in which some of the DNA sites control the expression of separate copies of the same FACS tag—this would obviously make it impossible to independently measure all of the interactions between the DBD and each of the sites, but in some cases it is not necessary to independently monitor all of the interactions. For example, the desired DNA binding site could be operably linked to EGFP while a number a point mutants of the DNA binding site could each be operable linked to a copy of RFP. In this way, DBD's that interact with the target sequence, but that interact with NONE of the mutants of the target sequence, could be obtained by selecting for cells that express a very high amount of EGFP AND a very low amount of RFP.

Figure 7:
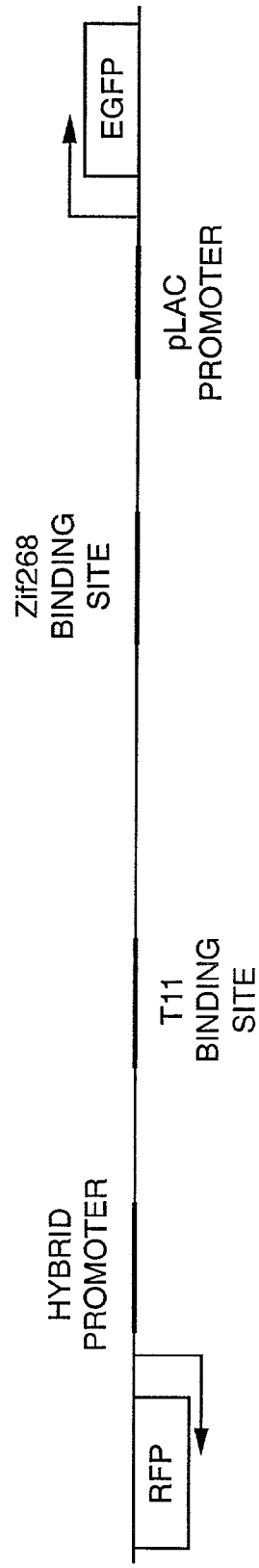
FIG. 7. Description of the two color TZ reporter system used for the experiment described in FIG. 8. In this reporter, EGFP and RFP are each under the control of a weak promoter (pLac and a hybrid pRM/pLac respectively). When a Gal11p containing bait protein binds to the Zif268 site, it causes increased EGFP production which can be measured in, e.g., fluorescence channel 1 (Fli 1). Similarly, when the Gal11p containing bait protein binds to the T11 site, it causes increased RFP production, which can be measured in, e.g., fluorescence channel 2 (Fli 2).

To further illustrate, FIG. 7 shows an exemplary construct containing two different DNA sites (T11 binding site and Zif268 binding site) to which DBD's that bind differentially to these sites are desired (i.e. DBD's which bind to the T11 site and not the Zif268 site, or vice-versa). Increased expression of EGFP, caused by the bait protein binding to the Zif268 site, provides a FACS sortable signal. Increased expression of RFP, caused by the bait protein binding to the T11 site, also provides a FACS sortable signal. Expression of EGFP and RFP can be independently detected either sequentially (in separate selection steps) or simultaneously (in the same selection step). Thus, in a simultaneous mode, the FACS machine can be programmed to gate on the detection of EGFP and RFP, selecting only those cells which are positive for EGFP and negative for RFP (or vice-versa). The use of multiple selection criteria also could be implemented by combining growth-rate selections or affinity-based cell sorting (using one set of reporters) with FACS-based sorting (using another set of reporters).

B. Fluorescence Activated Cell Sorting of ITS Cells

Fluorescence activated cell sorting techniques and equipment are well known in the art and are readily adapted for use in the subject assay. In recent years, optical/electronic instrumentation for detecting fluorescent labels on or in cells has become more sophisticated. For example, flow cytometry can be used to measure the amount of fluorescent label on individual cells at a rate exceeding 100,000 cells per second and isolate desired cells to high purity at a rate exceeding 70,000 cells per second. These instruments can excite fluorescence at many wavelengths of the WV, visible, and near IR regions of the spectrum.

In general, the flow cytometer for use in the present invention is constructed in such a way that ITS cells in suspension are introduced one at a time into an interrogation volume. Within this volume the cells are illuminated, generally by a laser, to excite the fluorescence tag associated with the cells. The fluorescence is then separated on the basis of its color, through the use of optical filters, and then detected and quantified by the electronics. The signals measured by each of these detectors, representing fluorescence at different wavelengths, are often referred to in the art as "fluorescence channels".

If only one fluorescence channel is being monitored, the results of this interrogation can be displayed in the form of histograms which represent the distributions of cells in the population examined. If two or more fluorescence channels are being monitored simultaneously, the results of this interrogation can be displayed in the form of one or more two-dimensional dot plots where each dot in the plot represents a single cell and the dot is drawn in the two-dimensional space so that the dot's position with respect to the x axis indicates the intensitiy of the cell's signal in the first fluorescence channel and the dot's position with respect to the y axis indicates the intensity of the cell's signal in the second fluorescence channel. Many tens of thousands of cells may be interrogated per second resulting in a very rapid description of the cell population.

The ITS cells are selectively isolated or sorted to high purity as they pass through this system on the basis of their fluorescence profile. If the cells are being sorted on the basis of a single fluorescence channel, a lower limit and an upper limit are drawn on the histogram for that fluorescence channel and all cells having a signal which falls between the lower and upper limits are isolated. If the cells are being sorted on the basis of two fluorescence channels, a polygon is drawn on the two dimensional dot plot for those two fluorescence channels and all cells that have signals that fall within the polygon are isolated. If cells are being sorted on the basis of three or more fluorescence channels, polygons are drawn on each of the relevant dot plots and cells falling within all of the relevant polygons are isolated. FACS equipment is also usually equipped to measure two non-fluorescent channels (i.e. channels at the same wavelength as the excitation wavelength) which are referred to in the art as "forward scatter" and "side scatter". These parameters are often used in the sorting criteria much as the fluorescence channels are used.

In the case where the desired cells are rare in the population (less than 1 in $10^4$) it is often necessary to perform multiple rounds of sorting to achieve a high purity of positive cells. Genetically identical cells have a distribution of fluorescent signals and at a certain frequency some cells which don't contain an ITS interaction will have a signal consistent with that of a positive cell (i.e. a cell containing an ITS interaction) by mere chance. As described in Daugerty, PS et al., Protein Engineering 11, p825–832 (1998), you can isolate a population of cells from your initial library that have fluorescence signals consistent with the desired cells, amplify this new population, and use this resulting amplified population in subsequent rounds of sorting. This process is repeated until the population has attained the desired purity of positive cells.

If the growth conditions can be varied so that cells containing an ITS interaction no longer have an elevated fluorescent signal, it is possible to perform multiple rounds of sorting under different conditions to retain cells that contain an ITS interaction while discarding cells which have an elevated fluorescent signal due to spurious genetic mutations. As described in Valdivia, R H and Falkow, S, Science 277, p2007–2011 (1997), you can first isolate a population of cells containing an elevated fluorescent signal under conditions in which the cells you desire will give you an elevated fluorescent signal. You then place this new population of cells under conditions where the cells you desire will no longer have an elevated fluorescent signal and isolate the cells from this new population that no longer have an elevated fluorescent signal thus discarding cells that had an elevated fluorescent signal for spurious reasons.

The level of fluorescence resulting from various levels of expression of the reporter gene can be compared to the level of fluorescence resulting from background expression of the reporter gene in a substantially identical cell that lacks heterologous DNA, such as the gene encoding the prey fusion protein. Any statistically or otherwise significant difference in the amount of transcription indicates that the prey fusion protein interacts with the bait fusion protein. Other controls include mutant bait proteins (in protein-protein interaction formats) and the use of DBD elements that disrupt interaction, to name but a few.

Another consideration which the practitioner of the subject assay must bear in mind is that bacteria, marine plankton and plant cells frequently exhibit a strong natural autofluorescence from chlorophyll or other pigments e.g. phycobiliproteins. Thus, practicing the subject flow-ITS requires that the autofluorescence of the host cell be accounted for as background, particularly where the FACS tag is detected at wavelengths above 600 nm.

C. Pre-flow Enrichment Affinity Purification or Growth Rate Selection

In certain embodiments of the subject assay, the ITS cells are subjected to a pre-flow enrichment step in which the ITS cells are first subjected to an affinity separation step before being subjected to FACS separation. By this step, high throughput separation of large initial populations of ITS cells can be carried out, e.g., initial ITS cell populations exceeding $10^{13-10^{15}}$ cells per day using conventional columns.

In this step, ITS cells that express a particular cell surface protein are identified and isolated in an affinity separation step. To accomplish this, the ITS cells include a reporter gene which encodes a surface FACS tag protein. Upon development of the interaction trap, the ITS cells are applied to an immobilized matrix which includes a moiety that interacts with the surface FACS tag protein. In this manner, ITS cells expressing the surface FACS tag can be sequestered on the matrix and thereby separated from ITS cells which do not express at least a certain threshold level of the surface FACS tag. The surface FACS tag can be a cell surface protein which also serves as an indirect FACS tag for the FACS step. Alternatively, the surface FACS tag can be a product of a second reporter gene, e.g., the cells includes at least two reporter genes, one which provides a surface FACS tag for affinity enrichment and one which provides a direct or indirect FACS tag.

The immobilized matrix can include an antibody or other binding moiety which specifically binds to the surface FACS tag of the ITS cell. Where the surface FACS tag is a receptor, or at least ligand binding domain thereof, the immobilized matrix can include a ligand of the receptor. Such ligands can be polypeptides or small molecules. The portion of the matrix which binds to the surface FACS tag on the ITS cells is, for ease, referred to collectively herein as the "binding agent".

With respect to affinity chromatography, it will be generally understood by those skilled in the art that a great number of chromatography techniques can be adapted for use in the present invention, ranging from column chromatography to batch elution. Typically, the binding agent is immobilized (reversibly or irreversibly) on an insoluble carrier, such as sepharose or polyacrylamide beads. The population of ITS cells is applied to the affinity matrix under conditions compatible with the binding of the surface FACS tag to binding agent. The population is then fractionated by washing with a solute that does not greatly effect specific binding of surface FACS tag and binding agent, but which substantially disrupts any non-specific binding of the ITS cells to the matrix. A certain degree of control can be exerted over the binding characteristics of the ITS cells recovered from the cell culture by adjusting the conditions of the binding incubation and subsequent washing. The temperature, pH, ionic strength, divalent cation concentration, and the volume and duration of the washing can select for ITS cells within a particular range of expression of the surface FACS tag.

After "washing" to remove non-specifically bound ITS cells, when desired, specifically bound ITS cells can be eluted by either specific desorption (using excess surface FACS tag) or non-specific desorption (using pH, polarity reducing agents, or chaotropic agents). In preferred embodiments, the elution protocol does not kill the organism used as the ITS cell such that the enriched population of ITS cells can be further amplified by reproduction. The list of potential eluants includes salts (such as those in which one of the counter ions is $Na^+$, $NH_4^+$, $Rb^+$, $SO_4^{2-}$, $H_2PO_4^-$, citrate, $K^+$, $Li^+$, $Cs^+$, $HSO_4^-$, $CO_3^{2-}$, $Ca^{2+}$, $Sr^{2+}$, $Cl^-$, $PO_4^{2-}$, $HCO_3^-$, $Mg_2^+$, $Ba_2^+$, $Br^-$, $HPO_4^{2-}$, or acetate), acid, heat, and, when available, soluble forms of the target antigen (or analogs thereof). Neutral solutes, such as ethanol, acetone, ether, or urea, are examples of other agents useful for eluting the bound ITS cells.

In preferred embodiments, affinity enriched ITS cells can be iteratively amplified and subjected to further rounds of affinity separation until enrichment of the desired binding activity is detected. In certain embodiments, the specifically bound ITS cells, especially bacterial cells, need not be eluted per se, but rather, the matrix bound ITS cells can be used directly to inoculate a suitable growth media for amplification. Cells obtained with this protocol may—if desired—be used for subsequent flow selection studies using one or more reporter constructs.

In an another embodiment, high-gradient magnetic cell separation (MACS) techniques can be used to fractionate the ITS cell population. The MACS System (Miltenyi Biotech, Inc., Sunnyvale, Calif.) utilizes a powerful magnet designed to extract cells that are specifically coated with ferrous-microbeads (50 nm in diameter) that are coupled to secondary antibodies, streptavidin or biotin. For instance, if a biotinylated primary antibody directed against a reporter surface FACS tag protein is used, the addition of the streptavidin beads will bind the subset of cells expressing the surface FACS tag. The ITS cells can be contacted, e.g., in batch, with the microbeads. The microbead coated cells can then be passed through a column surrounded by a large magnet. The coated cells are retained and the other cell types pass through the column. The column may be, optionally, subjected to a wash step. The bound cells are released when the magnet is removed and collected. This cell separation system can be used to enrich for or deplete a subpopulation of cells within the mixture. To further illustrate, a biotinylated antibody directed against the surface FACS tag can be incubated with the ITS cells for a period of time sufficient for, e.g., antibody binding to the surface FACS tag to reach equilibrium. The antibody/cell complexes can then be captured on an immobilized matrix derivatized with streptavidin, such as the MACS streptavidin-conjugated super-paramagnetic microbeads (Miltenyi Biotec). A mixture of cells labeled with biotin-conjugated antibodies (e.g., against the surface FACS tag) is passed through the streptavidin column which is surrounded by a powerful rare earth magnet such as a MACS separator (Miltenyi Biotech). The ITS cells which express the surface FACS tag will be differentially retained on the column relative to cells which do not express the surface FACS tag. By removing the column from the magentic field, the labeled ITS cells can be eluted from the column, e.g., as the "magnetic fraction". See, for example, DiNicola et al. (1996) *Bone Marrow Transplant* 18:1117.

In general, the affinity enrichment step will sacrifice some specificity for higher throughput. Conventional columns are typically capable of retaining about $10^9$ cells. However, the specificity of most such columns will typically be in the range of about 50 precent. This means that about $5 \times 10^8$ cells with the desired phenotype will be retained on the column. If one assumes that a particular "interaction event" in a cDNA library is occurs infrequently (about 1 in $10^5$), then one should be able to pass $5 \times 10^{13}$ cells through a single column. Assuming an average flow rate of about $5 \times 10^{10}$ cells per minute, it would take just under 17 hours to pass through $5 \times 10^{13}$ cells through one column.

D. General Applicability of Flow-ITS Approaches

We note that all of the Flow-ITS strategies described in this application are also applicable to not only prokaryotic cells but also yeast, mammalian, and other eukaryotic cells as well.

VI. Exemplary Methods for Generating Libraries

The variegated libraries of the subject method, be their diversity at the level of a coding sequence for a portion of one or both of the bait and prey proteins or the DBD recognition sequence of a reporter gene, can be from obtained from naturally occurring sources or the product of random or semi-random mutagenesis or synthesis with random or semi-random segments.

For instance, coding sequences can be members of a DNA expression library (e.g., a cDNA or synthetic DNA library, either random or intentionally biased) that are fused in-frame to to generate a variegated library of bait or prey proteins.

In an exemplary embodiment, cDNAs may be constructed from any mRNA population and inserted into an equivalent expression vector. Such a library of choice may be constructed de novo using commercially available kits (e.g., from Stratagene, La Jolla, Calif.) or using well established preparative procedures (see, for example, *Current Protocols in Molecular Biology*, Eds. Ausubel et al. John Wiley & Sons: 1992). Alternatively, a number of cDNA libraries (from a number of different organisms) are publicly and commercially available; sources of libraries include, e.g., Clontech (Palo Alto, Calif.) and Stratagene (La Jolla, Calif.). It is also noted that prey polypeptide need not be naturally occurring full-length proteins. In preferred embodiments, prey proteins are encoded by synthetic DNA sequences, are the products of randomly generated open reading frames, are open reading frames synthesized with an intentional sequence bias, or are portions thereof.

It will be appreciated by those skilled in the art that many variations of the prey and bait fusion proteins can be constructed and should be considered within the scope of the present invention. For example, it will be understood that, for screening polypeptide libraries, the identity of the prey polypeptide can be fixed and the bait protein can be varied to generate the library. Indeed, in certain embodiments it will be desirable to derive the prey fusion protein with a fixed prey polypeptide rather than a variegated library on the grounds that the single prey fusion protein can be easily tested for its ability to be assembled into a functional RNA polymerase enzyme. Moreover, where the prey fusion protein is derived with a polymerase interaction domain, the bait fusion protein is likely to be less sensitive to variations caused by the different peptides of the library than is the prey fusion protein. In such embodiments, a variegated bait polypeptide library can be used to create a library of bait fusion proteins to be tested for interaction with a particular prey protein.

There are many ways by which libraries of mutagenized can be generated from a degenerate oligonucleotide sequence. Chemical synthesis of a degenerate gene sequence can be carried out in an automatic DNA synthesizer, and the synthetic genes then ligated into an appropriate expression vector. The purpose of a degenerate set of genes is to provide, in one mixture, all of the sequences encoding the desired set of potential sequences. The synthesis of degenerate oligonucleotides is well known in the art (see for example, Narang, S A (1983) *Tetrahedron* 39:3; Itakura et al. (1981) *Recombinant DNA, Proc* 3rd *Cleveland Sympos. Macromolecules*, ed. A G Walton, Amsterdam: Elsevier pp273–289; Itakura et al. (1984) *Annu. Rev. Biochem.* 53:323; Itakura et al. (1984) *Science* 198:1056; Ike et al. (1983) *Nucleic Acid Res.* 11:477. Such techniques have been employed in the directed evolution of other proteins (see, for example, Scott et al. (1990) *Science* 249:386–390; Roberts et al. (1992) *PNAS* 89:2429–2433; Devlin et al. (1990) *Science* 249: 404–406; Cwirla et al. (1990) *PNAS* 87: 6378–6382; as well as U.S. Pat. Nos. 5,223,409, 5,198,346, and 5,096,815).

Alternatives to the above combinatorial mutagenesis also exist. For example, libraries of potential DNA binding domains can be generated using, for example, alanine scanning mutagenesis and the like (Ruf et al. (1994) *Biochemistry* 33:1565–1572; Wang et al. (1994) *J. Biol. Chem.* 269:3095–3099; Balint et al. (1993) *Gene* 137:109–118; Grodberg et al. (1993) *Eur. J Biochem.* 218:597–601; Nagashima et al. (1993) *J. Biol. Chem.* 268:2888–2892; Lowman et al. (1991) *Biochemistry* 30:10832–10838; and Cunningham et al. (1989) *Science* 244:1081–1085), by linker scanning mutagenesis (Gustin et al. (1993) *Virology* 193:653–660; Brown et al. (1992) *Mol. Cell Biol.* 12:2644–2652; McKnight et al. (1982) *Science* 232:316); by saturation mutagenesis (Meyers et al. (1986) *Science* 232: 613); by PCR mutagenesis (Leung et al. (1 989) *Method Cell Mol Biol* 1:11–19); by in vitro DNA shuffling (Stemmer ref.); or by random mutagenesis (Miller et al. (1992) *A Short Course in Bacterial Genetics*, CSHL Press, Cold Spring Harbor, N.Y.; and Greener et al. (1994) *Strategies in Mol Biol* 7:32–34).

A. Directed Evolution Approaches

Moreover, in a method of directed evolution, identified interacting pairs can be improved by additional rounds of mutagenesis, selection, and amplification, e.g., diversity can be introduced into one or both of the identified interacting pair, and the resulting library screened according to the present invention. The goal may be, for instance, to use such a process to optimize the binding characteristics, e.g., for tighter binders and/or better selectivity in binding. Diversity can be introduced by most any standard mutagenesis technique, such as by irradiation, chemical treatment, low fidelity replication, use of randomized PCR primters, etc.

The flow-ITS embodiment of the subject assay is particularly well suited for directed evolution applications. For instance, the easy with which small samples can be obtained at intermediate points permits the practionier to assess the progress of, for example, a randomization step or counter-selection step. The ability to tune the fluorescence cutoff values for gating cells and to use reporters with different sites also permits the user to readily adjust the stringency of the isolation step from one round of direct evolution to the next.

VII. Exemplary ITS Embodiments for Detecting DNA-Protein Interactions

In certain preferred embodiments, various of the embodiments of the subject method can be used to identify or optimize DNA-protein interactions. For example, the subject method can be used to identify mutant or composite DNA binding domains having desired sequence binding preferences. It can also be used to identify DNA sequences which are selectively bound by a given DNA binding protein and/or to determine the sequence specificity of a DNA binding protein.

DNA-binding proteins, such as transcription factors, are critical regulators of gene expression. For example, transcriptional regulatory proteins are known to play a key role in cellular signal transduction pathways which convert extracellular signals into altered gene expression (Curran and Franza, (1988) *Cell* 55:395–397). DNA-binding proteins also play critical roles in the control of cell growth and in the expression of viral and bacterial genes. A large number of biological and clinical protocols, including among others, gene therapy, production of biological materials, and biological research, depend on the ability to elicit specific and high-level expression of genes encoding RNAs or proteins of therapeutic, commercial, or experimental value. Such gene expression is dependent on protein-DNA interactions.

Attempts have been made to change the specificity of DNA-binding proteins. Those attempts rely primarily on strategies involving mutagenesis of these proteins at sites expected to be important for DNA-recognition and often have been selected via phage display (see, for example, Rebar and Pabo, (1994) *Science* 263:671–673; Jamieson et al. (1994) *Biochemistry* 33:5689–5695; Suckow et al. (1994) *Nuc Acids Res* 22:2198–2208; Greisman and Pabo, (1997) *Science* 275:657–661). This strategy may not always be efficient or possible with some DNA-binding domains because of limitations imposed by their three-dimensional structure, mode of docking to DNA, or special requirements of phage display. In other cases it may not be sufficient to achieve important objectives discussed below. Therefore, it is desirable to have a strategy which can utilize many different DNA-binding domains and can combine them as required for DNA recognition and gene regulation.

In certain embodiments, the subject methods can be used to alter the DNA binding specificity of a known DNA binding protein. In other embodiments, the subject method can be used to generate novel composite DNA binding domains by combinatorially combining various motifs. The appended examples illustrate this aspect of the invention. The most widely used domain within protein transcription factors appears to be the zinc finger (Zf) motif. This is an independently folded zinc-containing mini-domain which can be used in a modular fashion to achieve sequence-specific recognition of DNA (see, for example, Klug (1993) *Gene* 135:83–92; Rebar and Pabo (1994), supra; Jamieson et al. (1994) *Biochemistry* 33:5689–5695; Choo et al. (1994) *PNAS* 91:11163–11167; Wu et al. (1995) *PNAS* 92: 344–348; Segal et al. (1999) *PNAS* 96: 2758–2763; Greisman and Pabo (1997), supra). Variants zinc fingers with new DNA binding specificities have been selected from large randomized libraries using phage display. Herein we show that our system can be used to isolate zinc finger variants from a large random library using our bacterial-based ITS.

In still other embodiments, the regulatory sequence can be provided in a combinatorial format, e.g., to provide a library of potential target DNA sequences. Those sequences which are bound by a DNA binding domain can be identified in the library.

For example, the method can be used to identify DNA-protein interactions by the steps of providing a host cell which contains a target gene encoding a growth selective marker or other selectable marker, operably linked to a target DNA sequence. The cell is also engineered to include a first chimeric gene which encodes a first fusion protein including (a) a first interacting domain, and (b) a test DNA binding domain. This also includes a second chimeric gene encoding a second fusion protein including (a) a second interacting domain that binds to the first interacting domain, and (b) an activation tag (such as a polymerase interaction domain) which activates transcription of the selective marker gene when localized in the vicinity of the target DNA sequence. One or both of the test DNA binding domains and/or the target DNA sequence are provided in the host cell populations as variegated libraries (with respect to sequence) to yield a library complexity of at least $10^7$ members. Cells in which interaction of a test DNA binding domain and a target DNA sequence occur can be selected and/or amplified based on the resulting growth trait conferred by the growth selective marker or based on cell sorting methods.

As described above, the ITS is set up with a bait fusion protein having a first interacting domain and a known or potential (test) DNA binding domain (DBD), e.g., a polypeptide which may specifically bind to a defined nucleotide sequence.

In embodiments wherein the target DNA sequence is being varied, the DBD portion of the bait fusion protein can be derived using all, or a DNA binding portion, of a transcriptional regulatory protein, e.g., of either a transcriptional activator or transcriptional repressor, which retains the ability to selectively bind to particular nucleotide sequences.

In embodiments wherein the system is derived with a variegated library of DNA binding domains, the DBDs can be, for example: a collection of naturally occurring DNA binding domains; a collection of mutagenized DNA binding domains, i.e., altered by point mutation, deletion or addition or randomized synthesis of relevant segments; or a collection of composite DNA binding domains derived from combinatorial assembly of various DNA binding elements or a randomized polypeptide sequence attached to other DNA binding modules.

The interacting domain can be any polypeptide sequence for which there is a known protein binding partner. It may be, for example, a dimerization or other oligomerization motif. Such a domain can be a constitutive oligomerization domain, or an inducible oligomerization domain, i.e., a domain mediating oligomerization only in the presence of a third molecule, such as a small organic molecule. Examples of constitutive oligomerization domains include leucine zippers.

Example of inducible oligomerization domains include FK506 and cyclosporin binding domains of FK506 binding proteins and cyclophilins, and the rapamycin binding domain of FRAP. Such inducible oligomerization domains are referred to herein as "ligand binding domains" and are further described herein under the section entitled accordingly.

A dimerization domain is defined herein as a sequence of amino acids capable of forming homodimers or heterodimers. One example of a dimerization domain is the leucine zipper (LZ) element. Leucine zippers have been identified, generally, as stretches of about 35 amino acids containing 4–5 leucine residues separated from each other by six amino acids (Maniatis and Abel (1989) Nature 341:24–25). Exemplary leucine zippers occur in a variety of eukaryotic DNA binding proteins, such as GCN4, C/EBP, c-Fos, c-Jun, c-Myc and c-Max. Other dimerization domains include helix-loop-helix domains (Murre, C. et al. (1989) *Cell* 58:537–544). Dimerization domains may also be selected from other proteins, such as the retinoic acid receptor, the thyroid hormone receptor or other nuclear hormone receptors (Kurokawa et al. (1993) Genes Dev. 7:1423–1435) or from the yeast transcription factors GAL4 and HAP1 (Marmonstein et al. (1992) Nature 356:408–414; Zhang et al. (1993) Proc. Natl. Acad. Sci. USA 90:2851–2855). Dimerization domains are further described in U.S. Pat. No. 5,624,818 by Eisenman.

In another embodiment, the oligomerization domain is a tetramerization domain. For example, the tetramerization domain is the *E. coli* lactose repressor tetramerization domain (amino acids 46–360; Chakerian et al. (1991) J.

Biol. Chem. 266:1371; Alberti et al. (1993) EMBO J. 12:3227; and Lewis et al. (1996) Nature 271:1247). Thus, the inclusion of a tetramerization domain in a transcriptional activator allows four activation domains to be complexed together and form a transcriptional activator complex. Furthermore, more than one activation unit can be linked to one tetramerization domain, to thereby form a transcriptional activator complex comprising more than 4 activation units.

In another embodiment, the tetramerization domain is that from a p53 protein. The p53 tetramerization domain maps to residues 322–355 of p53 (Wang et al. (1994) Mol. Cell. Biol. 14:5182; Clore et al. (1994) Science 265:386) and is further described in U.S. Pat. No. 5,573,925 by Halazonetis.

Other exemplary suitable tetramerization domains include artificial tetramerization domains, such as variants of the GCN4 leucine zipper that form tetramers (Alberti et al. (1993) EMBO J. 12:3227–3236; Harbury et al. (1993) Science 262:1401–1407; Krylov et al. (1994) EMBO J. 13:2849–2861). One of skill in the art could readily select alternate tetramerization domains. For example, the tetrameric variant of GCN4 leucine zipper described in Harbury et al. (1993), supra, has isoleucines at positions d of the coiled coil and leucines at positions a, in contrast to the original zipper which has leucines and valines, respectively.

In addition, the art also provides a variety of techniques for identifying other naturally occurring oligomerization domains, as well as oligomerization domains derived from mutant or otherwise artificial sequences. See, for example, Zeng et al. (1997) Gene 185:245; O'Shea et al. (1992) Cell 68:699–708; Krylov et al. [cited above].

In another embodiment, libraries of potential DNA binding domains are created from the assembly of DNA binding motifs from various transcription factors, e.g., resulting in DNA binding domains which may have novel DNA binding specificities. Such DNA binding domains, referred to herein as "composite DNA binding domains" can be designed to specifically recognize unique binding sites. For example, a DNA binding domain can be constructed that comprises DNA binding regions from a zinc finger protein and a homeobox protein.

The DNA sequences recognized by a chimeric protein containing a composite DNA-binding domain can be determined using the subject method, e.g., by library vs. library screening, or the proteins can be selected by their specificity toward a desired sequence. A desirable nucleic acid recognition sequence consists of a nucleotide sequence spanning at least ten, preferably eleven, and more preferably twelve or more bases. The component binding portions (putative or demonstrated) within the nucleotide sequence need not be fully contiguous; they may be interspersed with "spacer" base pairs that need not be directly contacted by the chimeric protein but rather impose proper spacing between the nucleic acid subsites recognized by each module. These sequences should not impart expression to linked genes when introduced into cells in the absence of the engineered DNA-binding protein.

In preferred embodiments, the subject method can be used to identify a nucleotide sequence that is recognized by a transcriptional activator protein containing a composite DNA-binding region, preferably recognized with high affinity and specificity, several methods can be used. For instance, high-affinity binding sites for the protein or protein complex can be selected from a large pool of random DNA sequences, and their sequences determined. From this collection of sequences, individual sequences with desirable characteristics (i.e., high affinity and specificity for composite protein, minimal affinity for individual subdomains) are selected for use. Alternatively, the collection of sequences is used to derive a consensus sequence that carries the favored base pairs at each position. Such a consensus sequence is synthesized and tested (see below) to confirm that it has an appropriate level of affinity and specificity.

An alternative approach to generating novel sequence specificities is to use databases of known homologs of the DBD to predict amino acid substitutions that will alter binding. For example, analysis of databases of zinc finger sequences has been used to alter the binding specificity of a zinc finger (Desjarlais and Berg (1993) Proc. Natl. Acad. Sci. USA 90, 2256–2260).

A further and powerful approach is random mutaganesis of amino acid residues which may contact the DNA, followed by screening or selection for the desired novel specificity. For example, phage display of the three fingers of Zif268 (including the two incorporated into ZFHID1) has been described, and random mutagenesis and selection has been used to alter the specificity and affinity of the fingers (Rebar and Pabo (1994) Science 263, 671–673; Jamieson et al, (1994) Biochemistry 33, 5689–5695; Choo and Klug (1994) Proc. Natl. Acad. Sci. USA 91, 11163–11167; Choo and Klug (1994) Proc. Natl. Acad. Sci. USA 91, 11168–11172; Choo et al (1994) Nature 372, 642–645; Wu et al (1995) Proc. Natl. Acad. Sci USA 92, 344–348). These mutants can be incorporated into ZFHD1 to provide new composite DNA binding regions with novel nucleotide sequence specificities. Other DBDs may be similarly altered. If structural information is not available, general mutagenesis strategies can be used to scan the entire domain for desirable mutations: for example alanine-scanning mutagenesis (Cunningham and Wells (1989) Science 244, 1081–1085), PCR misincorporation mutagenesis (see e.g. Cadwell and Joyce (1992) PCR Meth. Applic. 2, 28–33), and 'DNA shuffling' (Stemmer ref.); or by random mutagenesis (Miller et al. (1992) A Short Course in Bacterial Genetics, CSHL Press, Cold Spring Harbor, N.Y.; and Greener et al. (1994) Strategies in Mol Biol 7:32–34). These techniques produce libraries of random mutants, or sets of single mutants, that can then be readily searched by screening or selection approaches such as phage display.

In all these approaches, mutagenesis can be carried out directly on the DNA binding region, or on the individual subdomain of interest in its natural or other protein context. In the latter case, the engineered component domain with new nucleotide sequence specificity may be subsequently incorporated into the composite DNA binding region in place of the starting component. The new DNA binding specificity may be wholly or partially different from that of the initial protein: for example, if the desired binding specificity contains (a) subsite(s) for known DNA binding subdomains, other subdomains can be mutated to recognize adjacent sequences and then combined with the natural domain to yield a composite DNA binding region with the desired specificity.

Randomization and selection strategies may be used to incorporate other desirable properties into the composite DNA binding regions in addition to altered nucleotide recognition specificity, by imposing an appropriate in vitro selective pressure (for review see Clackson and Wells (1994) Trends Biotech. 12, 173–184). These include improved affinity, specificity, improved stability and improved resistance to proteolytic degradation.

As appropriate, the DNA binding motif used to generate the bait fusion protein can include oligomerization motifs. As known in the art, certain transcriptional regulators dimerize, with dimerization promoting cooperative binding of the two monomers to their cognate recognition elements.

The use of recombinant DNA techniques to create a fusion gene, with the translational product being the desired bait fusion protein, is well known in the art. Essentially, the joining of various DNA fragments coding for different polypeptide sequences is performed in accordance with conventional techniques, employing blunt-ended or stagger-ended termini for ligation, restriction enzyme digestion to provide for appropriate termini, filling in of cohesive ends as appropriate, alkaline phosphatase treatment to avoid undesirable joining, and enzymatic ligation. Alternatively, the fusion gene can be synthesized by conventional techniques including automated DNA synthesizers. In another method, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology*, Eds. Ausubel et al. John Wiley & Sons: 1992).

It may be necessary in some instances to introduce an unstructured polypeptide linker region between the DNA binding domain of the fusion protein and the bait polypeptide sequence. Where the bait fusion protein also includes dimerization sequences, it may be preferable to situate the linker between the dimerization sequences and the bait polypeptide. The linker can facilitate enhanced flexibility of the fusion protein allowing the DBD to freely interact with a responsive element, and, if present, the dimerization sequences to make inter-protein contacts. The linker can also reduce steric hindrance between the two fragments, and allow appropriate interaction of the bait polypeptide portion with a prey polypeptide component of the interaction trap system. The linker can also facilitate the appropriate folding of each fragment to occur. The linker can be of natural origin, such as a sequence determined to exist in random coil between two domains of a protein. An exemplary linker sequence is the linker found between the C-terminal and N-terminal domains of the RNA polymerase α subunit. Other examples of naturally occurring linkers include linkers found in the λcI and LexA proteins. Alternatively, the linker can be of synthetic origin. For instance, the sequence $(Gly_4Ser)_3$ can be used as a synthetic unstructured linker. Linkers of this type are described in Huston et al. (1988) PNAS 85:4879; and U.S. Pat. No. 5,091,513, both incorporated by reference herein.

A. Design of Composite DNA-binding Regions.

Each composite DNA-binding region consists of a continuous polypeptide region containing two or more component heterologous polypeptide portions which are individually capable of recognizing (i.e., binding to) specific nucleotide sequences. The individual component portions may be separated by a linker comprising one or more amino acid residues intended to permit the simultaneous contact of each component polypeptide portion with the DNA target. The combined action of the composite DNA-binding region formed by the component DNA-binding modules may result in the addition of the free energy decrement of each set of interactions. The effect is to achieve a DNA-protein interaction of very high affinity and specificity. This goal is often best achieved by combining component polypeptide regions that bind DNA poorly on their own, that is with low affinity, insufficient for functional recognition of DNA under typical conditions in a mammalian cell. Because the hybrid protein exhibits affinity for the composite site several orders of magnitude higher than the affinities of the individual subdomains for their subsites, the protein preferentially (preferably exclusively) occupies the "composite" site which typically comprises a nucleotide sequence spanning the individual DNA sequence recognized by the individual component polypeptide portions of the composite DNA-binding region.

Suitable component DNA-binding polypeptides for incorporation into a composite region have one or more, preferably more, of the following properties. They bind DNA as monomers, although dimers can be accommodated. They should have modest affinities for DNA, with dissociation constants preferably in the range of $10^{-6}$ to $10^{-9}$ M. They should optimally belong to a class of DNA-binding domains whose structure and interaction with DNA are well understood and therefore amenable to manipulation. For gene therapy applications, they are preferably derived from human proteins.

B. Examples of Suitable Component DNA-binding Domains.

DNA-binding domains with appropriate DNA binding properties may be selected from several different types of natural DNA-binding proteins. One class comprises proteins that normally bind DNA only in conjunction with auxiliary DNA-binding proteins, usually in a cooperative fashion, where both proteins contact DNA and each protein contacts the other. Examples of this class include the homeodomain proteins, many of which bind DNA with low affinity and poor specificity, but act with high levels of specificity in vivo due to interactions with partner DNA-binding proteins.

The homeodomain is a highly conserved DNA-binding domain which has been found in hundreds of transcription factors (Scott et al., *Biochim. Biophys. Acta* 989:25–48 (1989) and Rosenfeld, *Genes Dev.* 5:897–907 (1991)). The regulatory function of a homeodomain protein derives from the specificity of its interactions with DNA and presumably with components of the basic transcriptional machinery, such as RNA polymerase or accessory transcription factors (Laughon, *Biochenmistry* 30(48):11357 (1991)). A typical homeodomain comprises an approximately 61-amino acid residue polypeptide chain, folded into three alhpha helices which binds to DNA.

A second class comprises proteins in which the DNA-binding domain is comprised of multiple reiterated modules that cooperate to achieve high-affinity binding of DNA. An example is the $Cys_2His_2$ (SEQ ID NO: 4) class of zinc-finger proteins, which typically contain a tandem array of from two or three to dozens of zinc-finger modules. Each module contains an alpha-helix capable of contacting a three to five base-pair stretch of DNA. Typically, at least three zinc-fingers are required for high-affinity DNA binding. Therefore, one or two zinc-fingers constitute a low-affinity DNA-binding domain with suitable properties for use as a component in this invention. Examples of proteins of the C2H2 class include TFIIIA, Zif268, Gli, and SRE-ZBP. (These and other proteins and DNA sequences referred to herein are well known in the art. Their sources and sequences are known.)

The zinc finger motif, of the type first discovered in transcription factor IIIA (Miller et al., *EMBO J.* 4:1609 (1985)), offers an attractive framework for studies of transcription factors with novel DNA-binding specificities. The zinc finger is one of the most common eukaryotic DNA-binding motifs (Jacobs, *EMBO J.* 11:4507 (1992)), and this family of proteins can recognize a diverse set of DNA sequences (Pavletich and Pabo, *Science* 261:1701 (1993)). Crystallographic studies of the Zif268-DNA complex and other zinc finger-DNA complexes show that residues at four positions within each finger make most of the base contacts (with occassional contacts from two other positions), and there has been some discussion about rules that may explain zinc finger-DNA recognition (Desjarlais and Berg, *PNAS* 89:7345 (1992) and Klevit, *Science* 253:1367 (1991)). However, studies have also shown that zinc fingers can dock against DNA in a variety of ways (Pavletich and Pabo (1993) and Fairall et al., *Nature* 366:483 (1993)).

A third general class comprises proteins that themselves contain multiple independent DNA-binding domains. Often, any one of these domains is insufficient to mediate high-affinity DNA recognition, and cooperation with a covalently linked partner domain is required. Examples include the POU class, such as Oct-1, Oct-2 and Pit-1, which contain both a homeodomain and a POU-specific domain; HNF1 and certain Pax proteins (examples: Pax-3, Pax-6), which contain both a homeodomain and a paired box/domain.

From a structural perspective, DNA-binding proteins containing domains suitable for use as polypeptide components of a composite DNA-binding region may be classified as DNA-binding proteins with a helix-turn-helix structural design, including, but not limited to, MAT1, MAT 2, MAT a1, Antennapedia, Ultrabithorax, Engrailed, Paired, Fushi tarazu, HOX, Unc86, and the previously noted Oct1, Oct2 and Pit; zinc finger proteins, such as Zif268, SWI5, Krüppel and Hunchback; steroid receptors; DNA-binding proteins with the helix-loop-helix structural design, such as Daughterless, Achaete-scute (T3), MyoD, E12 and E47; and other helical motifs like the leucine-zipper, which includes GCN4, C/EBP, c-Fos/c-Jun and JunB. The amino acid sequences of the component DNA-binding domains may be naturally-occurring or non-naturally-occurring (or modified).

The choice of component DNA-binding domains may be influenced by a number of considerations, including the species, system and ultimately the cell type in which the optimized DBD is to be expressed; the feasibility of incorporation into a chimeric protein, as may be shown by modeling; and the desired application or utility. The choice of DNA-binding domains may also be influenced by the individual DNA sequence specificity of the domain and the ability of the domain to interact with other proteins or to be influenced by a particular cellular regulatory pathway. Preferably, the distance between domain termini is relatively short to facilitate use of the shortest possible linker or no linker. The DNA-binding domains can be isolated from a naturally-occurring protein, or may be a synthetic molecule based in whole or in part on a naturally-occurring domain.

An additional strategy for obtaining component DNA-binding domains using the subject method is to modify an existing DNA-binding domain to reduce its affinity for DNA into the appropriate range. For example, a homeodomain such as that derived from the human transcription factor Phox1, may be modified by substitution of the glutamine residue at position 50 of the homeodomain. Substitutions at this position remove or change an important point of contact between the protein and one or two base pairs of the 6-bp DNA sequence recognized by the protein. Thus, such substitutions reduce the free energy of binding and the affinity of the interaction with this sequence and may or may not simultaneously increase the affinity for other sequences. Such a reduction in affinity is sufficient to effectively eliminate occupancy of the natural target site by this protein when produced at typical levels in mammalian cells. But it would allow this domain to contribute binding energy to and therefore cooperate with a second linked DNA-binding domain. Other domains that amenable to this type of manipulation include the paired box, the zinc-finger class represented by steroid hormone receptors, the myb domain, and the ets domain.

C. Design of Linker Sequence for Covalently Linked Composite DBDs.

The continuous polypeptide span of the composite DNA-binding domain may contain the component polypeptide modules linked directly end-to-end or linked indirectly via an intervening amino acid or peptide linker. A linker moiety may be designed or selected empirically to permit the independent interaction of each component DNA-binding domain with DNA without steric interference. A linker may also be selected or designed so as to impose specific spacing and orientation on the DNA-binding domains. The linker amino acids may be derived from endogenous flanking peptide sequence of the component domains or may comprise one or more heterologous amino acids. Linkers may be designed by modeling or identified by experimental trial.

The linker may be any amino acid sequence that results in linkage of the component domains such that they retain the ability to bind their respective nucleotide sequences. In some embodiments it is preferable that the design involve an arrangement of domains which requires the linker to span a relatively short distance, preferably less than about 10 Å. However, in certain embodiments, depending upon the selected DNA-binding domains and the configuration, the linker may span a distance of up to about 50 Å. For instance, the ZFHD1 protein contains a glycine-glycine-arginine-arginine linker which joins the carboxyl-terminal region of zinc finger 2 to the amino-terminal region of the Oct-1 homeodomain.

Within the linker, the amino acid sequence may be varied based on the preferred characteristics of the linker as determined empirically or as revealed by modeling. For instance, in addition to a desired length, modeling studies may show that side groups of certain nucleotides or amino acids may interfere with binding of the protein. The primary criterion is that the linker join the DNA-binding domains in such a manner that they retain their ability to bind their respective DNA sequences, and thus a linker which interferes with this ability is undesirable. A desirable linker should also be able to constrain the relative three-dimensional positioning of the domains so that only certain composite sites are recognized by the chimeric protein. Other considerations in choosing the linker include flexibility of the linker, charge of the linker and selected binding domains, and presence of some amino acids of the linker in the naturally-occurring domains. The linker can also be designed such that residues in the linker contact DNA, thereby influencing binding affinity or specificity, or to interact with other proteins. For example, a linker may contain an amino acid sequence which can be recognized by a protease so that the activity of the chimeric protein could be regulated by cleavage. In some cases, particularly when it is necessary to span a longer distance between the two DNA-binding domains or when the domains must be held in a particular configuration, the linker may optionally contain an additional folded domain.

D. Additional Domains.

Additional domains may be included in the various chimeric proteins of this invention, e.g., a nuclear localization sequence, a transcription regulatory domain, a ligand binding domain, a protein-binding domain, a domain capable of cleaving a nucleic acid, etc.

For example, in some embodiments the chimeric proteins will contain a cellular targeting sequence which provides for the protein to be translocated to the nucleus. Typically a nuclear localization sequence has a plurality of basic amino acids, referred to as a bipartite basic repeat (reviewed in Garcia-Bustos et al, Biochimica et Biophysica Acta (1991) 1071, 83–101). This sequence can appear in any portion of the molecule internal or proximal to the N- or C-terminus and results in the chimeric protein being localized inside the nucleus.

DNA sequences encoding individual DNA-binding subdomains and linkers, if any, are joined such that they constitute a single open reading frame encoding a chimeric protein containing the composite DNA-binding region and capable of being translated into a single polypeptide harboring all component domains. This protein-encoding DNA sequence is then placed into a conventional plasmid vector that directs the expression of the protein in the appropriate cell type. For testing of proteins and determination of binding specificity and affinity, it may be desirable to construct plasmids that direct the expression of the protein in bacteria or in reticulocyte-lysate systems. For use in the production of proteins in mammalian cells, the protein-encoding sequence is introduced into an expression vector that directs expression in these cells. Expression vectors suitable for such uses are well known in the art. Various sorts of such vectors are commercially available.

The ability to engineer binding regions with novel DNA binding specificities permits composite DNA binding regions to be designed and produced to interact specifically with any desired nucleotide sequence. Thus a clinically interesting sequence may be chosen and a composite DNA binding region engineered to recognize it. For example, composite DNA binding region may be designed to bind chromosomal breakpoints and repress transcription of an otherwise activated oncogene (see Choo et al (1994) Nature 372, 642–645); to bind viral DNA or RNA genomes and block or activate expression of key viral genes; or to specifically bind the common mutated versions of a mutational hotspot sequence in an oncogene and repress transcription (such as the mutation of codon 21 of human ras), and analogously to bind mutated tumor supressor genes and activate their transcription.

Additionally, in optimizing chimeric proteins of this invention it should be appreciated that immunogenicity of a polypeptide sequence is thought to require the binding of peptides by MHC proteins and the recognition of the presented peptides as foreign by endogenous T-cell receptors. It may be preferable, at least in gene therapy applications, to alter a given foreign peptide sequence to minimize the probability of its being presented in humans. For example, peptide binding to human MHC class I molecules has strict requirements for certain residues at key 'anchor' positions in the bound peptide: e.g. HLA-A2 requires leucine, methionine or isoleucine at position 2 and leucine or valine at the C-terminus (for review see Stern and Wiley (1994) Structure 2, 145–251). Thus in engineered proteins, this periodicity of these residues could be avoided.

VIII. Host cells

Host cells which may be used in accord with the various embodiments of the invention include prokaryotes and eukaryotes.

Exemplary eukaryotic host cells include yeast and mammalian cells.

Exemplary prokaryotic host cells are gram-negative bacteria such as *Escherichia coli*, or gram-positive bacteria such as *Bacillus subtilis*.

Recognized prokaryotic hosts include bacterial strains of *Escherichia, Bacillus, Streptomyces, Pseudomonas, Salmonella, Serratia, Streptococcus, Lactobacillus, Enterococcus, Shigella*, and the like. In preferred embodiments, the prokaryotic host is compatible with the replicon and control sequences in the expression plasmid.

Preferred prokaryotic host cells for use in carrying out the present invention are strains of the bacteria Escherichia, although Bacillus and other genera are also useful. Techniques for transforming these hosts and expressing foreign genes cloned in them are well known in the art (see e.g., Maniatis et al. and Sambrook et al., ibid.). Vectors used for expressing foreign genes in bacterial hosts will generally contain a selectable marker, such as a gene for antibiotic resistance, and a promoter which functions in the host cell. Appropriate promoters include trp (Nicholset al. (1983) *Meth. Enzymol.* 101:155–164), lac (Casadaban et al. (1980) *J. Bacteriol.* 143:971–980), and phage lambda promoter systems (Queen (1983) *J. Mol. Appl. Genet.* 2:1–10). Plasmids useful for transforming bacteria include pBR322 (Bolivar et al. (1977) *Gene* 2:95–113), the pUC plasmids (Messing (1983) *Meth. Enzymol.* 101:20–77), Vieira and Messing (1982) *Gene* 19:259–268), pCQV2 (Queen, supra), pACYC plasmids (Chang et al. (1978) *J Bacteriol* 134:1141), pRW plasmids (Lodge et al. (1992) *FEMS Microbiol Lett* 95:271), and derivatives thereof.

The choice of appropriate host cell will also be influenced by the choice of detection signal. For instance, the choice of cell can be influenced by the desire to use a reporter construct which encodes a particular direct FACS tag or indirect FACS tag. The reporter gene may be a host cell gene that has been operably linked to a "bait-responsive" promoter. Alternatively, it may be a heterologous gene that has been so linked. Suitable genes and promoters are discussed above. Accordingly, it will be understood that to achieve selection or screening by FACS, the host cell must have an appropriate phenotype so that expression of the reporter provides a statistically significant difference in fluorescence relative to the host cell without the reporter gene product.

IX. Exemplary Uses of the Interaction Trap Systems

Protein-Protein Interactions

The interaction trap systems of the present invention can be used, inter alia, for identifying protein-protein interactions, e.g., for generating protein linkage maps, for identifying therapeutic targets, and/or for general cloning strategies. As described above, the ITS can be derived with a cDNA library to produce a variegated array of bait or prey proteins which can be screened for interaction with, for example, a known protein expressed as the corresponding fusion protein in the ITS. In other embodiments, both the bait and prey proteins can be derived to each provide variegated libraries of polypeptide sequences. One or both libraries can be generated by random or semi-random mutagenesis. For example, random libraries of polypeptide sequences can be "crossed" with one another by simultaneous expression in the subject assay. Such embodiments can be used to identify novel interacting pairs of polypeptides.

Alternatively, the subject ITS can be used to map residues of a protein involved in a known protein-protein interaction. Thus, for example, various forms of mutagenesis can be utilized to generate a combinatorial library of either bait or prey polypeptides, and the ability of the corresponding fusion protein to function in the ITS can be assayed. Mutations which result in diminished (or potentiated) binding between the bait and prey fusion proteins can be detected by the level of reporter gene activity. For example, mutants of a particular protein which alter interaction of that protein with another protein can be generated and isolated from a library created, for example, by alanine scanning mutagenesis and the like (Ruf et al., (1994) Biochemistry 33:1565–1572; Wang et al., (1994) J. Biol. Chem. 269: 3095–3099; Balint et al., (1993) Gene 137:109–118; Grodberg et al., (1993) Eur. J. Biochem. 218:597–601; Nagashima et al., (1993) J. Biol. Chem. 268:2888–2892; Lowman et al., (1991) Biochemistry 30:10832–10838; and Cunningham et al., (1989) Science 244:1081–1085), by linker scanning mutagenesis (Gustin et al., (1993) Virology 193:653–660; Brown et al., (1992) Mol. Cell Biol. 12:2644–2652; McKnight et al., (1982) Science 232:316); by saturation mutagenesis (Meyers et al., (1986) Science 232:613); by PCR mutagenesis (Leung et al., (1989) Method Cell Mol Biol 1:11–19); or by random mutagenesis (Miller et al., (1992) A Short Course in Bacterial Genetics, CSHL Press, Cold Spring Harbor, N.Y.; and Greener et al., (1994) Strategies in Mol Biol 7:32–34). Linker scanning mutagenesis, particularly in a combinatorial setting, is an attractive method for identifying truncated (bioactive) forms of a protein, e.g., to establish binding domains.

In other aspects, the ITS can be designed for the isolation of genes encoding proteins which physically interact with a protein/drug complex. The method relies on detecting the reconstitution of a transcriptional activator in the presence of the drug. If the bait and prey fusion proteins are able to interact in a drug-dependent manner, the interaction may be detected by reporter gene expression.

Assays

Another aspect of the present invention relates to the use of the interaction trap systems in the development of assays which can be used to screen for drugs which are either agonists or antagonists of a protein-protein interaction of therapeutic consequence (U.S. Pat. No. 6,200,759). In a general sense, the assay evaluates the ability of a compound to modulate binding between the bait and prey polypeptides. Exemplary compounds which can be screened include peptides, nucleic acids, carbohydrates, small organic molecules, and natural product extract libraries, such as isolated from animals, plants, fungus and/or microbes.

In many drug screening programs which test libraries of compounds and natural extracts, high throughput assays are desirable in order to maximize the number of compounds surveyed in a given period of time. The subject ITS-derived screening assays can be carried out in such a format, and accordingly may be used as a "primary" screen. Accordingly, in an exemplary screening assay of the present invention, an ITS is generated to include specific bait and prey fusion proteins known to interact, and compound(s) of interest. Detection and quantification of reporter gene expression provides a means for determining a compound's efficacy at inhibiting (or potentiating) interaction between the bait and prey polypeptides. In certain embodiments, the approximate efficacy of the compound can be assessed by generating dose response curves from reporter gene expression data obtained using various concentrations of the test compound. Moreover, a control assay can also be performed to provide a baseline for comparison. In the control assay, expression of the reporter gene is quantitated in the absence of the test compound.

In another exemplary embodiment, a therapeutic target devised as the bait-prey complex is expressed in the same cell with a peptide library with the goal of identifying peptides which potentiate or inhibit the bait-prey interaction. Many techniques are known in the art for expressing peptide libraries intracellularly. In one embodiment, the peptide library is provided as part of a chimeric thioredoxin protein, e.g., expressed as part of the active loop.

In yet another embodiment, the interaction trap systems of the invention can be generated in the form of a diagnostic assay to detect the interaction of two proteins, e.g., where the gene from one is isolated from a biopsied cell. For instance, there are many instances where it is desirable to detect mutants which, while expressed at appreciable levels in the cell, are defective at binding other cellular proteins. Such mutants may arise, for example, from fine mutations, e.g., point mutants, which may be impractical to detect by the diagnostic DNA sequencing techniques or by the immunoassays. The present invention accordingly further contemplates diagnostic screening assays which generally comprise cloning one or more cDNAs from a sample of cells, and expressing the cloned gene(s) as part of an ITS under conditions which permit detection of an interaction between that recombinant gene product and a target protein. Accordingly, the present invention provides a convenient method for diagnostically detecting mutations to genes encoding proteins which are unable to physically interact with a "target" protein, which method relies on detecting the expression of the reporter gene in a bait/prey-dependent fashion as described above.

Protein-DNA Interactions

As described in more detail above, in certain embodiments, the various interaction trap systems of the invention can be used to identify or optimize DNA-protein interactions. For example, the subject method can be used to identify mutant or composite DNA binding domains having desired sequence binding preferences. It can also be used to identify DNA sequences which are selectively bound by a given DNA binding protein and/or to determine the sequence specificity of a DNA binding protein.

Protein-RNA Interactions

In another aspect, the present invention provides a method of detecting protein-RNA interactions (U.S. Pat. No. 5,750,667). The method begins with a host cell that contains a reporter gene expressing a detectable protein. The reporter gene is activated by an amino acid sequence including a transcriptional activation domain when the transcriptional activation domain is in sufficient proximity to the reporter gene.

The host cell also contains three different chimeric genes. The first chimeric gene is capable of being expressed in the host cell and encodes a first hybrid protein. The first hybrid protein comprises a DNA-binding domain that recognizes a binding site on the reporter gene in the host cell and a first RNA-binding domain. (When we refer to an RNA-binding "domain", we mean an amino acid sequence that is capable of binding an RNA molecule. This domain may be a fragment of a larger protein or may comprise an entire protein.)

The second chimeric gene is also capable of being expressed in the host cell and comprises a DNA sequence that encodes a second hybrid protein. The second hybrid protein comprises a transcriptional activation domain and a second RNA-binding domain.

The third chimeric gene is capable of being transcribed to generate a hybrid RNA in the host cell. The hybrid RNA comprises a first RNA sequence capable of binding to either the first or second RNA-binding domain and a second RNA sequence to be tested for interaction with the RNA-binding domain that is not bound to the first RNA sequence. Interaction between both the first RNA-binding domain and the hybrid RNA and the second RNA-binding domain and the hybrid RNA causes the transcriptional activation domain to activate transcription of the reporter gene.

After subjecting the host cell to conditions under which the first hybrid protein, the second hybrid protein, and the hybrid RNA are expressed in sufficient quantity for the reporter gene to be activated, one determines whether the reporter gene has been expressed to a degree greater than expression in the absence of an interaction between both the first RNA-binding protein and the hybrid RNA and the second RNA-binding protein and the hybrid RNA. If the reporter gene has been expressed to a greater degree, this indicates that an RNA-protein interaction has taken place.

In various embodiments, either one of the RNA-binding proteins or either the first or second sequence of the hybrid RNA may be tested. One might have a specific RNA-binding protein and determine which of many different RNA sequences bound to the protein, or one might have a particular RNA sequence and determine which of many RNA-binding proteins bound to that specific RNA sequence. A multiplicity of proteins can be simultaneously tested to determine whether any interact with a known RNA molecule. Similarly, a multiplicity of RNAs can be simultaneously tested to determine whether any interact with a known RNA-binding protein.

Identification of Novel Transcription Factors Using a Random Test Polypeptide

Figure 13:
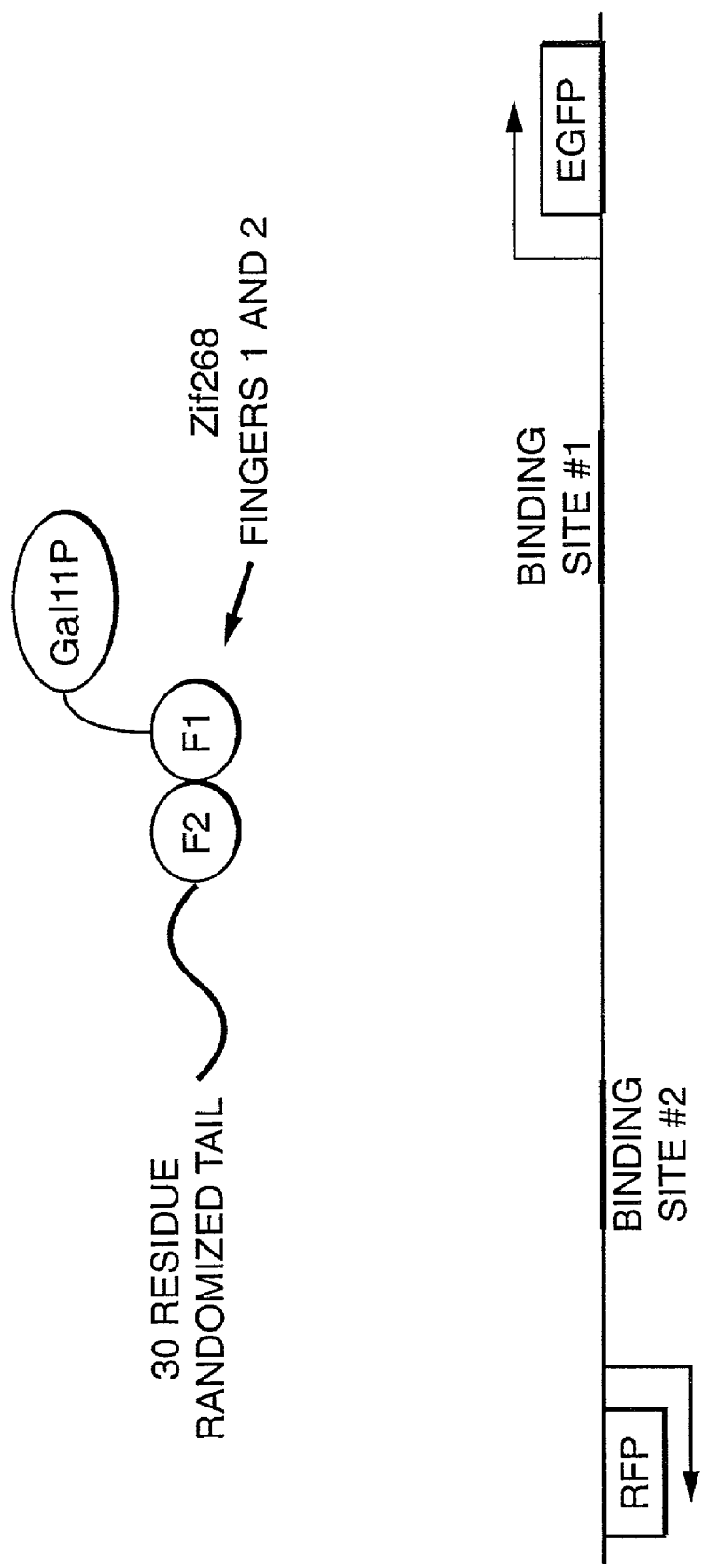
FIG. 13. This figure shows a certain embodiment of the subject ITS wherein a novel DNA binding domain may be identified from a library of random polyptides fused to one or more weak DNA binding domains.
Figure 14:
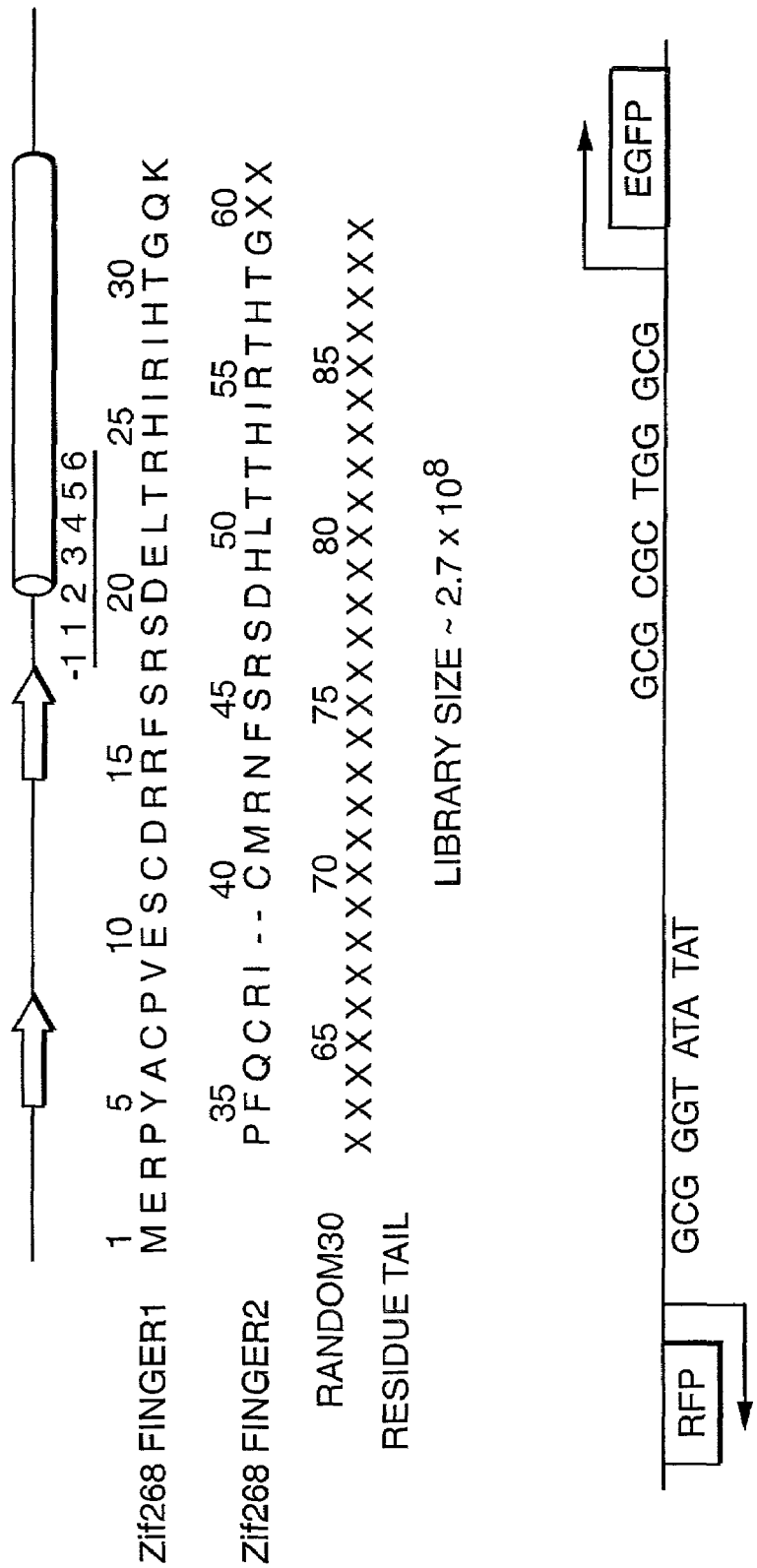
FIG. 14. This figure shows the result of a certain embodiment of the ITS for isolation of a novel DNA binding domain from a library of random polypeptides wherein the polypeptide does not bind to the promoter region of either reporter gene. (SEQ ID NOS: 95–97, respectively, in order of appearance).

In another aspect of the invention, the interaction trap system may be used to identify novel DNA binding domains using a chimeric transcription factor containing one or more weak DNA binding domain(s) fused to a random test polypeptide (FIG. 13). The reporter gene construct is fused to a promoter containing a binding site(s) for the weak DNA binding domain(s) and a target site to be tested for interaction with the random test polypeptide. Binding of the weak DNA binding domain to its recognition site in the promoter does not stimulate transcription, or only stimulates minimal transcription, on its own (FIG. 14). However, if the random test polypeptide fused to the weak DNA binding domain(s) recognizes the target DNA site adjacent to the weak DNA binding domain(s) recognition site(s), then transcription of the reporter gene will be stimulated. For example, a random test polypeptide may be fused to a DNA binding domain comprising two zinc fingers. The zinc fingers alone are not able to stimulate a significant amount of transcription of the reporter gene, however, binding of the random test polypeptide to a target DNA sequence in the promoter will significantly increase the level of reporter expression. In one embodiment, the invention may be used to select a novel polypeptide capable of binding to a DNA sequence of interest. Alternatively, it may be used in a cross-library screen to identify a novel polypeptide sequence capable of binding to a novel DNA sequence (e.g., cross a library of random test polypeptides with a library of target DNA sites).

Figure 10:
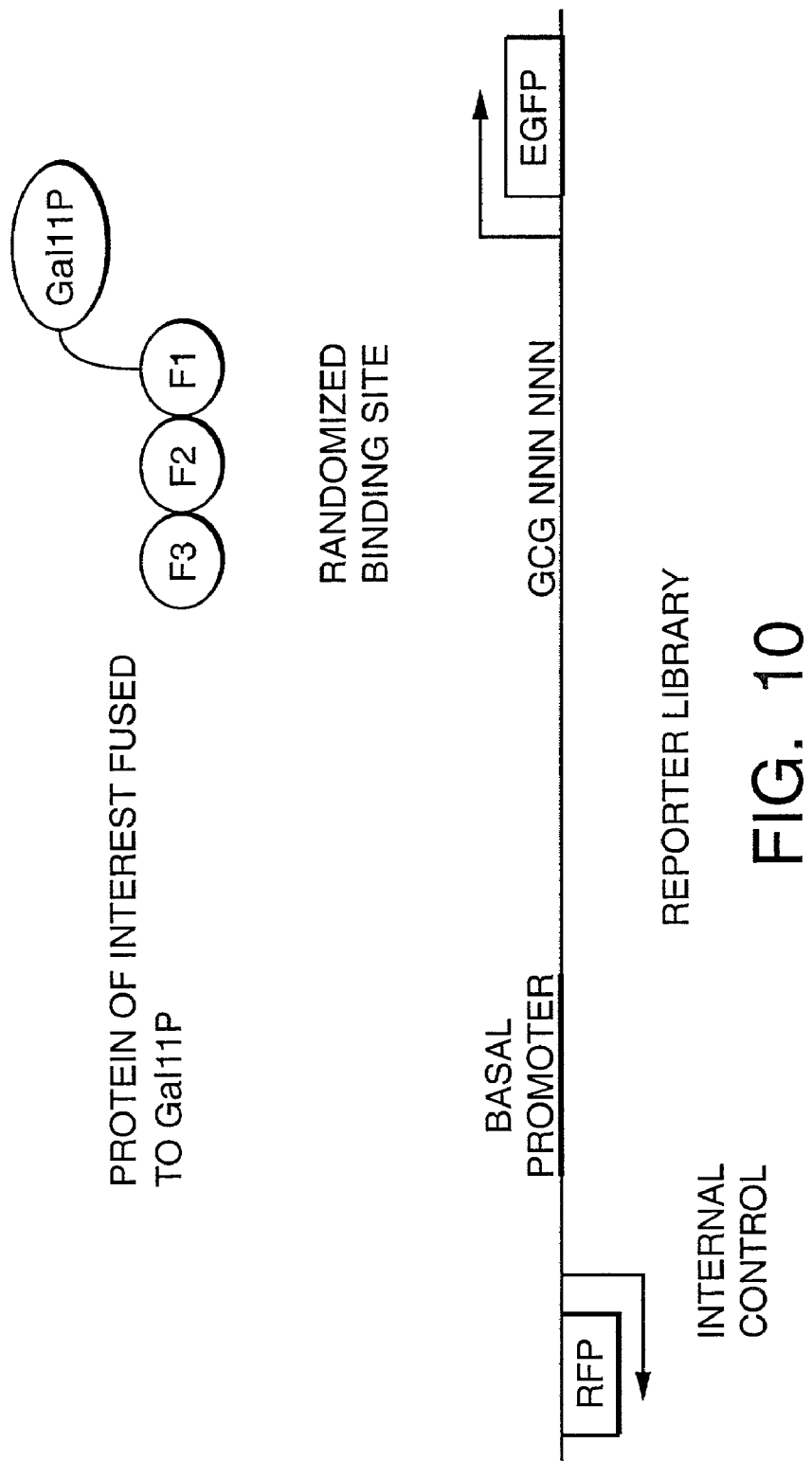
FIG. 10. This figure shows a certain embodiment of the subject ITS wherein a reporter gene under the control of a basal promoter is used to identify false positives arising from amplification of the reporter gene construct. (SEQ ID NO: 92).
Figure 15:
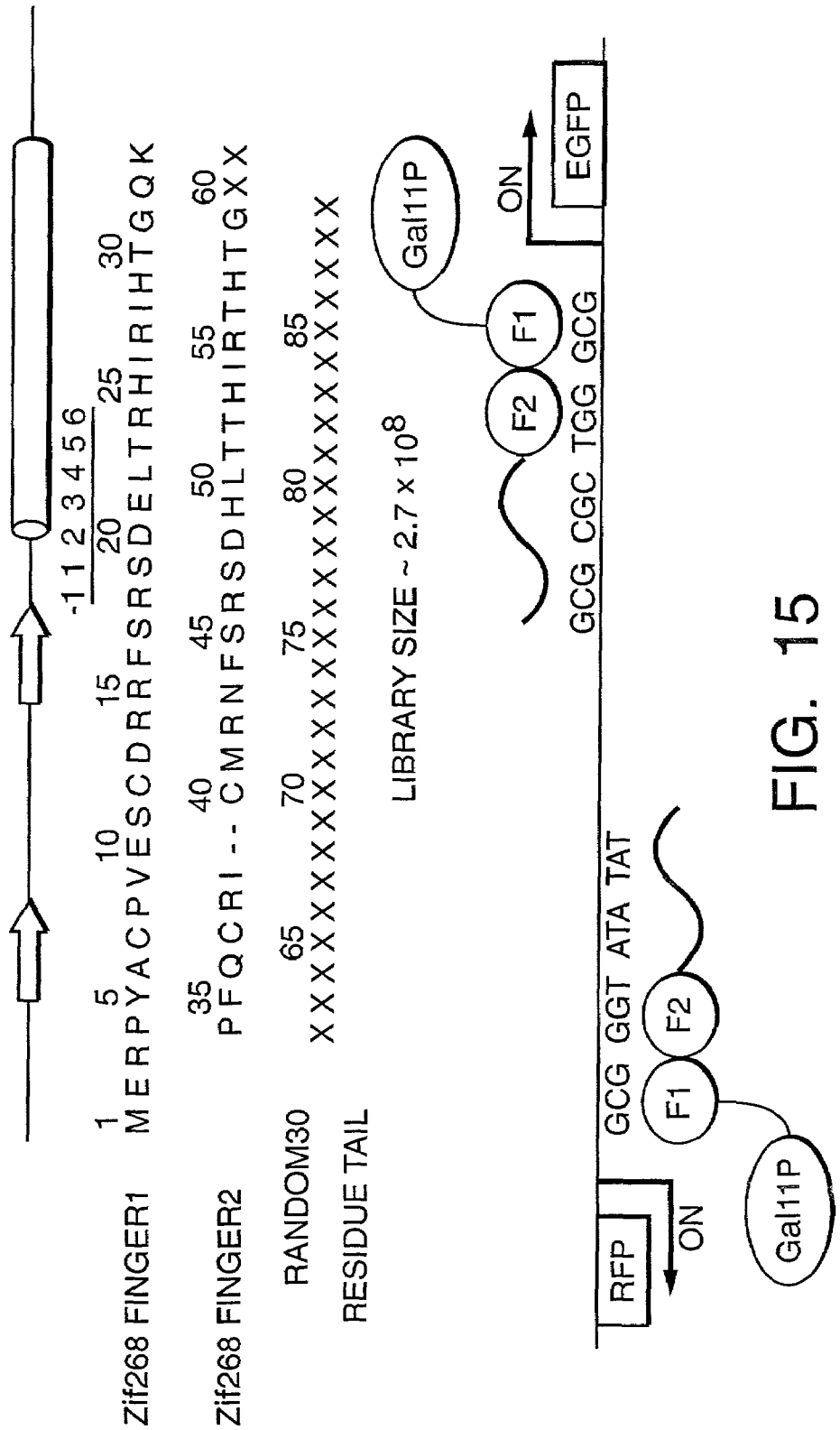
FIG. 15. This figure shows the result of a certain embodiment of the ITS for isolation of a novel DNA binding domain from a library of random polypeptides wherein the polypeptide non-specifically binds to the promoter region of both reporter genes. (SEQ ID NOS: 95–97, respectively, in order of appearance).
Figure 16:
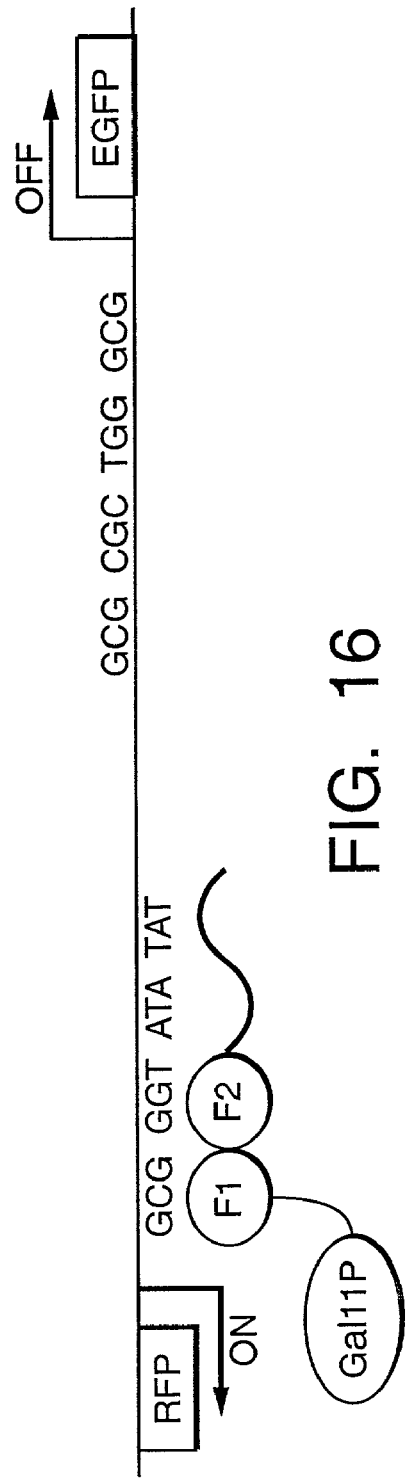
FIG. 16. This figure shows the result of a certain embodiment of the ITS for isolation of a novel DNA binding domain from a library of random polypeptides wherein the polypeptide specifically binds to the promoter region of one of the reporter genes. (SEQ ID NOS: 95–97, respectively, in order of appearance).
Figure 17:
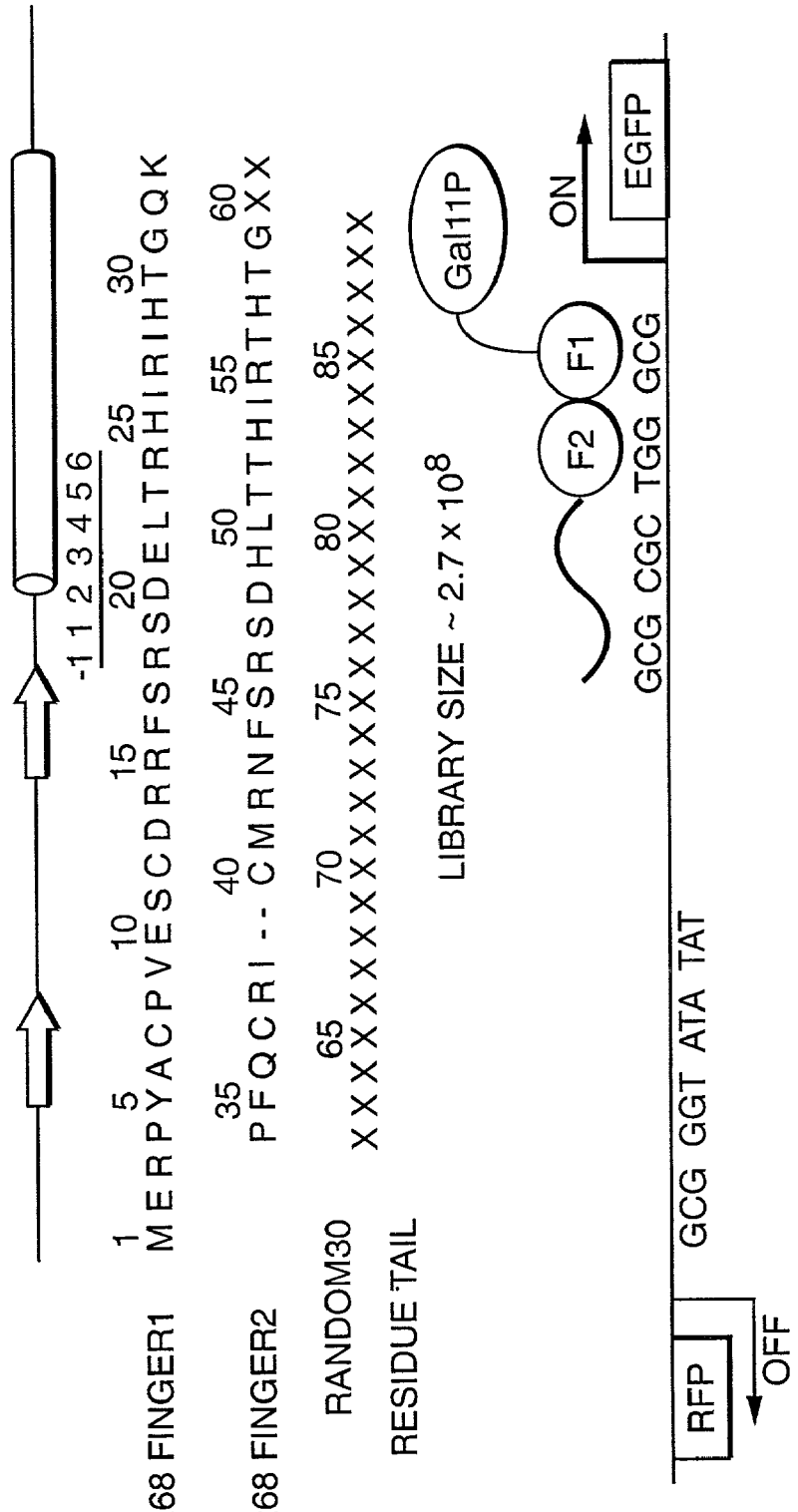
FIG. 17. This figure shows the alternative result the ITS embodiment shown in FIG. 16, wherein the polypeptide specifically binds to the promoter region of the other reporter gene. (SEQ ID NOS: 95–97, respectively, in order of appearance).

Highly charged polypeptides may be able to activate transcription of the reporter through non-specific binding to the DNA (FIG. 15). Such false positives may be reduced by utilizing a host cell with two different reporter genes driven by promoters containing either a specific or a non-specific target site. If the test polypeptide non-specifically binds to DNA due to a highly charged nature, then both of the reporter genes should be activated to a similar level upon exposure to the chimeric transcription factor. However, if the random test polypeptide specifically recognizes a target sequence, then transcription of one of the reporter genes should be activated to a much greater extent than the other (FIGS. 16 and 17). The two reporter gene system will also help to eliminate false positives arising from an increase in reporter gene expression occurring independently of transcription factor binding (e.g., an increase in the copy number of the reporter gene) (FIG. 10).

In certain embodiments the random test polypeptide may be from 10 to 100 amino acids in length, from 20 to 60 amino acids in length, from 25 to 50 amino acids in length, or from 30 to 40 amino acids in length. The polypeptide may be attached to the N-terminus or C-terminus of the weak DNA binding domain(s). Alternatively, the random test polypeptide may be internal to the weak DNA binding domain(s) portion of the molecule. When internal to the weak DNA binding domain(s), the random test polypeptide should not disrupt the ability of the weak interactor to bind to the appropriate DNA sequence. For example, the random test polypeptide may be inserted between two zinc finger domains without disrupting the ability of each zinc finger to bind its recognition sequence. The random test polypeptide may be fused directly onto the weak DNA binding domain(s) or may be separated from this portion by a linker molecule.

In various embodiments, the polypeptide may be completely random (e.g., randomized at all positions) or may be partially randomized (e.g., randomized at only a subset of the positions within the sequence). Further, it is possible to start with a known DNA binding domain or protein containing a DNA binding domain and alter one or more positions within the sequence to alter the DNA binding characteristics of the peptide or protein.

In certain embodiments, the target sequence to be tested for interaction with the random test polypeptide, may be directly adjacent to the recognition site for the weak DNA binding domain (e.g., the sequences are contiguous) or they may be non-contiguous (e.g., the recognition site and the target site are separated by an additional sequences). The random test polypeptide may recognize the target sequence on either strand of the DNA and may bind in either the major or minor groove. In various embodiments, the target sequence may be from 2 to 100, 2 to 50, 2 to 30, 2 to 20, or 2 to 10 nucleotides in length.

Identification of Dimerizing polypeptides

Figure 11:
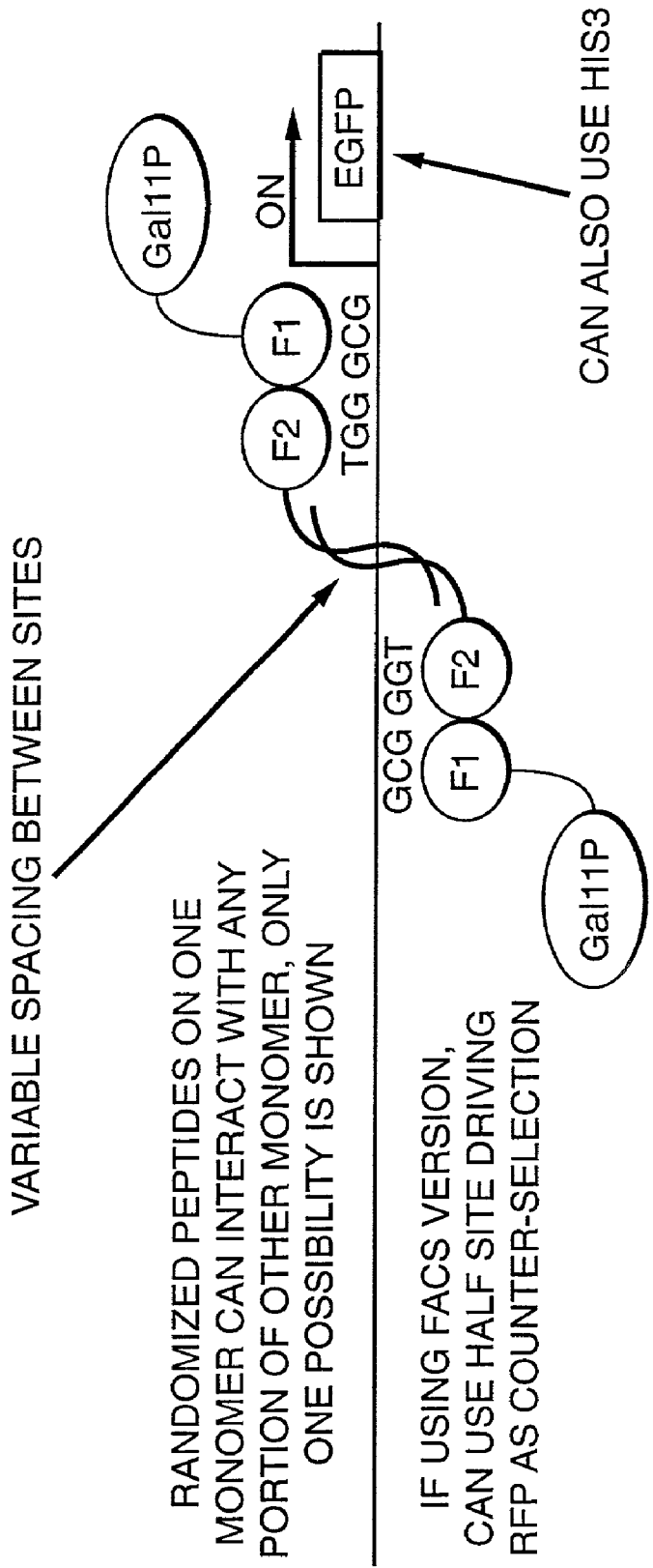
FIG. 11. This figure shows a certain embodiment of the subject ITS wherein protein dimerization may be detected. (SEQ ID NO: 93).

In another aspect, the interaction trap system of the present invention can be used to identify polypeptides capable of dimerizing (FIG. 11). A chimeric transcription factor containing one or more DNA binding domains is fused to a library of random test peptides. The reporter gene is fused to a promoter containing two repeats of the binding site for the transcription factor. Binding of a single copy of the transcription factor to the promoter is unable to induce a significant amount of transcription of the reporter gene. However, upon dimerization of the transcription factor leading to two copies being bound to the promoter region, transcription of the reporter gene is significantly increased. A diagram of an exemplary embodiment of this aspect of the invention is shown in FIG. 11, wherein the transcription factor is shown as a fusion between two zinc fingers and a random test polypeptide and the reporter gene is green fluorescent protein. As described above, a variety of transcription factors and reporter genes (either selectable or detectable) may be used in accordance with all embodiments of this aspect of the invention.

In various embodiments, the dimerization might occur due to an interaction between the random test polypeptide portion of the transcription factor molecules. Alternatively, the dimerization could be driven by an interaction between the random test polypeptide of one copy of the transcription factor and the DNA binding domain of the other copy of the transcription factor.

Identification of Composite Transcription Factors

Figure 12:
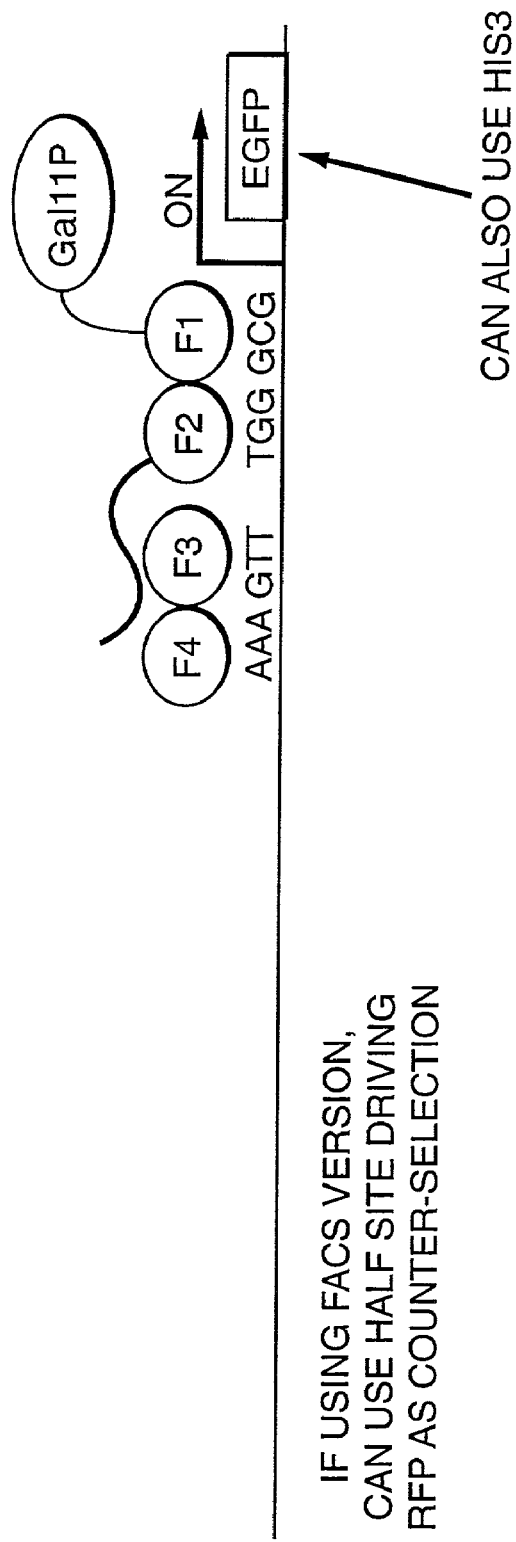
FIG. 12. This figure shows another embodiment of the subject ITS wherein protein dimerization may be detected. (SEQ ID NO: 94).

In another embodiment, the host cell contains a DNA binding domain polypeptide of known specificity which is tested for interaction with the library of chimeric fusion proteins comprising a randomized test polypeptide. An exemplary embodiment is shown in FIG. 12, wherein a DNA binding domain polypeptide of known specificity comprising two zinc fingers (ZF3 and ZF4) is tested for interaction with the library of fusion proteins comprising two zinc fingers (ZF1 and ZF2) and a random test polypeptide. Neither protein alone is able to stimulate a significant amount of reporter gene transcription, however, interaction between the two proteins will result in a desired level of reporter gene expression.

Use of a Monitoring Reporter to Identify False Positives

In this embodiment, a host cell is constructed which comprises a reporter gene placed under the control of a basal promoter and a binding site for a transcription factor with known specificity is operably linked to a reporter gene. Expression of the reporter gene may be used as a means of identifying false positives which have arisen due to an increase in the copy number of the reporter plasmid. For example, the host ITS can include a first reporter gene under the transcriptional control of a DBD recognition element which is being tested for interaction with the test polypeptide ("test reporter") and a second reporter gene under the control of a basal promoter ("monitoring reporter"). A basal, or weak, promoter is one which drives a basal level of expression of the reporter gene. An increase in the copy number of the reporter construct will produce an increase in the number of copies of the reporter gene being expressed at the basal level. Thus, an overall increase in the level of expression of the reporter gene will be detected (e.g., it will be viewed as a positive signal). However, the increase in expression is not due to a specific interaction between the test polypeptide and the DBD recognition element and thus is a false positive. Use of the monitoring reporter being expressed at a basal level may be used to identify such false positives by comparing the level of expression of the monitoring reporter to that of the test reporter. A similar increase in the levels of expression of the monitoring and test reporters will indicate a false positive whereas a greater increase of expression of the test reporter as compared to the monitoring reporter will indicate a true positive. A diagram of an exemplary embodiment of this aspect of the invention is shown in FIG. 10.

In an exemplary embodiment, the transcriptional regulatory sequence of the test reporter comprises a DBD recognition element for a weak DBD protein and a test polypeptide whereas the transcriptional regulatory sequence of the monitoring reporter comprises a DBD recognition element only for the weak DBD protein. Binding of the weak DBD protein to the DBD recognition element of the monitoring reporter will produce only a basal level of transcription. However, specific interaction of a fusion protein comprising a test polypeptide and a weak DBD protein with the recognition element of the test reporter will specifically increase the level of the test reporter as compared to the monitoring reporter.

In one embodiment of the invention, the test polypeptide may be a member of a library of polypeptides which is being tested for interaction with a fixed DBD recognition element. Alternatively, a fixed test polypeptide may be tested for interaction with a library of DBD recognition elements. Also within the scope of the invention would be testing for interactions in a cross library screen of test polypeptide and DBD recognition element libraries. Use of a monitoring reporter will be useful for identification of false positives in each of these circumstance.

Kits

In still other embodiments, the methods of the present invention, as described above, may be practiced using a kit for detecting an interaction between two proteins or a protein and a nucleic acid sequence.

In an illustrative embodiment, a kit for detecting a protein-protein interaction includes two vectors, a host cell, and (optionally) a set of primers for cloning one or more genes encoding sample proteins from a patient sample. The first vector may contain a promoter, a transcription termination signal, and other transcription and translation signals functionally associated with the first chimeric gene in order to direct the expression of the first chimeric gene. The first chimeric gene includes a DNA sequence that encodes a DNA-binding domain and a unique restriction site(s) for inserting a DNA sequence encoding either the target or sample protein, or a fragment thereof, in such a manner that the cloned sequence is expressed as part of a hybrid protein with the DNA-binding domain. The first vector also includes a means for replicating itself (e.g., an origin of replication) in the host cell. In preferred embodiments, the first vector also includes a first marker gene, the expression of which in the host cell permits selection of cells containing the first marker gene from cells that do not contain the first marker gene. Preferably, the first vector is a plasmid, though it may optionally be genomically integrated where the chimeric gene encodes the target protein.

The kit also includes a second vector which contains a second chimeric gene. The second chimeric gene also includes a promoter and other relevant transcription and translation sequences to direct expression of a second chimeric protein. The second chimeric gene includes a DNA sequence that encodes an activation tag and a unique restriction site(s) to insert a DNA sequence encoding either the target or sample protein (whichever is not cloned into the first chimeric gene), in such a manner that the cloned protein is capable of being expressed as part of a fusion protein with the activation tag. Again, as appropriate, the second vector can be genomically integrated.

In general, the kit will also be provided with one of the two vectors already including the target protein.

Accordingly in using the kit, the interaction of the target protein and the sample protein in the host cell causes a measurably greater expression of the reporter gene than when the DNA-binding domain and the activation tag are present in the absence of an interaction between the two fusion proteins. The cells containing the two hybrid proteins are incubated in/on an appropriate medium and the cells are monitored for the measurable activity of the gene product of the reporter construct. A positive test for this activity is an indication that the target protein and the sample protein have interacted. Such interaction brings their respective DNA-binding domain and activation tag into sufficiently close proximity to cause efficient transcription of the reporter gene.

As discussed in more detail above, a similar kit for detecting polypeptide-nucleic acid interactions is also encompassed in the invention.

Exemplification

The invention, now being generally described, will be more readily understood by reference to the following examples, which are included merely for purposes of illustration of certain aspects and embodiments of the present invention and are not intended to limit the invention.

EXAMPLE 1

We have developed a bacterial "two-hybrid" system that readily allows selection from libraries greater than $10^8$ in size. Our bacterial system may be used to study either protein-DNA or protein-protein interactions, and it offers a number of potentially significant advantages over existing yeast-based one-hybrid and two-hybrid methods. We tested our system by selecting zinc finger variants (from a large randomized library) that bind tightly and specifically to desired DNA target sites. Our new method allows sequence-specific zinc fingers to be isolated in a single selection step, and thus it should be more rapid than phage display strategies which typically require multiple enrichment/amplification cycles. Given the large library sizes our bacterial-based selection system can handle, this method should provide a powerful tool for identifying and optimizing protein-DNA and protein-protein interactions.

Selection and screening methods are powerful tools for studying macromolecular interactions. Examples of such methods include the yeast-based one-hybrid and two-hybrid systems (for studying protein-DNA and protein-protein interactions, respectively) and bacterial-based phage display methods (for studying either type of interaction). These systems have been used to identify interaction partners for particular DNA or protein targets, and they have also been used in combination with mutagenesis or randomization strategies to study the details of biologically important interactions (for reviews, see 1–5). The development of bacterial-based systems analogous to the yeast one-hybrid and two-hybrid methods could, in principle, facilitate the rapid analysis of larger libraries (due to the higher transformation efficiency and faster growth rate observed with *E. coli*). Such methods might also be faster than phage display, which is an enrichment technique requiring multiple rounds of affinity purification and amplification (see, for example, 6).

Several bacterial one- and two-hybrid systems have been proposed, but there have been no reports in which these actually have been used to identify candidates from a real library (reviewed in 7). This may reflect practical limitations with these existing systems. Most of these methods are actually designed as genetic screens (8–10) and thus can not be readily used with libraries greater than ~$10^5$–$10^6$ in size. Two genetic selection systems have been proposed for studying protein-protein interactions, but neither method is readily adaptable to the analysis of protein-DNA interactions (11, 12).

In this report we describe the design and testing of an *E coli*-based selection method that can detect either protein-DNA or protein-protein interactions and that can handle libraries larger than $10^8$ in size. We tested our new method by selecting $Cys_2His_2$ (SEQ ID NO: 4) zinc finger variants similar to those previously isolated by phage display (6, 13). The results of our selection, the rapidity of our method, and the versatility of the underlying transcriptional activation scheme suggest that this bacterial-based system should provide a useful tool for identifying and characterizing protein-DNA and protein-protein interactions.

Materials and Methods

Selective medium. "HIS selective medium" is composed of M9 minimal medium supplemented with 10 μM $ZnCl_2$, 10 μg/ml thiamine, 200 μM adenine, 50 μg/ml carbenicillin, 30 μg/ml chloramphenicol, 30 μg/ml kanamycin, 50 μM IPTG, 20 mM 3-aminotriazole (3-AT), and 17 amino acids (all except histidine, methionine, and cysteine). For HIS selective medium plates, agar was added to a final concentration of 1.5%.

Plasmids and bacterial strains. The αGal4 protein used in this study contains residues 1–248 of the *E. coli* RNA polymerase α subunit fused (by an Ala-Ala-Ala linker) to residues 58–97 of the yeast Gal4 protein. The pACYC 184-derived plasmid pACL-αGal4 expresses αGal4 from a tandem, IPTG-inducible lpp/lacUV5 promoter.

The Gal11P-Zif123 fusion protein contains residues 263–352 of the yeast Gal11P protein (with a N342V mutation [14]) fused by a nine amino acid linker Ala-Ala-Ala-Pro-Arg-Val-Arg-Thr-Gly (SEQ ID NO: 5) to residues 327–42 1 of Zif268 (the region encoding the three zinc fingers). The phagemid pBR-GP-Z123 expresses the Gal11P-Zif123 hybrid protein from an IPTG-inducible lacUV5 promoter. The pBR-GP-Z12BbsI phagemid is analogous to pBR-GP-Z123 except that Zif finger 3 is replaced with a modified Zif finger 1 in which the sequence encoding residues—1 through 6 of the finger recognition helix is replaced by unrelated sequence (a "stuffer" fragment) flanked by BbsI restriction sites. All phagemids used in this study can be easily "rescued" from cells by infection with a filamentous helper phage; infectious phage particles produced by these cells contain single-stranded phagemid DNA.

The reporter construct that expresses HIS3 ($P_{zif}$-HIS3-aadA) has the Zif268 binding site sequence 5'GCGTGGGCG3' centered at base pair −63 relative to the transcription start site of a weak *E. coli* lac promoter derivative (the $P_{wk}$ promoter). The three selection strain reporters change the zinc finger binding site of $P_{Zif}$-HIS3-aadA, replacing the sequence 5'TCGACAAGCGTGGGCG3' (SEQ ID NO: 6) (bases −74 to −59 relative to the transcription start site) with sequences that should allow binding of the desired zinc finger variants: 5'CAAGGGTTCAGGGGCG3' (SEQ ID NO: 7) (for NRE), 5'GGCTATAAAAGGGGCG3' (SEQ ID NO: 8) (for TATA), or 5'TGGGACATGTTGGGCG3' (SEQ ID NO: 9) (for p53). Each of these reporters was transferred (by recombination) to an F' episome encoding $lacI^q$ repressor and then introduced into strain KJ1C in a single step essentially as previously described (15, J. K . J. & C. O. P., unpublished). The resulting strains were then each transformed with the pACL-αGal4 plasmid to create the NRE, TATA, p53, and Zif "selection strains."

*E. coli* strain KJ1C, which has a deletion in the hisB gene, was constructed as follows: Strain SB3930 (F-ΔhisB463) was transduced to tetracycline resistance with $P1^{vir}$ phage grown on strain JCB40 (F-Δ(gpt-proAB-arg-lac)XIII zaj::Tn10). Tetracycline-resistant colonies were screened for pro-, arg- lac-, and his- phenotypes.

Randomized zinc finger library. The zinc finger variant library was constructed by cassette mutagenesis. Randomized oligonucleotides synthesized using a two-column method (16) were ligated to BbsI-digested pBR-GP-Z12BbsI vector (replacing the "stuffer" fragment in this phagemid) to create a library of zinc finger variants. Each member of this library has three zinc fingers: two constant fingers (fingers 1 and 2 of Zif268) and a third, carboxy-terminal finger (also derived from finger 1 of Zif268) in which recognition helix residues −1, 1, 2, 3, 5, and 6 are randomized. Our randomization scheme allows 24 possible codons, encoding 19 possible amino acids (no cysteine) and one stop codon. The sequence complexity of the resulting library is ~2×10$^8$. This ligation was electroporated into *E. coli* XL-1 Blue cells (Stratagene) and yielded >10$^9$ transformants. These were pooled, amplified, and then infected with VCS-M13 helper phage (Stratagene) to yield a high titer stock of phage harboring single-stranded versions of the phagemid library.

Selection protocols. For initial selections with each of the three variant sites, >10$^{10}$ selection strain cells were infected with approximately 10$^9$ ampicillin-resistance transducing units (ATU) of phage from the phagemid library. After recovery under non-selective conditions for 1.5 hours, infected cells were plated at a density of approximately 1 to 5×10$^8$ ampicillin-resistant colonies/plate on "HIS selective medium." (Control experiments indicated a false positive rate of ~3×10$^{-8}$ under these selection conditions.) The largest surviving colonies were re-tested for growth on HIS selective medium plates supplemented with 60 μg/ml spectinomycin (we chose 80–90 colonies for the NRE and TATA selections and 240 colonies for the p53 selection). Candidates that re-grew on these plates were then chosen for phagemid-linkage testing.

The second NRE selection was performed in two stages, in an attempt to isolate additional variants. In the first stage, >10$^{10}$ NRE selection strain cells were infected with ~6×10$^9$ ATU of phage from the phagemid library. After recovery under non-selective conditions, the infection was plated at a density of ~6×10$^8$ ampicillin-resistant colonies/plate on HIS selective medium. Half of the ~900 surviving colonies were pooled and amplified in liquid HIS selective medium supplemented with 50 μg/ml spectinomycin. This pooled culture was infected with VCS-M13 helper phage, grown overnight in 2xYT medium supplemented with 50 μg/ml spectinomycin, and a high titer stock of phage was isolated. For the second stage, fresh NRE selection cells were infected with phage containing the enriched library of phagemids (from the first stage), and these were plated on HIS selective medium plates. Twenty-four surviving colonies of various sizes were re-tested for growth on HIS selective medium plates (supplemented with 60 μg/ml spectinomycin) and these were then checked for phagemid-linkage.

Phagemid-linkage testing. Colonies that grew on HIS selective medium were then tested to see whether survival was phagemid-linked. Candidates were inoculated into liquid HIS selective medium supplemented with 100 μg/ml spectinomycin (but lacking 3-AT). All of the NRE and TATA selection candidates, and the 72 fastest growing p53 selection candidates, were each infected with VCS-M13 helper phage, and the resulting phage-containing supernatants were harvested. Each candidate phage was used to infect fresh selection strain cells (corresponding to those on which it was originally selected), and these infected cells were plated on HIS selective medium. Growth under these conditions demonstrates that activation of HIS3 expression is linked to the presence of the phagemid (and thus suggests that the phagemid-encoded zinc fingers bind to the DNA target site on which they were selected).

Binding site preference testing. To test the ability of the selected zinc fingers to discriminate among different binding sites, recovered phagemids were introduced (by phage infection) into NRE, p53, TATA, and Zif selection strain cells. Infected cells were plated on HIS selective medium and growth scored qualitatively after 24 hours growth at 37° C. and 18 hours continued growth at room temperature. Under these conditions, we have found that survival of a selection strain indicates that the variant finger can bind the target subsite present on the reporter. If a zinc finger variant permits selection strains (other than the one in which it was initially isolated) to survive on selective medium, this suggests that the variant finger binds semi- or non-specifically.

Sequencing of candidates. To prepare candidates for sequencing, the phage stocks of clones with a phagemid-linked phenotype were used to infect XL-1 Blue cells. Plasmid DNA was isolated from these cells (QIAgen) and used for dideoxy sequencing.

Results

An improved *E. coli*-based "two-hybrid" selection system for studying protein-DNA and protein-protein interactions. To design a bacterial-based selection method for studying protein-DNA and protein-protein interactions, we began with an existing genetic screen previously developed by Hochschild and colleagues (7, 8, 10). In this screen, as in the yeast "two-hybrid" system, there are two fusion proteins that interact in a way that leads to transcriptional activation of a lacZ reporter gene (FIG. 1A). One protein is composed of a DNA binding domain (DBD) fused to another domain represented as X in FIG. 1A. The second protein contains the domain Y fused to a subunit of the *E. coli* RNA polymerase. In this arrangement, activation of lacZ expression requires appropriate protein-DNA and protein-protein interactions: The DBD must bind to a DNA binding site (DBS) positioned near the promoter, and domain X must simultaneously interact with domain Y to recruit RNA polymerase to the promoter, thereby activating transcription. The major advantage of this system is that almost any protein-DNA (DBD-DBS) or protein-protein (X-Y) interaction should mediate transcriptional activation. However, because lacZ is used as a reporter gene in this system, candidates must be identified by a visual phenotype (e.g.—their blue color on X-gal plates). Thus, the system (in this form) can not readily be used to screen libraries larger than ~10$^5$–10$^6$ in size.

Figure 1B:
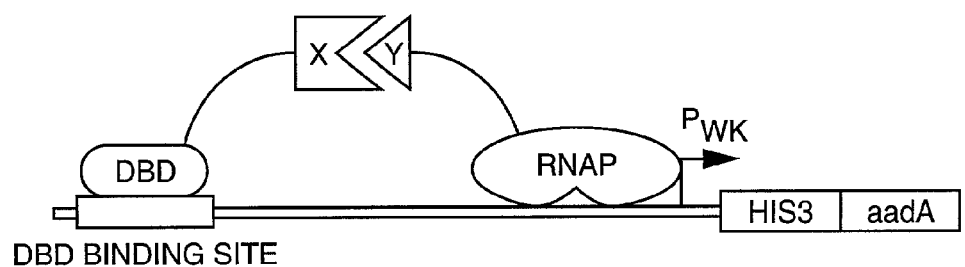

To improve this previously described system so that it can be used to analyze libraries greater than 10$^8$ in size, we replaced the lacZ gene used in the Hochschild genetic screen with the selectable yeast HIS3 gene (FIG. 1B). HIS3 encodes an enzyme required for histidine biosynthesis that can complement the growth defect of *E. coli* cells bearing a deletion in the homologous hisB gene (ΔhisB cells) (17, 18). In addition, 3-aminotriazole (3-AT), which is a competitive inhibitor of HIS3, can be used to titrate the level of HIS3 expression required for growth on medium lacking histidine (19). (Thus, in the presence of 3-AT, a higher level of activation is required to allow growth on selective medium.) We find that HIS3 is attractive for use with large libraries since: 1) >10$^8$ ΔhisB cells harboring a HIS3 gene expressed from the P$_{wk}$ promoter can be plated on a regular-size Petri dish containing HIS selective medium, and 2) we find that these cells have a very low false positive rate (about 3×10$^{-8}$) on HIS selective medium (data not shown).

Our modified construct also contains the bacterial aadA gene (which confers resistance to the antibiotic spectinomycin) (20) positioned just downstream of the HIS3 gene (FIG. 1B). We refer to this construct as the P$_{wk}$-HIS3-aadA operon because P$_{wk}$ directs coordinated expression of the HIS3 and aadA genes (data not shown). Although selection for increased aadA expression is not suitable for direct analysis of large libraries (we find this allows a relatively high background breakthrough [data not shown]), we used spectinomycin in certain steps to maintain selective pressure (see Materials and Methods). In addition, we also constructed reporter strains which harbor a lacZ gene positioned just downstream of the HIS3 gene. In this synthetic operon, $P_{wk}$ directs coordinated expression of the HIS3 and lacZ genes. In this configuration, basal expression of lacZ is low and thus cells harboring this reporter construct form white colonies on X-gal-containing medium (data not shown).

Figure 1C:
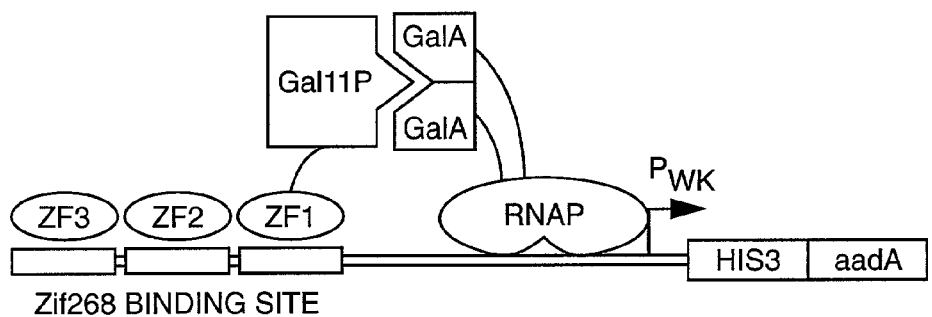

Zinc finger domains can bind DNA and activate transcription in *E.coli*. We tested our new *E.coli*-based system by applying it to a problem previously studied using phage display: the selection, from a large randomized library, of zinc finger variants with altered DNA binding specificities (for review, see 21). However, before proceeding with selections, we first examined whether a wild-type zinc finger protein could bind DNA and activate transcription in our system. (Relatively little information was available on the activity of $Cys_2His_2$ (SEQ ID NO: 4) zinc finger proteins in bacteria.) To do this, we constructed fusion proteins containing fragments of the yeast Gal11P and Gal4 proteins that had previously been shown to interact with each other (10, 14). Thus, we fused a Gal11P fragment to the three zinc fingers of the murine Zif268 protein (creating the Gal11P-Zif123 protein), and we replaced the carboxy-terminal domain of the *E.coli* RNA polymerase α subunit with a Gal4 fragment (creating the chimeric αGal4 protein). A Zif268 DNA binding site was positioned upstream of our $P_{wk}$-HIS3-aadA operon to create the $P_{Zif}$-HIS3-aadA operon (FIG. 1C), and this cassette was introduced into a ΔhisB *E.coli* strain in single copy to create the "Zif reporter strain."

We then tested whether the Gal11P-Zif123 and αGal4 proteins could work together as a "two-hybrid" system to activate transcription of the $P_{zif}$-HIS3-aadA operon. We find that Zif reporter strain cells expressing only the αGal4 protein do not grow on HIS selective medium, but the same cells can grow when the Gal11P-Zif123 protein is expressed together with the αGal4 protein. We also find that activation requires all three Zif268 fingers: a Gal11P fusion protein which contains only the first two zinc fingers from Zif268 does not permit growth on selective medium. We performed similar experiments using reporter cells harboring the $P_{wk}$-HIS3-lacZ operon and obtained similar results (data not shown) on HIS selective medium. In addition, cells harboring the HIS3-lacZ operon in which the promoter is activated by the Gal11P-Zif123/αGal4 interaction form blue colonies on X-gal medium, indicating increased expression of the lacZ reporter gene. These results indicate that the Gal11P-Zif123 and αGal4 proteins can work together to activate transcription in our *E. coli* system. We presume that the DNA-bound Gal11P-Zif123 acts by recruiting (or stabilizing) RNA polymerase complexes that have incorporated αGal4. These results also give some information about the DNA-affinity threshold for activation since we find that fingers 1 and 2 of Zif268 alone are not sufficient.

Selection strategy for isolation of zinc finger variants. Since our initial results indicated that zinc fingers could function in *E. coli* and that our activation scheme worked as expected, we proceeded to test our system by isolating zinc finger variants from a large randomized library. We chose target DNA subites that had been used in an earlier phage display study (6, 13). This previous study had involved selecting zinc finger variants that would bind to sequences normally recognized by important eukaryotic DNA-binding proteins. The AAA target subsite used in our experiments is part of a TATA box, the TGT target subsite is part of a p53 binding site, and the TCA target subsite is part of a nuclear receptor element (NRE). We refer to these sequences as the "TATA," "p53," and "NRE" target subsites.

Our strategy for identifying variant zinc fingers that bind specifically to a particular "target" DNA subite relies on the ability of our system to distinguish between zinc finger proteins that bind using two fingers (recognizing 6–7 bp) from those that bind using three fingers (recognizing 9–10 bp). We synthesized a large library of three-finger Zif268-derivatives (each fused to the Gal11P fragment). In this library, the first two fingers of Zif268 remain constant, but the recognition helix of the third, carboxy-terminal finger is randomized (see Materials and Methods). We also prepared "selection strains" with the appropriate zinc finger binding sites upstream of the $P_{wk}$-HIS3-aadA operon. (Each of these has the normal binding subites for fingers 1 and 2 of Zif268, but the third subsite [black notched rectangle, FIG. 2] is changed to include the "target" DNA subsites of interest [AAA for TATA; TGT for p53; TCA for NRE].) Each of these ΔhisB selection strains also contain a plasmid expressing the αGal4 protein, and these bacteria are referred to as the TATA, p53, and NRE selection strains. (As a control for use in binding site specificity studies [see below], we also constructed a corresponding "Zif selection strain" that has an intact Zif268 binding site [containing subsites for all three Zif268 fingers] positioned upstream of the $P_{wk}$ promoter.)

Figure 2:
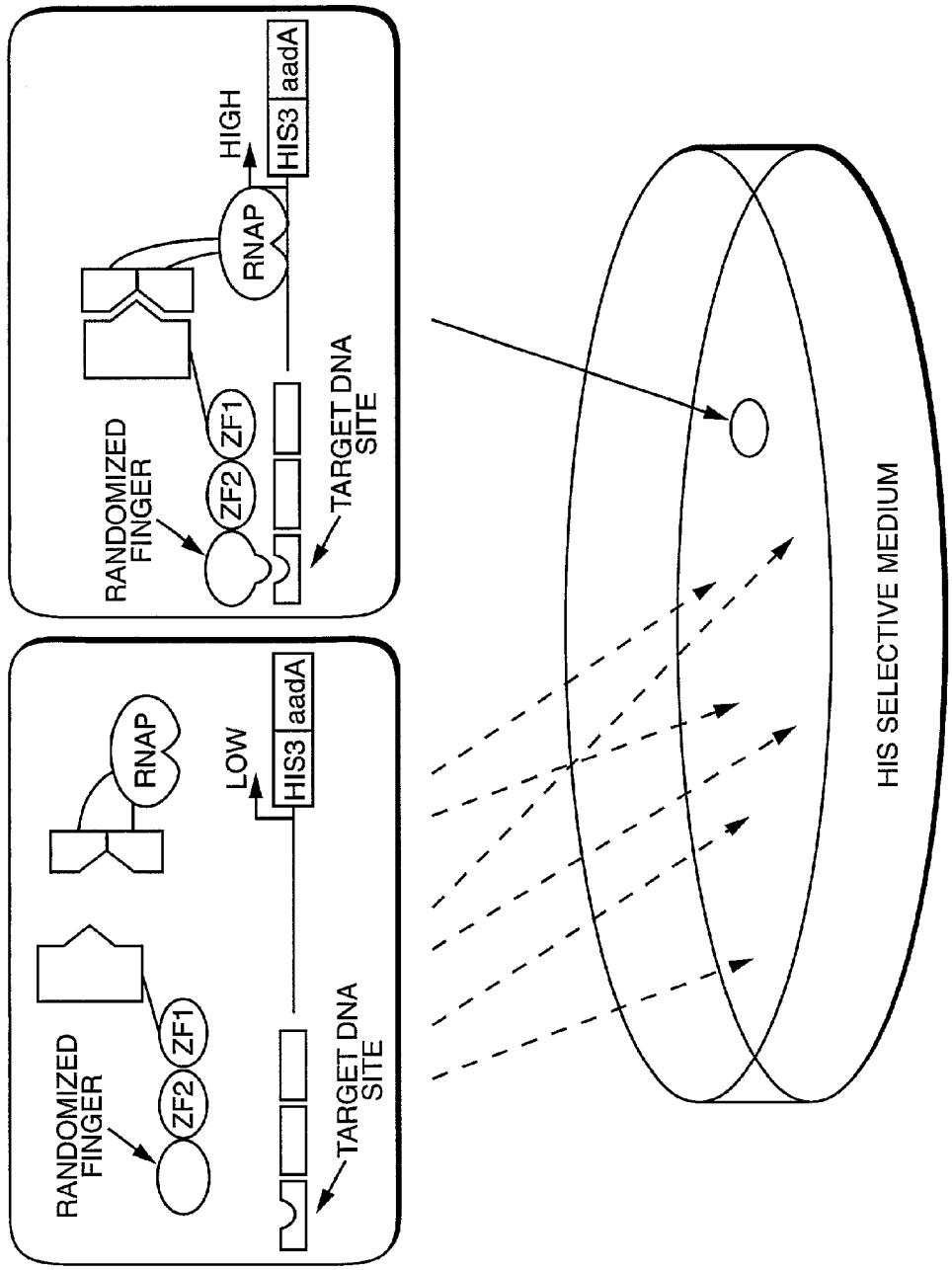
FIG. 2. An *E. coli*-based selection system for identifying zinc finger variants from large randomized libraries. The left side of the figure depicts a selection strain cell bearing a randomized zinc finger (white oval) that is unable to bind the target DNA subsite of interest (black box). This candidate fails to activate transcription of the weak promoter controlling HIS3 expression and therefore cells expressing this candidate fail to grow on HIS selective medium. The right side of the figure depicts a library candidate bearing a particular zinc finger (one member of the randomized library) (black oval) that can bind the target DNA site. This candidate can activate HIS3 expression and therefore cells expressing this candidate grow on HIS selective medium.

To perform a selection with one of these three target subsites, we introduced >5×10$^8$ members of the phagemid library into the appropriate selection strain and plated the cells on HIS selective medium. From our earlier controls, we expected that growth would require three functional fingers; thus, a cell should survive only if it happens to express a protein with a finger that binds tightly to the target subsite (FIG. 2).

Positive candidates identified on HIS selective medium were then checked in several ways: Each candidate was first tested to verify that the phenotype of growth on selective medium was linked to the phagemid encoding the zinc finger library candidate (phagemid-linkage test, see Materials and Methods). Clones that still appeared positive were then tested to see how well they distinguish among the NRE, TATA, p53, and Zif subsites (binding site preference test, see Materials and Methods). Finally, clones were sequenced to determine which amino acids were preferred at the positions that had been randomized.

Figures 3A, 3B:
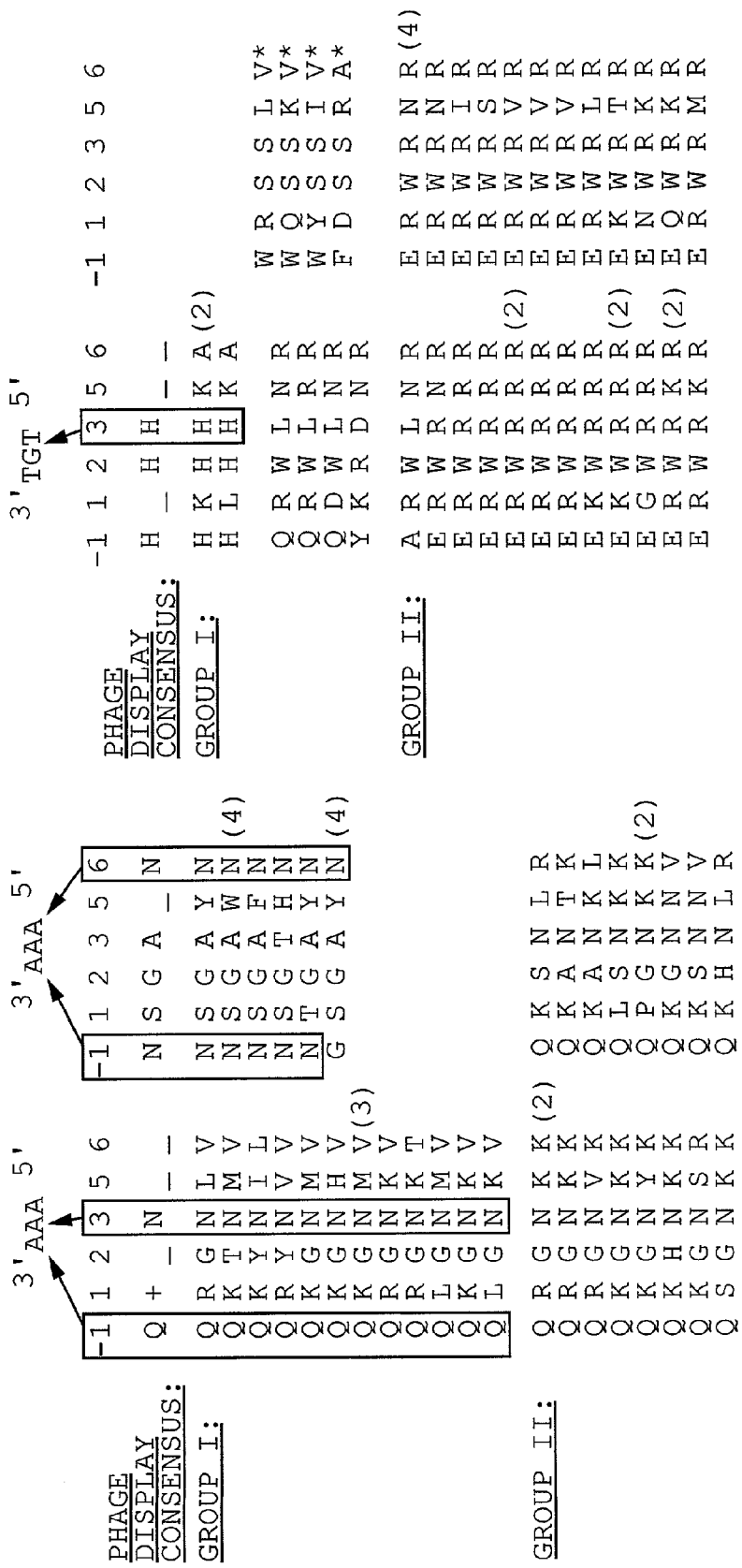
FIG. 3. Recognition helix sequences of fingers isolated by our selection. For candidates that were isolated multiple times (as judged by nucleotide sequence), the number of clones obtained is shown in parentheses. The consensus sequence(s) of fingers selected by phage display for each target subsite are also shown (ref 6, +denotes a positively charged residue, denotes no discernible preference). Asterisks indicate candidates with a 2 bp deletion downstream of the sequence encoding the recognition helix. Arrows illustrate a few of the most plausible potential base contacts. (SEQ ID NOS 23–91, respectively, in order of appearance).
Figure 4B:
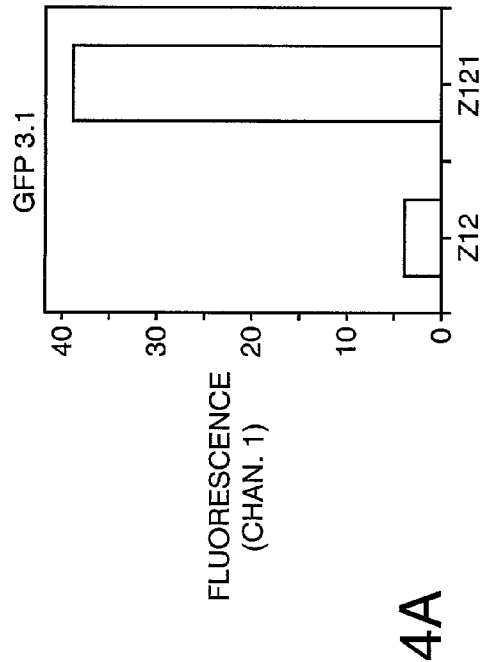
FIG. 4. Illustrates the behavior of various fluorescent proteins in the bacterial two-hybrid system.
Figure 4D:
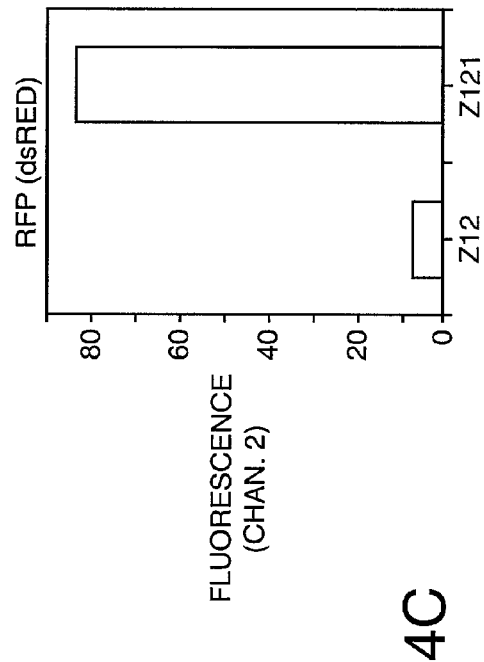
Figure 4A:
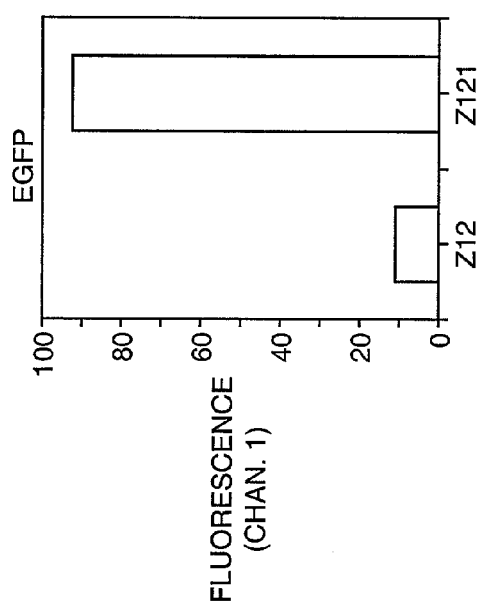
Figure 4C:
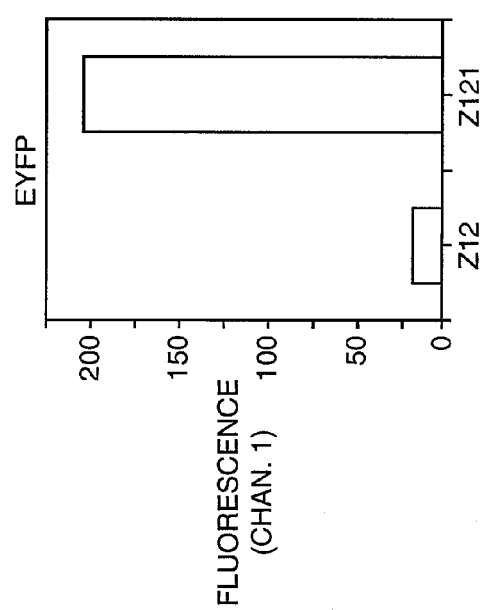

Selection of Zinc Fingers that bind the TATA Target Subsite. From the ~5×10$^8$ zinc finger variants introduced into the TATA selection strain, we identified 50 candidates with a phagemid-linked phenotype. Based on their ability to distinguish among the TATA, p53, NRE and Zif subsites, these candidates can be categorized into three groups. Group I candidates bind specifically to the TATA target subsite. Group II candidates bind semi-specifically (with a strong preference for the TATA subsite over the Zif subsite); Group III candidates bind non-specifically to all four subsites tested (with a preference for the Zif and p53 subsites over the TATA and NRE subsites). Amino acid sequences are shown in FIGS. 3A (Groups I and II) and 3D (Group III) and reveal striking conserved patterns for each of the groups.

Selection of Zinc Fingers that bind the p53 Target Subsite. From the ~1.3×10$^9$ zinc finger variants introduced into the p53 selection strain, we identified 43 candidates that demonstrate a phagemid-linked phenotype. Based on their ability to distinguish among the four different subsites, these candidates can be categorized into three groups. Group I candidates bind specifically to the p53 target subsite. Group II candidates bind semi-specifically (with a general preference for the p53 subsite over the Zif subsite); Group III candidates bind non-specifically to all four subsites tested (again with a slight preference for the Zif and p53 subsites over the TATA and NRE subsites). The amino acid sequences of the recognition helices of these candidates are shown in FIGS. 3B (Groups I and II) and 3D (Group III). Striking patterns of conserved residues are seen in each group.

Selection of Zinc Fingers that bind the NRE Target Site. ~$2 \times 10^9$ zinc finger variants were introduced into the NRE selection strain, and we obtained two candidates that demonstrated a phagemid-linked phenotype. One candidate binds specifically to the NRE target subsite (and also exhibits very weak binding to the TATA subsite). The second candidate binds non-specifically to all four subsites tested (with a preference for the Zif and p53 subsites over the NRE and TATA subsites). We selected a finger with a similar recognition helix sequence using reporter cells harboring the $P_{wk}$-HIS3-lacZ operon (data not shown).

To isolate additional clones that recognize the NRE subsite, we performed a modified two-stage selection procedure. In the first stage, we repeated the selection for the NRE subsite and pooled 50% of the surviving colonies (approximately 450 candidates). In the second stage, finger-encoding phagemids isolated from this enriched pool (see Materials and Methods) were then re-introduced into the NRE selection strain and plated again on selective medium. All 24 colonies chosen for further analysis displayed a phagemid-linked phenotype, and these zinc fingers could be categorized into two groups on the basis of their observed specificities. Group I sequences bind well to the target NRE subsite (with very weak binding to the TATA subsite). Group III candidates bind non-specifically to all four subsites tested (with a preference for the Zif and p53 subsites over the NRE and TATA subsites). The recognition helix sequences of all of the selected candidates are shown in FIGS. 3C (Group I) and 3D (Group III). As with our other selections, striking patterns of conserved residues are observed in each of these groups.

Discussion

Selection of variant zinc fingers with altered DNA-binding specificities using a bacterial-based selection method. Our bacterial-based selection system is designed to rapidly identify and characterize protein-DNA and protein-protein interactions. To test our method, we performed selections to identify variant zinc fingers that would bind selectively to desired target DNA subsites. We discuss these results in some detail in the following paragraphs, but our main observation is that the affinity and specificity of the selected fingers seems comparable, if not superior, to those obtained in earlier phage display studies (which required multiple rounds of selection and amplification).

For the TATA selection, subsite-specific fingers identified by our method (TATA Group I) define two consensus sequences, and these closely match the two consensus sequences observed in fingers isolated by phage display (FIG. 3A). However, the randomization scheme used in constructing our library allowed aromatic amino acids (Phe, Tyr and Trp) that were not represented in the codon scheme used for the corresponding phage display library (6, 13). One consensus sequence obtained with our selection appears to specify an aromatic residue at position 5 of the recognition helix (NSGAθN, where θ is an aromatic residue). The corresponding phage display-derived consensus (NSGA_N) does not define any particular class of residues at this position. Our selection also yielded another class of fingers that appear to be semi-specific for the TATA subsite (TATA Group II fingers). The sequences of these fingers also match one of the phage display consensus sequences, but all (except one) of these semi-specific fingers are distinguishable from the specific fingers (TATA Group I) by the presence of either an asparagine at position 5 or a positively charged residue at position 6 (FIG. 3A). Thus, the results for this subsite are quite clear: our selection yields fingers that bind specifically to the TATA subsite, and the sequences of these fingers match well with those isolated by phage display.

For the p53 selection, we isolated a number of fingers that bind specifically to the intended target subsite (p53 Group I). The recognition helix sequences of two of these fingers match the consensus sequence of those obtained by phage display (FIG. 3B). We note that the remaining p53 Group I fingers have an aromatic residue at either position −1 or 2 of the recognition helix and thus would not have been present in libraries used for earlier phage display experiments. In addition, fingers isolated by our method that bind semi-specifically to the p53 subsite (p53 Group II fingers) all possess a tryptophan at position 2. Although the nature of some of the sequence-specific contacts made by these fingers is unclear, the conservation of specific aromatic residues at certain positions suggests an important role in DNA recognition. Again, our results with this subsite are very encouraging: our selection yields a number of fingers that bind specifically to the p53 target subsite. Some of these fingers match the consensus obtained by phage display while others suggest that aromatic residues may play an important role in zinc finger-DNA recognition.

For the NRE target subsite, an initial attempt using our new selection method yielded only one finger (NSGSWK) (SEQ ID NO: 10) that bound preferentially to the target sequence. Based on our existing knowledge of zinc finger-DNA recognition (reviewed in 21), one can postulate reasonable contacts between recognition helix residues of this finger and bases in the primary strand of the NRE subsite (FIG. 3C). However, we were initially concerned by the relatively low frequency of fingers selected for this site, and we repeated the selection using an additional enrichment step in an attempt to isolate more fingers. The great majority of sequences isolated this way had the same amino acid sequence as the candidate originally selected (NSGSWK) (SEQ ID NO: 10) but two closely related sequences (NSGSHK (SEQ ID NO: 11) and NHGSWK (SEQ ID NO: 12)) were also identified. These results suggested that we might have obtained a small number of clones merely because very few candidates in our library can pass the threshold set in our NRE selection.

As shown in FIG. 3C, the sequences of fingers isolated in our NRE selections do not match the consensus sequence for fingers selected by phage display. We performed several experiments to explore the basis of this difference: We first checked our library by sequencing random candidates to ensure that there was no drastic bias in nucleotide distribution and were able to rule this out as a plausible explanation (unpublished data). We then decided to directly introduce (in exactly the same context) one of the fingers (TRTNKS) (SEQ ID NO: 13) that had been selected by phage display (6) and see whether it could work in our system as a Gal11P-zinc finger fusion protein. We find that NRE selection strain cells expressing this TRTNKS (SEQ ID NO: 13) finger fusion protein grow very poorly on HIS selective medium whereas the same cells expressing the NSGSWK (SEQ ID NO: 10) finger fusion (obtained in our selections) grow robustly (unpublished data). The simplest explanation for this result is that the TRTNKS (SEQ ID NO: 13) finger fusion binds poorly to the NRE subsite and therefore only weakly stimulates HIS3 expression. This explanation is supported by our observation that earlier selections with the NRE subsite, using a prototype of our system in which zinc fingers were expressed from a much higher copy number phagemid, had yielded the TRTNKS (SEQ ID NO: 13) as well as the NSGSWK (SEQ ID NO: 10) finger (J.K.J. and C.O.P., unpublished data). This suggests that our current system sets a very stringent standard for the NRE selections and may account for why we isolated such a small number of specific candidates.

We also used our binding site preference assay to compare the specificity of the NSGSWK (SEQ ID NO: 10) finger we had selected for the NRE subsite with that of the TRTNKS (SEQ ID NO: 13) finger selected by phage display, In our bacterial-based assays, the NSGSWK (SEQ ID NO: 10) finger binds specifically to the NRE subsite and binds only very weakly to the TATA subsite. By contrast, the TRTNKS (SEQ ID NO: 13) finger binds only weakly to all four subsites (exhibiting a preference for the NRE and TATA subsites over the p53 and Zif subsites) (unpublished data). These results suggest that the NSGSWK (SEQ ID NO: 10) finger we selected actually binds more tightly and specifically in our system than the TRTNKS (SEQ ID NO: 13) finger identified earlier by phage display.

Each of our three selections also yielded a small percentage of fingers that bind non-specifically to all four DNA subsites tested. Surprisingly, all of these fingers match a consensus sequence of the form R+WL+L(SEQ ID NO: 14) (where + denotes a positively charged residue, FIG. 3D). These fingers are rich in positive charge and may make extra phosphate contacts. We also note that all of these fingers have a tryptophan residue at position 2 and thus would not have been present in the libraries used for earlier phage display experiments. This highly conserved set of non-specific fingers raises many interesting questions: What level of specificity is required for a zinc finger protein to function in our assay (and thus to what extent does the E. coli chromosome function as a non-specific competitor)? How do these fingers bind? Why is this particular class of non-specific fingers the only type selected in our system?

In summary, the TATA and p53 subsite selections demonstrate that our bacterial-based system can isolate fingers similar to those obtained previously by phage display. Only a few fingers were obtained in the NRE subsite selections, but it appears that these may actually bind with better affinity and specificity than those obtained by phage display. Most significantly, we believe our new method offers a more rapid alternative to phage display because it permits functional fingers to be isolated in a single selection step instead of using multiple rounds of enrichment. We also note that (as with recent phage display efforts from this lab and other laboratories) we took no special precautions to perform our selections in an anaerobic environment. We envision that our rapid bacterial-based system will be particularly useful for projects requiring multiple zinc finger selections (performed either in parallel or sequentially).

General strategies for studying protein-DNA and protein-protein interactions utilizing our bacterial-based two-hybrid selection system. This report demonstrates that our bacterial-based system can be used in a manner analogous to the yeast one-hybrid method to identify variant zinc fingers that bind to a specific DNA subsite. We have also found that a number of other eukaryotic DNA binding domains can readily function in our system (J. Miller, J. Kanter, J. K. J., E. I. R., and C. O. P., unpublished results). Thus, we expect that our method could also be readily used to identify DNA-binding proteins from cDNA libraries or random peptide libraries.

With a few minor modifications, our selection method could also be used to identify and study protein-protein or protein-peptide interactions. In this application (analogous to the yeast two-hybrid method), the protein target (the "bait" or domain Y in FIGS. 1A and 1B) could be fused to either the dimeric α subunit or to the monomeric ω subunit of RNA polymerase. The protein or peptide library to be analyzed (the "prey" or domain X in FIGS. 1A and 1B) could be fused to either a dimeric (e.g.—bacteriophage λcI protein) or monomeric (e.g.—Zif268) DNA binding domain. (Previous experiments have shown that different interacting proteins X and Y can effect transcriptional activation and that the magnitude of this activation correlates well with the strength of the X-Y interaction [reviewed in 22].) The reporter in this application would be the $P_{wk}$-HIS3-aadA operon bearing an upstream binding site for the particular DBD used in the experiment. As with other applications of our system, the phagemid rescue feature simplifies and reduces the time required to analyze plasmid linkage and to test interaction specificity.

Our bacterial-based selection system offers a number of potentially significant advantages over analogous yeast-based one-hybrid and two-hybrid methods (reviewed in 7). In particular it offers: the ability to analyze libraries larger than $10^8$ in size, faster growth rate, greater potential permeability to small molecules (23), the absence of a requirement for nuclear localization, and the possibility of studying proteins that are toxic when expressed in yeast. To our knowledge, this report is the first description of a bacterial-based "two hybrid" system that has actually been used to identify candidates of interest from a large library (>$10^8$ in size). Our HIS3-based system provides a rapid selection method with a low false positive rate, and it can easily be titrated to be more or less stringent simply by varying the concentration of 3-AT inhibitor in the medium. Our method is also amenable to high-throughput analysis and automation, as many steps are performed in a 96-well format. We envision that our genetic selection method will provide a powerful, broadly applicable tool for identifying and characterizing both protein-DNA and protein-protein interactions.

Table 1. Effects of fusion proteins on HIS3 expression from the $P_{zif}$ promoter "Zif reporter strain" cells (see text) expressing the indicated fusion proteins were tested for growth on HIS selective medium.

| Fusion proteins expressed | Growth on HIS Selective Medium |
| --- | --- |
| Gal4 only | No growth |
| Gal11P-Zif123 and αGal4 | Growth |
| Gal11P-Zif12 and αGal4 | No Growth |

REFERENCES CITED IN EXAMPLE 1

1. Allen, J. B., Walberg, M. W., Edwards, M. C. & Elledge, S. J. (1995) *Trends Biol. Sci.* 20, 511–516.
2. Phizicky, E. M. & Fields, S. (1995) *Microbiol. Rev.* 59, 94–123.
3. Rebar, E. J., Greisman, H. A., & Pabo, C. O. (1996) *Mthds. Enzymol.* 267, 129–149.
4. Smith, G. P. & Petrenko, V. A. (1997) *Chem. Rev.* 97, 391–410.

5. Vidal, M. & Legrain, P. (1999) *Nucl. Acids Res.* 27, 919–929.
6. Wolfe, S. A., Greisman, H. A., Ramm, E. I., & Pabo, C. O. (1999) *J Mol. Biol.* 285, 1917–1934.
7. Hu, J. C., Kornacker, M. G., & Hochschild, A. (2000) *Methods* 20, 80–94.
8. Dove, S. L., Joung, J. K., & Hochschild, A. (1997) *Nature* 386, 627–630.
9. Kornacker, M. G., Remsburg, B. & Menzel, R. (1998) *Mol. Microbio.* 30, 615–624.
10. Dove, S. L. & Hochschild, A. (1998) *Genes Dev.* 12, 745–754,
11. Karimova, G., Pidoux, J., Ullmann, A., & Ladant, D (1998). *Proc. Natl. Acad. Sci. USA* 95, 5752–5756.
12. Pelletier, J. N., Campbell-Valois, F. -X., & Michnick, S. W (1998). *Proc. Natl. Acad. Sci. USA* 95, 12141–12146.
13. Greisman, H. A. & Pabo, C. O. (1997) *Science* 275, 657–661.
14. Farrell, S., Simkovich, N., Wu, Y., Barberis, A., & Ptashne, M. (1996) *Genes Dev.* 10, 2359–2367.
15. Whipple, F. W. (1998) *Nucleic Acids Res.* 26, 3700–3706.
16. Wolfe, S. A., Ramm, E. I., & Pabo, C. O., (2000) *Structure*, in press.
17. Struhl, K., Cameron, J. R., & Davis, R. W. (1976) *Proc. Natl. Acad. Sci. USA* 73, 1471–1475.
18. Struhl, K. & Davis, R. W. (1977) *Proc. Natl. Acad. Sci USA* 74, 5255–5259.
19. Brennan, M. B. & Struhl, K. (1980) *J Mol. Biol.* 136, 333–338.
20. Hollingshead, J. & Vapnek, D. (1984) *Plasmid* 13, 17–30.
21. Wolfe, S. A., Nekludova, L., & Pabo, C. O. (2000) *Annu. Rev. Biophys. Biomol.* 29, 183–212.
22. Dove, S. L. & Hochschild, A. (1998) *Cold Spring Harb Symp Quant Biol.* 63,173–180.
23. Fernandes, P. B. (1998) *Curr. Opin. Chem. Biol.* 2, 597–603.

EXAMPLE 2

In order to determine if bacterial cells can be sorted by FACS according to the methods of the present invention, we first tested the behavior of several different fluorescent proteins in our system.

We originally tried the promoter constructs described in Example 1 above with EGFP as the reporter gene, but decided that a stronger signal would be more useful. We placed the reporter construct on a low copy number p15A origin/chloramphenicol resistant plasmid rather than the single copy F factor. We then cloned the alpha-gal4 fusion and its lpp-UV5 promoter onto a low copy number plasmid with the RK2 origin and tetracycline resistance.

|  | plasmid origin | copies per cell | inducer | antibiotic resistance |
| --- | --- | --- | --- | --- |
| reporter | p15A | 20–30 | N/A | chloramphenicol |
| alpha-gal4 | RK2 | ~10 | IPTG | tetracycline |
| DBD-gal11P | ColE1 | 50–70 | IPTG | ampicilin |

As FIG. 4 illustrates, discernible differences in fluorescence of the host cells can be detected between a bait protein that binds the DNA site tightly (Z121) versus a bait protein that does not bind the DNA site tightly (Z12). We tested green fluorescent protein mut 3.1 (GFP 3.1), enhanced green fluorescent protein (EGFP), enhanced yellow fluorescent protein (EYFP) and red fluorescence protein (dsRed). In another experiment, similar results were obtained using Renilla reniformis GFP and GFPmut2 as the reporters.

Figure 5:
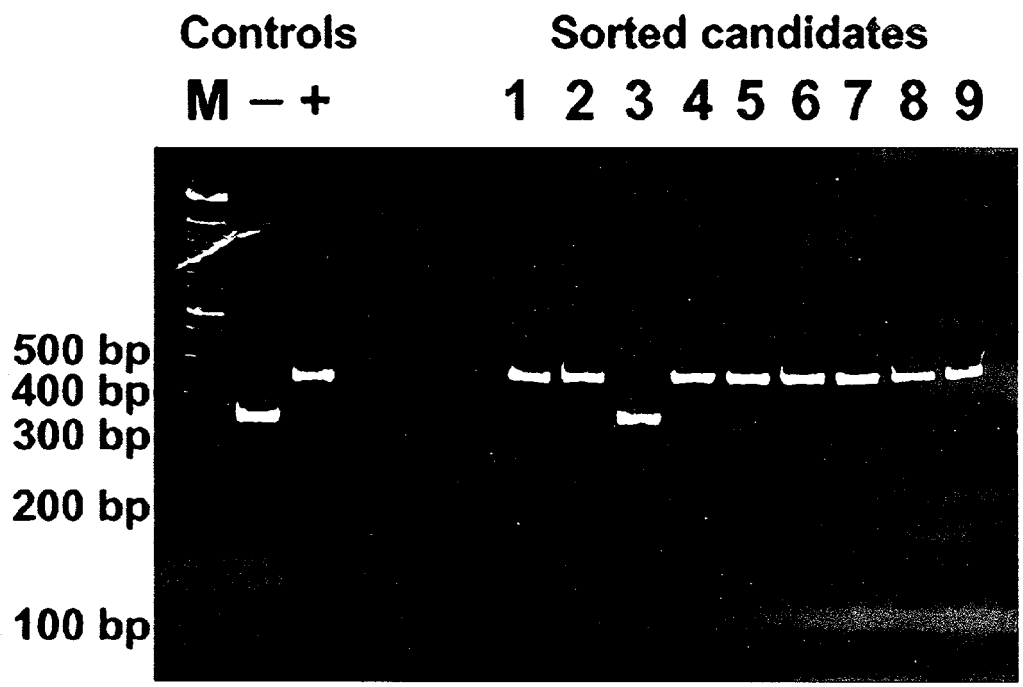
FIG. 5. Isolation of positive candidates from a mock library using flow cytometry.

FIG. 5 illustrates that interacting pairs can be isolated from a library using FACS. Approximately 200,000 cells from a mixed culture containing one "positive" cell for every 10,000 "negative" cells were sorted using a Becton Dickinson FACStar plus. Nine cells that were selected based on a high EGFP signal were cultured and analyzed by PCR. True positive cells should yield a PCR product of approximately 450 basepairs in size (positive control, lane 3). True negative cells should yield a PCR product of approximately 358 basepairs in size (negative control, lane 2). DNA size markers are in the control lane marked M. Eight of the nine clones appear to be true positives.

In the embodiment described above, both the alpha-gal4 and the zinc-finger-Gal11P fusion proteins are induced by the same chemical (IPTG). Accordingly, the concentrations of the two proteins can not be varied independently. In order to build a system where the concentrations of these proteins can be varied independently, we obtained several plasmids from Herman Bujard's lab in Germany that make it easy to swap origins, antibiotic resistance genes, and promoters between plasmids, and we made and tested a number of different combinations of alpha-Gal4, reporter constructs, and zinc-finger Gal11P fusion with different plasmid origins under the control of different promoters. The setup that gave the best results uses our previous reporter construct (on the p15A origin plasmid), has the zinc-finger-Gal11P fusion under the control of the pLlacO-1 promoter (IPTG inducible), on a plasmid with the ColE1 origin and Ampicillin resistance (pZE12), and has the alpha-Gal4 fusion under the control of the pLtetO-1 promoter (inducible by anhydrotetracycline-aTc) on a plasmid with the low copy number pSC101 origin and Kanamycin resistance (pZS21). With the proper concentrations of inducers (IPTG and aTc), we have seen up to 27 fold activation. This ability to independently control expression of the fusion proteins should make the system much more powerful since we can keep the alpha-Gal4 concentration at the optimal level while adjusting the protein level to a concentration that is appropriate for the affinity and specificity of the particular protein under study. For example, in an embodiment where directed evolution is used through subsequent rounds of isolation, one could start out with high protein expression in the early rounds and then lower the protein expression in subsequent rounds as the evolved proteins became better and better at binding the target site tightly and specifically (and this could be done without lowering the alpha-gal4 concentration).

|  | plasmid origin | copies per cell | inducer | antibiotic resistance |
| --- | --- | --- | --- | --- |
| reporter | p15A | 20–30 | N/A | chloramphenicol |
| alpha-gal4 | pSC101 | ~10–12 | aTc | kanamycin |
| DBD-gal11P | ColE1 | 50–70 | IPTG | ampicilin |

Figure 6:
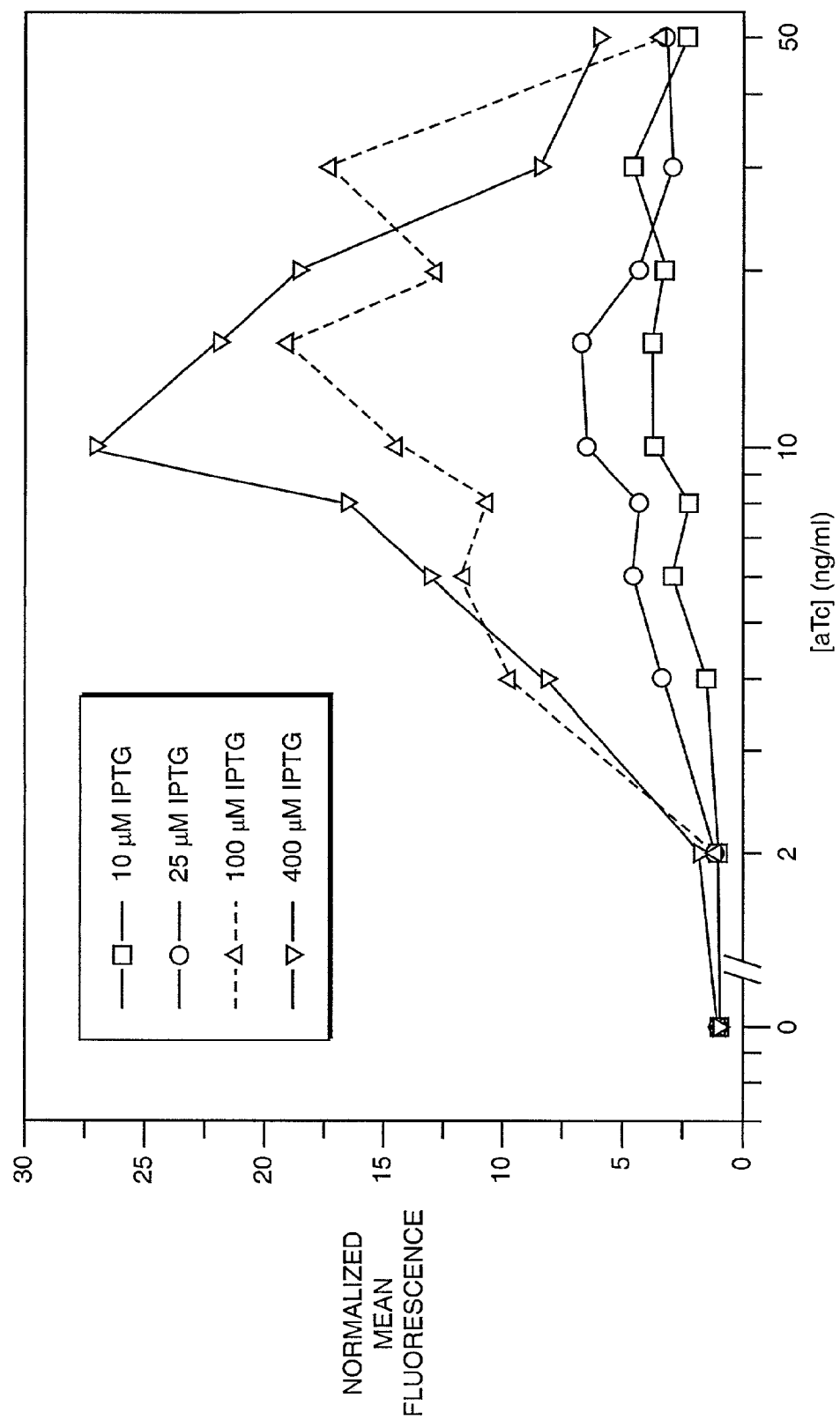
FIG. 6. This graph depicts the results of a certain embodiment of the subject interaction trap assay wherein the bait and prey protein expression levels can be individually controlled.

FIG. 6 shows preliminary data utilizing this embodiment of the system. It appears that the system is especially dependent on the concentration of aTc in the media. The fluorescence of all the samples are normalized with respect to sample #1 (which has the lowest concentration of IPTG and aTc). The cells are *E. Coli* of the strain DH5alpha-Z1 and were grown for 24 hours at 30° C. in minimal media (as described in Example 1, except the media had all 20 amino acids, contains 50 mM HEPES at pH 7.5, chloramphenicol, kanamycin, ampicilin, and the indicated concentrations of IPTG and aTc). The cells were then spun down and resuspended in PBS (phosphate buffered saline) immediately prior to measurement. The samples were measured on a Becton Dickinson FacScan flow cytometer with the standard argon ion laser (488 nm emission), the standard set of optical filters, and the EGFP signal measured in channel one. This is similar to the protocol used for cells expressing dsRed except that to get an optimal signal the cells have to be grown at room temperature for 48 hours in standard LB, or grown for 48 hours at 30° C. in minimal media with 10 g/l caseamino acids.

EXAMPLE 3

The ability to simultaneously and independently monitor the interaction of a single DNA-binding protein with multiple DNA binding sites within a single cell could be very useful for selecting proteins with differential activation at distinct DNA binding sites. Separate reporter constructs, each with a separate DNA binding site driving the expression of a reporter gene that encodes a fluorescent protein with unique fluorescent properties, is one way to achieve this goal. In order to create such a system using the bacterial two-hybrid ITS, we decided to use EGFP and dsRed (RFP) as the two reporter genes since they have different fluorescent emission spectra, but can both be excited by the argon ion lasers ($\lambda$=488 nm) commonly found in FACS machines. The first reporter construct has a binding site for the Zif268 protein, a minimal pLac promoter and EGFP as the reporter gene. The second reporter construct has a binding site for the T11 protein (a protein selected as part of Example 1), uses a hybrid promoter consisting of the $\lambda$ pRM promoter with its −35 region replaced with the −35 region of the pLac promoter, and has dsRed as the reporter gene. The sequence of the pLac promoter is: CTTTACACTTTATGCTTCCG-GCTCGTATGTTGTGTCGA (SEQ ID NO: 2) and the sequence of the hybrid promoter is: CTTTACAATTTATC-CCTTGGTC GGCTAGATTTACTCGAG (SEQ ID NO: 3).

To facilitate the introduction of both reporter constructs into the host cell and to insure equal quantities of each reporter construct within a given host cell, both reporter constructs were placed on a single two-color reporter plasmid. The orientation of the key parts of the two reporter constructs with respect to each other is shown in FIG. 7. As indicated in FIG. 7, the two reporter genes are transcribed in different directions and are thus encoded by opposite strands of DNA; this ensures that transcriptional "read-through" of one reporter gene will not erroneously affect the expression of the other reporter gene. It is also important to insure that the plasmids are designed in such a way that transcriptional "read-through" doesn't interfere with the plasmid origin of replication or with expression of the antibiotic resistance gene.

Figure 8A:
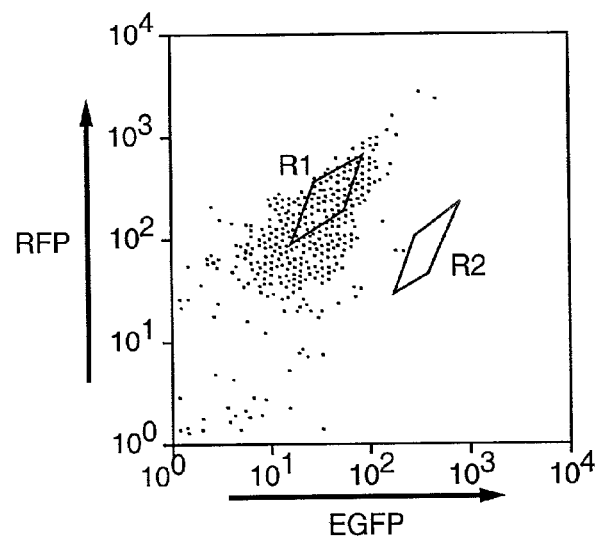
FIG. 8. This plot displays the results from three separate experiments in which otherwise identical cells, each containing the two color TZ reporter (shown in FIG. 7), are expressing either Gal11p-zif268, which should interact only with the Zif268 binding site; Gal11p-T11, which should interact only with the T11 site; and Gal11p-Z12, which should interact with neither binding site. Each dot indicates the amount of EGFP and RFP signal for an individual cell. The data for 1000 cells from each group is shown.
Figure 8B:
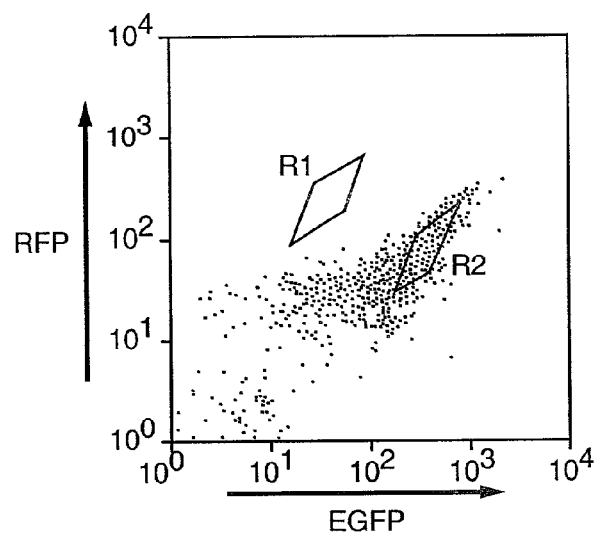
Figure 8C:
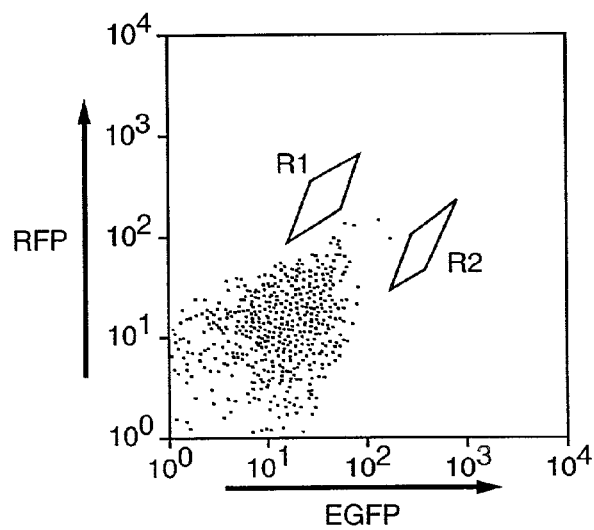

In order to test how well this reporter construct functions in the two hybrid system, the two-color plasmid containing both reporter constructs was introduced into host cells with the α-Gal4 fusion protein and one of three Gal11P-zinc finger fusions: [Gal11p-Zif268, which should interact only with the Zif268 binding site; Gal11p-T11, which should interact only the T11 site; and Gal11P-Z12, which should interact with neither binding site]. Overnight cultures of the host cells containing the two color reporter plasmid and the appropriate fusion proteins were grown in LB media on a rotating drum incubator at 37° C. and 10 µl of these saturated cultures were used to inoculate 3 ml cultures of minimal media (as described in example 2, except with 10 g/l caseaminoacids) containing 10 ng/ml aTc and 100 µM IPTG. These cultures were incubated at 30° C. on a rotating drum incubator for 48 hours and then the cultures were diluted 100 fold in Phosphate Buffered Saline (PBS) and measured on a Becton Dickinson FACScan flow cytometer. The results from each of these three separate experiments are shown in FIG. 8. The data for each experiment is presented as a dot plot were each dot indicates the amount of EGFP and dsRed (RFP) signal for a single cell by its position with respect to the X and Y axis. The data for 1000 individual cells is shown for each experiment. The regions R1 and R2 are drawn in the identical position on all three plots to allow for easy comparisons between the experiments. This data shows that cells containing a bait protein that interacts with only the first DNA site and cells that contain a bait protein that interacts with only the second DNA site can be easily separated from each other and from cells containing bait proteins that interact with neither DNA site.

Preliminary results using this embodiment of the two-color flow ITS system to select a partially randomized zinc finger, from a library of approximate $2 \times 10^7$ members, with a preference between two similar DNA sites are encouraging and a least one selected clone shows a statistically significant differential activation in favor of the desired site. Two sequential rounds of sorting were required to isolate positive clones in this experiment. A population of host cells containing the library of randomized zinc fingers was sorted to obtain cells with the desired amount of EGFP and RFP expression. This pool of selected cells was then amplified and the resulting population of cells was sorted a second time. In our current versions of both the one and two color flow ITS, multiple rounds of sorting appear to be necessary when sorting for rare clones (<1 positive per $10^5$ negatives) since there is enough variation in fluorescence among individual, genetically identical cells to allow a small proportion of genetically negative cells (i.e. cells without a bait protein that interacts with the desired DNA binding site) to have a fluorescent signal that is similar to the signal of the average genetically positive cell.

EXAMPLE 4

In addition to selecting proteins that bind to a specific DBS, this bacterial ITS can also be used to select DBS's that interact with a specific protein. FIG. 9 shows the results for such an in vivo site selection to select DNA sequences that interact with the P53$^{zf}$ protein. The consensus binding site, as determined by Wolfe et. al., JMB 285, p1917–1934 (1999), for the P53$^{zf}$ protein is CXGGACACGTX (SEQ ID NO: 15) where X indicates no clear sequence preference at that position. A library of EGFP reporter plasmids containing the partially randomized binding site CGGGA NNNNNG (SEQ ID NO: 16) was created (where N indicates a mixture of A, G, C, T) and introduced into host cells containing the α-Gal4 and Gal11p-P53$^{zf}$ fusion proteins. These cells were then grown to saturation at 37° C. in LB media with the appropriate antibiotics and then 100 µl of this culture was used to inoculate 10 ml of minimal media (as described in example 3) containing 10 ng/ml aTc and 100 µM IPTG. These cultures were then incubated for 24 hours at 30° C. on a rotating drum incubator. After incubation, one round of FACS sorting was performed on a Cytomation MoFlo multiple laser FACS sorter and individual EGFP positive clones were selected. Of 20 clones analyzed, 16 were EGFP positive (i.e. expressed at least 2 fold more EGFP than control cells). These 16 positive clones contained three unique P532$^{zf}$ binding sites. The most abundant of these sites matched the consensus from the vitro site selection.

In order to compare the in vivo interaction between the P53$^{zf}$ protein and each of the three selected sites, reporter plasmids containing each of the three selected sites was introduced into host cells containing either the Gal11p-P53$^{zf}$ fusion protein or the Gal11P-only control protein (i.e. Gal11P without an attached DBD). Dividing the mean EGFP fluorescence of the Gal11p-P53$^{zf}$ containing cells by the mean fluorescence of the otherwise identical Gal11p-only cells gives the fold-activation for each site reported in the figure. Four clones were also picked at random from the library and all of these clones had less than two-fold activation.

EQUIVALENTS

The present invention provides among other things novel methods and compositions for interaction trap assays. While specific embodiments of the subject invention have been discussed, the above specification is illustrative and not restrictive. Many variations of the invention will become apparent to those skilled in the art upon review of this specification. The appended claims are not intended to claim all such embodiments and variations, and the full scope of the invention should be determined by reference to the claim, along with its full scope of equivalents, and the specification, along with such variations.

All publications and patents mentioned herein, including those items listed below, are hereby incorporated by reference in their entirety as if each individual publication or patent was specifically and individually indicated to be incorporated by reference. In case of conflict, the present application, including any definitions herein, will control.

We claim:

1. A method for selecting a dimerizing polypeptide, comprising:
   providing a population of host cells wherein each host cell contains
   (a) a chimeric gene which encodes a fusion protein, including one or more zinc-finger DNA-binding domains, an activation domain that is heterologous to the DNA-binding domain, and a test polypeptide, wherein the chimeric gene is a member of a library comprising a plurality of randomly generated sequences test polypeptides;
   (b) a reporter gene operably linked to a transcriptional regulatory sequence which includes two or more binding sites (DBD recognition elements) for the DNA-binding domain of (a), wherein binding of a single copy of the fusion protein to the transcriptional regulatory sequence of the reporter gene does not result in a desired level of expression of the reporter gene;
   wherein dimerization of two copies of the fusion protein to each other and binding of the dimerized fusion protein to the transcriptional regulatory sequence of the reporter gene results in a desired level of expression of the reporter gene; and
   isolating host cells exhibiting a desired level of expression of the reporter gene thereby selecting a dimerizing polypeptide.

2. The method of claim 1, wherein the host cell further comprises a second reporter gene operably linked to a transcriptional regulatory sequence, the transcriptional regulatory sequence comprising at least one binding site for the DNA binding domain of the fusion protein.

3. The method of claim 1, further comprising isolating a polynucleotide comprising a sequence encoding the dimerizing polypeptide.

4. The method of claim 3, further comprising linking the sequence encoding the dimerizing polypeptide to a heterologous sequence.

5. The method of claim 1, wherein the host cell is a prokaryotic host cell.

6. The method claim 1, wherein the desired level of expression of the reporter gene confers a growth advantage on the host cell.

7. The method of claim 1, wherein the desired level of expression of the reporter gene produces a detectable signal.

8. The method of claim 1, wherein the library comprises at least $10^7$ members.

* * * * *

```
                         SEQUENCE LISTING

<160> NUMBER OF SEQ ID NOS: 97

<210> SEQ ID NO 1
<211> LENGTH: 25
<212> TYPE: PRT
<213> ORGANISM: Artificial Sequence
<220> FEATURE:
<223> OTHER INFORMATION: Description of Artificial Sequence:
      Illustrative conserved peptide sequence
<221> NAME/KEY: MOD_RES
<222> LOCATION: (2)..(5)
<223> OTHER INFORMATION: Variable amino acid; this Xaa range may
      encompass 2-4 variable amino acids
<221> NAME/KEY: MOD_RES
<222> LOCATION: (6)..(18)
<223> OTHER INFORMATION: Variable amino acid
<221> NAME/KEY: MOD_RES
<222> LOCATION: (20)..(24)
<223> OTHER INFORMATION: Variable amino acid; this Xaa range may
      encompass 3-5 variable amino acids

<400> SEQUENCE: 1

Cys Xaa Xaa Xaa Xaa Cys Xaa Xaa Xaa Xaa Xaa Xaa Xaa Xaa Xaa Xaa
 1               5                  10                  15

Xaa Xaa His Xaa Xaa Xaa Xaa Xaa His
            20                  25

<210> SEQ ID NO 2
<211> LENGTH: 38
<212> TYPE: DNA
<213> ORGANISM: Unknown Organism
<220> FEATURE:
<223> OTHER INFORMATION: Description of Unknown Organism: Lac promoter

<400> SEQUENCE: 2
ctttacactt tatgcttccg gctcgtatgt tgtgtcga                             38

<210> SEQ ID NO 3
<211> LENGTH: 39
<212> TYPE: DNA
<213> ORGANISM: Artificial Sequence
<220> FEATURE:
<223> OTHER INFORMATION: Description of Artificial Sequence: Hybrid
      promoter

<400> SEQUENCE: 3
ctttacaatt tatcccttgg tcggctagat ttactcgag                            39
```

```
<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence:
      Illustrative zinc finger peptide

<400> SEQUENCE: 4

Cys Cys His His
  1

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Linker

<400> SEQUENCE: 5

Ala Ala Ala Pro Arg Val Arg Thr Gly
  1               5

<210> SEQ ID NO 6
<211> LENGTH: 16
<212> TYPE: DNA
<213> ORGANISM: Escherichia coli

<400> SEQUENCE: 6
tcgacaagcg tgggcg                                                    16

<210> SEQ ID NO 7
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
caagggttca ggggcg                                                    16

<210> SEQ ID NO 8
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ggctataaaa ggggcg                                                    16

<210> SEQ ID NO 9
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
tgggacatgt tgggcg                                                    16
```

```
<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Zinc finger
      recognition sequence

<400> SEQUENCE: 10

Asn Ser Gly Ser Trp Lys
 1               5

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Zinc finger
      recognition sequence

<400> SEQUENCE: 11

Asn Ser Gly Ser His Lys
 1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Zinc finger
      recognition sequence

<400> SEQUENCE: 12

Asn His Gly Ser Trp Lys
 1               5

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Zinc finger
      recognition sequence

<400> SEQUENCE: 13

Thr Arg Thr Asn Lys Ser
 1               5

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: Zinc finger
      recognition sequence
<221> NAME/KEY: MOD_RES
<222> LOCATION: (2)
<223> OTHER INFORMATION: Positively charged amino acid
<221> NAME/KEY: MOD_RES
<222> LOCATION: (5)
<223> OTHER INFORMATION: Positively charged amino acid

<400> SEQUENCE: 14

Arg Xaa Trp Leu Xaa Leu
 1               5
```

```
<210> SEQ ID NO 15
<211> LENGTH: 11
<212> TYPE: DNA
<213> ORGANISM: Artificial Sequence
<220> FEATURE:
<223> OTHER INFORMATION: Description of Artificial Sequence: Consensus
      sequence
<221> NAME/KEY: modified_base
<222> LOCATION: (2)
<223> OTHER INFORMATION: No clear preference
<221> NAME/KEY: modified_base
<222> LOCATION: (11)
<223> OTHER INFORMATION: No clear preference

<400> SEQUENCE: 15
cnggacacgt n                                                          11

<210> SEQ ID NO 16
<211> LENGTH: 11
<212> TYPE: DNA
<213> ORGANISM: Artificial Sequence
<220> FEATURE:
<223> OTHER INFORMATION: Description of Artificial Sequence: In vivo
      site selection library
<221> NAME/KEY: modified_base
<222> LOCATION: (6)..(10)
<223> OTHER INFORMATION: A, T, C or G

<400> SEQUENCE: 16
cgggannnnn g                                                          11

<210> SEQ ID NO 17
<211> LENGTH: 11
<212> TYPE: DNA
<213> ORGANISM: Artificial Sequence
<220> FEATURE:
<223> OTHER INFORMATION: Description of Artificial Sequence:
      Illustrative nucleotide sequence

<400> SEQUENCE: 17
cgggacacgt g                                                          11

<210> SEQ ID NO 18
<211> LENGTH: 11
<212> TYPE: DNA
<213> ORGANISM: Artificial Sequence
<220> FEATURE:
<223> OTHER INFORMATION: Description of Artificial Sequence:
      Illustrative nucleotide sequence

<400> SEQUENCE: 18
cgggacatgt g                                                          11

<210> SEQ ID NO 19
<211> LENGTH: 11
<212> TYPE: DNA
<213> ORGANISM: Artificial Sequence
<220> FEATURE:
<223> OTHER INFORMATION: Description of Artificial Sequence:
      Illustrative nucleotide sequence

<400> SEQUENCE: 19
cgggacacgg g                                                          11

<210> SEQ ID NO 20
<211> LENGTH: 11
<212> TYPE: DNA
<213> ORGANISM: Artificial Sequence
```

```
<220> FEATURE:
<223> OTHER INFORMATION: Description of Artificial Sequence:
      Illustrative nucleotide sequence

<400> SEQUENCE: 20
cgggacacgt g                                                           11

<210> SEQ ID NO 21
<211> LENGTH: 11
<212> TYPE: DNA
<213> ORGANISM: Artificial Sequence
<220> FEATURE:
<223> OTHER INFORMATION: Description of Artificial Sequence:
      Illustrative nucleotide sequence

<400> SEQUENCE: 21
cgggacatgt g                                                           11

<210> SEQ ID NO 22
<211> LENGTH: 11
<212> TYPE: DNA
<213> ORGANISM: Artificial Sequence
<220> FEATURE:
<223> OTHER INFORMATION: Description of Artificial Sequence:
      Illustrative nucleotide sequence

<400> SEQUENCE: 22
cgggacacgg g                                                           11

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: Zinc finger
      recognition sequence

<400> SEQUENCE: 23

Gln Arg Gly Asn Leu Val
 1               5

<210> SEQ ID NO 24
<211> LENGTH: 6
<212> TYPE: PRT
<213> ORGANISM: Artificial Sequence
<220> FEATURE:
<223> OTHER INFORMATION: Description of Artificial Sequence: Zinc finger
      recognition sequence

<400> SEQUENCE: 24

Gln Lys Thr Asn Met Val
 1               5

<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence: Zinc finger
      recognition sequence

<400> SEQUENCE: 25

Gln Lys Tyr Asn Ile Leu
 1               5
```

```
<210> SEQ ID NO 26
<211> LENGTH: 6
<212> TYPE: PRT
<213> ORGANISM: Artificial Sequence
<220> FEATURE:
<223> OTHER INFORMATION: Description of Artificial Sequence: Zinc finger
      recognition sequence

<400> SEQUENCE: 26

Gln Arg Tyr Asn Val Val
  1               5

<210> SEQ ID NO 27
<211> LENGTH: 6
<212> TYPE: PRT
<213> ORGANISM: Artificial Sequence
<220> FEATURE:
<223> OTHER INFORMATION: Description of Artificial Sequence: Zinc finger
      recognition sequence

<400> SEQUENCE: 27

Gln Lys Gly Asn Met Val
  1               5

<210> SEQ ID NO 28
<211> LENGTH: 6
<212> TYPE: PRT
<213> ORGANISM: Artificial Sequence
<220> FEATURE:
<223> OTHER INFORMATION: Description of Artificial Sequence: Zinc finger
      recognition sequence

<400> SEQUENCE: 28

Gln Lys Gly Asn His Val
  1               5

<210> SEQ ID NO 29
<211> LENGTH: 6
<212> TYPE: PRT
<213> ORGANISM: Artificial Sequence
<220> FEATURE:
<223> OTHER INFORMATION: Description of Artificial Sequence: Zinc finger
      recognition sequence

<400> SEQUENCE: 29

Gln Lys Gly Asn Met Val
  1               5

<210> SEQ ID NO 30
<211> LENGTH: 6
<212> TYPE: PRT
<213> ORGANISM: Artificial Sequence
<220> FEATURE:
<223> OTHER INFORMATION: Description of Artificial Sequence: Zinc finger
      recognition sequence

<400> SEQUENCE: 30

Gln Arg Gly Asn Lys Val
  1               5

<210> SEQ ID NO 31
<211> LENGTH: 6
<212> TYPE: PRT
<213> ORGANISM: Artificial Sequence
<220> FEATURE:
<223> OTHER INFORMATION: Description of Artificial Sequence: Zinc finger
      recognition sequence
```

```
<400> SEQUENCE: 31

Gln Arg Gly Asn Lys Thr
 1               5

<210> SEQ ID NO 32
<211> LENGTH: 6
<212> TYPE: PRT
<213> ORGANISM: Artificial Sequence
<220> FEATURE:
<223> OTHER INFORMATION: Description of Artificial Sequence: Zinc finger
      recognition sequence

<400> SEQUENCE: 32

Gln Leu Gly Asn Met Val
 1               5

<210> SEQ ID NO 33
<211> LENGTH: 6
<212> TYPE: PRT
<213> ORGANISM: Artificial Sequence
<220> FEATURE:
<223> OTHER INFORMATION: Description of Artificial Sequence: Zinc finger
      recognition sequence

<400> SEQUENCE: 33

Gln Lys Gly Asn Lys Val
 1               5

<210> SEQ ID NO 34
<211> LENGTH: 6
<212> TYPE: PRT
<213> ORGANISM: Artificial Sequence
<220> FEATURE:
<223> OTHER INFORMATION: Description of Artificial Sequence: Zinc finger
      recognition sequence

<400> SEQUENCE: 34

Gln Leu Gly Asn Lys Val
 1               5

<210> SEQ ID NO 35
<211> LENGTH: 6
<212> TYPE: PRT
<213> ORGANISM: Artificial Sequence
<220> FEATURE:
<223> OTHER INFORMATION: Description of Artificial Sequence: Consensus
      sequence
<221> NAME/KEY: MOD_RES
<222> LOCATION: (5)
<223> OTHER INFORMATION: Variable amino acid

<400> SEQUENCE: 35

Asn Ser Gly Ala Xaa Asn
 1               5

<210> SEQ ID NO 36
<211> LENGTH: 6
<212> TYPE: PRT
<213> ORGANISM: Artificial Sequence
<220> FEATURE:
<223> OTHER INFORMATION: Description of Artificial Sequence: Zinc finger
      recognition sequence

<400> SEQUENCE: 36

Asn Ser Gly Ala Tyr Asn
 1               5
```

```
<210> SEQ ID NO 37
<211> LENGTH: 6
<212> TYPE: PRT
<213> ORGANISM: Artificial Sequence
<220> FEATURE:
<223> OTHER INFORMATION: Description of Artificial Sequence: Zinc finger
      recognition sequence

<400> SEQUENCE: 37

Asn Ser Gly Ala Trp Asn
 1               5

<210> SEQ ID NO 38
<211> LENGTH: 6
<212> TYPE: PRT
<213> ORGANISM: Artificial Sequence
<220> FEATURE:
<223> OTHER INFORMATION: Description of Artificial Sequence: Zinc finger
      recognition sequence

<400> SEQUENCE: 38

Asn Ser Gly Ala Phe Asn
 1               5

<210> SEQ ID NO 39
<211> LENGTH: 6
<212> TYPE: PRT
<213> ORGANISM: Artificial Sequence
<220> FEATURE:
<223> OTHER INFORMATION: Description of Artificial Sequence: Zinc finger
      recognition sequence

<400> SEQUENCE: 39

Asn Ser Gly Thr His Asn
 1               5

<210> SEQ ID NO 40
<211> LENGTH: 6
<212> TYPE: PRT
<213> ORGANISM: Artificial Sequence
<220> FEATURE:
<223> OTHER INFORMATION: Description of Artificial Sequence: Zinc finger
      recognition sequence

<400> SEQUENCE: 40

Asn Thr Gly Ala Tyr Asn
 1               5

<210> SEQ ID NO 41
<211> LENGTH: 6
<212> TYPE: PRT
<213> ORGANISM: Artificial Sequence
<220> FEATURE:
<223> OTHER INFORMATION: Description of Artificial Sequence: Zinc finger
      recognition sequence

<400> SEQUENCE: 41

Gly Ser Gly Ala Tyr Asn
 1               5

<210> SEQ ID NO 42
<211> LENGTH: 6
<212> TYPE: PRT
<213> ORGANISM: Artificial Sequence
<220> FEATURE:
<223> OTHER INFORMATION: Description of Artificial Sequence: Zinc finger
      recognition sequence
```

```
<400> SEQUENCE: 42

Gln Arg Gly Asn Lys Lys
 1               5

<210> SEQ ID NO 43
<211> LENGTH: 6
<212> TYPE: PRT
<213> ORGANISM: Artificial Sequence
<220> FEATURE:
<223> OTHER INFORMATION: Description of Artificial Sequence: Zinc finger
      recognition sequence

<400> SEQUENCE: 43

Gln Arg Gly Asn Val Lys
 1               5

<210> SEQ ID NO 44
<211> LENGTH: 6
<212> TYPE: PRT
<213> ORGANISM: Artificial Sequence
<220> FEATURE:
<223> OTHER INFORMATION: Description of Artificial Sequence: Zinc finger
      recognition sequence

<400> SEQUENCE: 44

Gln Lys His Asn Lys Lys
 1               5

<210> SEQ ID NO 45
<211> LENGTH: 6
<212> TYPE: PRT
<213> ORGANISM: Artificial Sequence
<220> FEATURE:
<223> OTHER INFORMATION: Description of Artificial Sequence: Zinc finger
      recognition sequence

<400> SEQUENCE: 45

Gln Lys Gly Asn Tyr Lys
 1               5

<210> SEQ ID NO 46
<211> LENGTH: 6
<212> TYPE: PRT
<213> ORGANISM: Artificial Sequence
<220> FEATURE:
<223> OTHER INFORMATION: Description of Artificial Sequence: Zinc finger
      recognition sequence

<400> SEQUENCE: 46

Gln Lys His Asn Lys Lys
 1               5

<210> SEQ ID NO 47
<211> LENGTH: 6
<212> TYPE: PRT
<213> ORGANISM: Artificial Sequence
<220> FEATURE:
<223> OTHER INFORMATION: Description of Artificial Sequence: Zinc finger
      recognition sequence

<400> SEQUENCE: 47

Gln Lys Gly Asn Ser Arg
 1               5
```

```
<210> SEQ ID NO 48
<211> LENGTH: 6
<212> TYPE: PRT
<213> ORGANISM: Artificial Sequence
<220> FEATURE:
<223> OTHER INFORMATION: Description of Artificial Sequence: Zinc finger
      recognition sequence

<400> SEQUENCE: 48

Gln Ser Gly Asn Lys Lys
 1               5

<210> SEQ ID NO 49
<211> LENGTH: 6
<212> TYPE: PRT
<213> ORGANISM: Artificial Sequence
<220> FEATURE:
<223> OTHER INFORMATION: Description of Artificial Sequence: Zinc finger
      recognition sequence

<400> SEQUENCE: 49

Gln Lys Ser Asn Leu Arg
 1               5

<210> SEQ ID NO 50
<211> LENGTH: 6
<212> TYPE: PRT
<213> ORGANISM: Artificial Sequence
<220> FEATURE:
<223> OTHER INFORMATION: Description of Artificial Sequence: Zinc finger
      recognition sequence

<400> SEQUENCE: 50

Gln Lys Ala Asn Thr Lys
 1               5

<210> SEQ ID NO 51
<211> LENGTH: 6
<212> TYPE: PRT
<213> ORGANISM: Artificial Sequence
<220> FEATURE:
<223> OTHER INFORMATION: Description of Artificial Sequence: Zinc finger
      recognition sequence

<400> SEQUENCE: 51

Gln Lys Ala Asn Lys Leu
 1               5

<210> SEQ ID NO 52
<211> LENGTH: 6
<212> TYPE: PRT
<213> ORGANISM: Artificial Sequence
<220> FEATURE:
<223> OTHER INFORMATION: Description of Artificial Sequence: Zinc finger
      recognition sequence

<400> SEQUENCE: 52

Gln Leu Ser Asn Lys Lys
 1               5

<210> SEQ ID NO 53
<211> LENGTH: 6
<212> TYPE: PRT
<213> ORGANISM: Artificial Sequence
<220> FEATURE:
<223> OTHER INFORMATION: Description of Artificial Sequence: Zinc finger
      recognition sequence
```

```
<400> SEQUENCE: 53

Gln Pro Gly Asn Lys Lys
  1               5

<210> SEQ ID NO 54
<211> LENGTH: 6
<212> TYPE: PRT
<213> ORGANISM: Artificial Sequence
<220> FEATURE:
<223> OTHER INFORMATION: Description of Artificial Sequence: Zinc finger
      recognition sequence

<400> SEQUENCE: 54

Gln Lys Gly Asn Asn Val
  1               5

<210> SEQ ID NO 55
<211> LENGTH: 6
<212> TYPE: PRT
<213> ORGANISM: Artificial Sequence
<220> FEATURE:
<223> OTHER INFORMATION: Description of Artificial Sequence: Zinc finger
      recognition sequence

<400> SEQUENCE: 55

Gln Lys Ser Asn Asn Val
  1               5

<210> SEQ ID NO 56
<211> LENGTH: 6
<212> TYPE: PRT
<213> ORGANISM: Artificial Sequence
<220> FEATURE:
<223> OTHER INFORMATION: Description of Artificial Sequence: Zinc finger
      recognition sequence

<400> SEQUENCE: 56

Gln Lys His Asn Leu Arg
  1               5

<210> SEQ ID NO 57
<211> LENGTH: 6
<212> TYPE: PRT
<213> ORGANISM: Artificial Sequence
<220> FEATURE:
<223> OTHER INFORMATION: Description of Artificial Sequence: Zinc finger
      recognition sequence

<400> SEQUENCE: 57

His Lys His His Lys Ala
  1               5

<210> SEQ ID NO 58
<211> LENGTH: 6
<212> TYPE: PRT
<213> ORGANISM: Artificial Sequence
<220> FEATURE:
<223> OTHER INFORMATION: Description of Artificial Sequence: Zinc finger
      recognition sequence

<400> SEQUENCE: 58

His Leu His His Lys Ala
  1               5
```

```
<210> SEQ ID NO 59
<211> LENGTH: 6
<212> TYPE: PRT
<213> ORGANISM: Artificial Sequence
<220> FEATURE:
<223> OTHER INFORMATION: Description of Artificial Sequence: Zinc finger
      recognition sequence

<400> SEQUENCE: 59

Gln Arg Trp Leu Asn Arg
 1               5

<210> SEQ ID NO 60
<211> LENGTH: 6
<212> TYPE: PRT
<213> ORGANISM: Artificial Sequence
<220> FEATURE:
<223> OTHER INFORMATION: Description of Artificial Sequence: Zinc finger
      recognition sequence

<400> SEQUENCE: 60

Gln Arg Trp Leu Arg Arg
 1               5

<210> SEQ ID NO 61
<211> LENGTH: 6
<212> TYPE: PRT
<213> ORGANISM: Artificial Sequence
<220> FEATURE:
<223> OTHER INFORMATION: Description of Artificial Sequence: Zinc finger
      recognition sequence

<400> SEQUENCE: 61

Gln Asp Trp Leu Asn Arg
 1               5

<210> SEQ ID NO 62
<211> LENGTH: 6
<212> TYPE: PRT
<213> ORGANISM: Artificial Sequence
<220> FEATURE:
<223> OTHER INFORMATION: Description of Artificial Sequence: Zinc finger
      recognition sequence

<400> SEQUENCE: 62

Tyr Lys Arg Asp Asn Arg
 1               5

<210> SEQ ID NO 63
<211> LENGTH: 6
<212> TYPE: PRT
<213> ORGANISM: Artificial Sequence
<220> FEATURE:
<223> OTHER INFORMATION: Description of Artificial Sequence: Zinc finger
      recognition sequence

<400> SEQUENCE: 63

Trp Arg Ser Ser Leu Val
 1               5

<210> SEQ ID NO 64
<211> LENGTH: 6
<212> TYPE: PRT
<213> ORGANISM: Artificial Sequence
<220> FEATURE:
<223> OTHER INFORMATION: Description of Artificial Sequence: Zinc finger
      recognition sequence
```

```
<400> SEQUENCE: 64

Trp Gln Ser Ser Lys Val
 1               5

<210> SEQ ID NO 65
<211> LENGTH: 6
<212> TYPE: PRT
<213> ORGANISM: Artificial Sequence
<220> FEATURE:
<223> OTHER INFORMATION: Description of Artificial Sequence: Zinc finger
      recognition sequence

<400> SEQUENCE: 65

Trp Tyr Ser Ser Ile Val
 1               5

<210> SEQ ID NO 66
<211> LENGTH: 6
<212> TYPE: PRT
<213> ORGANISM: Artificial Sequence
<220> FEATURE:
<223> OTHER INFORMATION: Description of Artificial Sequence: Zinc finger
      recognition sequence

<400> SEQUENCE: 66

Phe Asp Ser Ser Arg Ala
 1               5

<210> SEQ ID NO 67
<211> LENGTH: 6
<212> TYPE: PRT
<213> ORGANISM: Artificial Sequence
<220> FEATURE:
<223> OTHER INFORMATION: Description of Artificial Sequence: Zinc finger
      recognition sequence

<400> SEQUENCE: 67

Ala Arg Trp Leu Asn Arg
 1               5

<210> SEQ ID NO 68
<211> LENGTH: 6
<212> TYPE: PRT
<213> ORGANISM: Artificial Sequence
<220> FEATURE:
<223> OTHER INFORMATION: Description of Artificial Sequence: Zinc finger
      recognition sequence

<400> SEQUENCE: 68

Glu Arg Trp Arg Asn Arg
 1               5

<210> SEQ ID NO 69
<211> LENGTH: 6
<212> TYPE: PRT
<213> ORGANISM: Artificial Sequence
<220> FEATURE:
<223> OTHER INFORMATION: Description of Artificial Sequence: Zinc finger
      recognition sequence

<400> SEQUENCE: 69

Glu Arg Trp Arg Arg Arg
 1               5
```

```
<210> SEQ ID NO 70
<211> LENGTH: 6
<212> TYPE: PRT
<213> ORGANISM: Artificial Sequence
<220> FEATURE:
<223> OTHER INFORMATION: Description of Artificial Sequence: Zinc finger
      recognition sequence

<400> SEQUENCE: 70

Glu Lys Trp Arg Arg Arg
 1               5

<210> SEQ ID NO 71
<211> LENGTH: 6
<212> TYPE: PRT
<213> ORGANISM: Artificial Sequence
<220> FEATURE:
<223> OTHER INFORMATION: Description of Artificial Sequence: Zinc finger
      recognition sequence

<400> SEQUENCE: 71

Glu Gly Trp Arg Arg Arg
 1               5

<210> SEQ ID NO 72
<211> LENGTH: 6
<212> TYPE: PRT
<213> ORGANISM: Artificial Sequence
<220> FEATURE:
<223> OTHER INFORMATION: Description of Artificial Sequence: Zinc finger
      recognition sequence

<400> SEQUENCE: 72

Glu Arg Trp Arg Lys Arg
 1               5

<210> SEQ ID NO 73
<211> LENGTH: 6
<212> TYPE: PRT
<213> ORGANISM: Artificial Sequence
<220> FEATURE:
<223> OTHER INFORMATION: Description of Artificial Sequence: Zinc finger
      recognition sequence

<400> SEQUENCE: 73

Glu Arg Trp Arg Asn Arg
 1               5

<210> SEQ ID NO 74
<211> LENGTH: 6
<212> TYPE: PRT
<213> ORGANISM: Artificial Sequence
<220> FEATURE:
<223> OTHER INFORMATION: Description of Artificial Sequence: Zinc finger
      recognition sequence

<400> SEQUENCE: 74

Glu Arg Trp Arg Ile Arg
 1               5

<210> SEQ ID NO 75
<211> LENGTH: 6
<212> TYPE: PRT
<213> ORGANISM: Artificial Sequence
<220> FEATURE:
<223> OTHER INFORMATION: Description of Artificial Sequence: Zinc finger
      recognition sequence
```

```
<400> SEQUENCE: 75

Glu Arg Trp Arg Ser Arg
 1               5

<210> SEQ ID NO 76
<211> LENGTH: 6
<212> TYPE: PRT
<213> ORGANISM: Artificial Sequence
<220> FEATURE:
<223> OTHER INFORMATION: Description of Artificial Sequence: Zinc finger
      recognition sequence

<400> SEQUENCE: 76

Glu Arg Trp Arg Val Arg
 1               5

<210> SEQ ID NO 77
<211> LENGTH: 6
<212> TYPE: PRT
<213> ORGANISM: Artificial Sequence
<220> FEATURE:
<223> OTHER INFORMATION: Description of Artificial Sequence: Zinc finger
      recognition sequence

<400> SEQUENCE: 77

Glu Arg Trp Arg Leu Arg
 1               5

<210> SEQ ID NO 78
<211> LENGTH: 6
<212> TYPE: PRT
<213> ORGANISM: Artificial Sequence
<220> FEATURE:
<223> OTHER INFORMATION: Description of Artificial Sequence: Zinc finger
      recognition sequence

<400> SEQUENCE: 78

Glu Lys Trp Arg Thr Arg
 1               5

<210> SEQ ID NO 79
<211> LENGTH: 6
<212> TYPE: PRT
<213> ORGANISM: Artificial Sequence
<220> FEATURE:
<223> OTHER INFORMATION: Description of Artificial Sequence: Zinc finger
      recognition sequence

<400> SEQUENCE: 79

Glu Asn Trp Arg Lys Arg
 1               5

<210> SEQ ID NO 80
<211> LENGTH: 6
<212> TYPE: PRT
<213> ORGANISM: Artificial Sequence
<220> FEATURE:
<223> OTHER INFORMATION: Description of Artificial Sequence: Zinc finger
      recognition sequence

<400> SEQUENCE: 80

Glu Gln Trp Arg Lys Arg
 1               5
```

-continued

```
<210> SEQ ID NO 81
<211> LENGTH: 6
<212> TYPE: PRT
<213> ORGANISM: Artificial Sequence
<220> FEATURE:
<223> OTHER INFORMATION: Description of Artificial Sequence: Zinc finger
      recognition sequence

<400> SEQUENCE: 81

Glu Arg Trp Arg Met Arg
 1               5

<210> SEQ ID NO 82
<211> LENGTH: 6
<212> TYPE: PRT
<213> ORGANISM: Artificial Sequence
<220> FEATURE:
<223> OTHER INFORMATION: Description of Artificial Sequence: Consensus
      sequence
<221> NAME/KEY: MOD_RES
<222> LOCATION: (2)
<223> OTHER INFORMATION: Variable amino acid
<221> NAME/KEY: MOD_RES
<222> LOCATION: (5)
<223> OTHER INFORMATION: Variable amino acid

<400> SEQUENCE: 82

Thr Xaa Thr Asn Xaa Ser
 1               5

<210> SEQ ID NO 83
<211> LENGTH: 6
<212> TYPE: PRT
<213> ORGANISM: Artificial Sequence
<220> FEATURE:
<223> OTHER INFORMATION: Description of Artificial Sequence: Zinc finger
      recognition sequence

<400> SEQUENCE: 83

Arg Arg Trp Leu Lys Leu
 1               5

<210> SEQ ID NO 84
<211> LENGTH: 6
<212> TYPE: PRT
<213> ORGANISM: Artificial Sequence
<220> FEATURE:
<223> OTHER INFORMATION: Description of Artificial Sequence: Zinc finger
      recognition sequence

<400> SEQUENCE: 84

Arg Lys Trp Leu Lys Leu
 1               5

<210> SEQ ID NO 85
<211> LENGTH: 6
<212> TYPE: PRT
<213> ORGANISM: Artificial Sequence
<220> FEATURE:
<223> OTHER INFORMATION: Description of Artificial Sequence: Zinc finger
      recognition sequence

<400> SEQUENCE: 85

Arg Lys Trp Leu Gln Leu
 1               5
```

```
<210> SEQ ID NO 86
<211> LENGTH: 6
<212> TYPE: PRT
<213> ORGANISM: Artificial Sequence
<220> FEATURE:
<223> OTHER INFORMATION: Description of Artificial Sequence: Zinc finger
      recognition sequence

<400> SEQUENCE: 86

Arg Lys Trp Leu Arg Leu
 1               5

<210> SEQ ID NO 87
<211> LENGTH: 6
<212> TYPE: PRT
<213> ORGANISM: Artificial Sequence
<220> FEATURE:
<223> OTHER INFORMATION: Description of Artificial Sequence: Zinc finger
      recognition sequence

<400> SEQUENCE: 87

Arg Lys Trp Leu Met Leu
 1               5

<210> SEQ ID NO 88
<211> LENGTH: 6
<212> TYPE: PRT
<213> ORGANISM: Artificial Sequence
<220> FEATURE:
<223> OTHER INFORMATION: Description of Artificial Sequence: Zinc finger
      recognition sequence

<400> SEQUENCE: 88

Arg Lys Trp Ile Asn Leu
 1               5

<210> SEQ ID NO 89
<211> LENGTH: 6
<212> TYPE: PRT
<213> ORGANISM: Artificial Sequence
<220> FEATURE:
<223> OTHER INFORMATION: Description of Artificial Sequence: Zinc finger
      recognition sequence

<400> SEQUENCE: 89

Arg Lys Trp Tyr Gln Leu
 1               5

<210> SEQ ID NO 90
<211> LENGTH: 6
<212> TYPE: PRT
<213> ORGANISM: Artificial Sequence
<220> FEATURE:
<223> OTHER INFORMATION: Description of Artificial Sequence: Zinc finger
      recognition sequence

<400> SEQUENCE: 90

Arg Ala Trp Leu Lys Leu
 1               5

<210> SEQ ID NO 91
<211> LENGTH: 6
<212> TYPE: PRT
<213> ORGANISM: Artificial Sequence
<220> FEATURE:
<223> OTHER INFORMATION: Description of Artificial Sequence: Zinc finger
      recognition sequence
```

```
<400> SEQUENCE: 91

Lys Lys Trp Tyr Arg Leu
  1               5

<210> SEQ ID NO 92
<211> LENGTH: 9
<212> TYPE: DNA
<213> ORGANISM: Artificial Sequence
<220> FEATURE:
<223> OTHER INFORMATION: Description of Artificial Sequence:
      Illustrative nucleotide sequence
<221> NAME/KEY: modified_base
<222> LOCATION: (4)..(9)
<223> OTHER INFORMATION: A, T, C or G

<400> SEQUENCE: 92 gcgnnnnnn                                                                  9

<210> SEQ ID NO 93
<211> LENGTH: 6
<212> TYPE: DNA
<213> ORGANISM: Artificial Sequence
<220> FEATURE:
<223> OTHER INFORMATION: Description of Artificial Sequence:
      Illustrative nucleotide sequence

<400> SEQUENCE: 93 tgggcg                                                                     6

<210> SEQ ID NO 94
<211> LENGTH: 12
<212> TYPE: DNA
<213> ORGANISM: Artificial Sequence
<220> FEATURE:
<223> OTHER INFORMATION: Description of Artificial Sequence:
      Illustrative nucleotide sequence

<400> SEQUENCE: 94
aaagtttggg cg                                                             12

<210> SEQ ID NO 95
<211> LENGTH: 89
<212> TYPE: PRT
<213> ORGANISM: Artificial Sequence
<220> FEATURE:
<223> OTHER INFORMATION: Description of Artificial Sequence:
      Illustrative peptide sequence
<221> NAME/KEY: MOD_RES
<222> LOCATION: (60)..(89)
<223> OTHER INFORMATION: Variable amino acid

<400> SEQUENCE: 95

Met Glu Arg Pro Tyr Ala Cys Pro Val Glu Ser Cys Asp Arg Arg Phe
  1               5                  10                  15

Ser Arg Ser Asp Glu Leu Thr Arg His Ile Arg Ile His Thr Gly Gln
                 20                  25                  30

Lys Pro Phe Gln Cys Arg Ile Cys Met Arg Asn Phe Ser Arg Ser Asp
             35                  40                  45

His Leu thr thr His Ile Arg Thr His Thr Gly Xaa Xaa Xaa Xaa Xaa
         50                  55                  60

Xaa Xaa Xaa Xaa Xaa Xaa Xaa Xaa Xaa Xaa Xaa Xaa Xaa Xaa Xaa Xaa
 65                  70                  75                  80

Xaa Xaa Xaa Xaa Xaa Xaa Xaa Xaa Xaa
                 85
```

```
-continued

<210> SEQ ID NO 96
<211> LENGTH: 12
<212> TYPE: DNA
<213> ORGANISM: Artificial Sequence
<220> FEATURE:
<223> OTHER INFORMATION: Description of Artificial Sequence:
      Illustrative nucleotide sequence

<400> SEQUENCE: 96
tatatatggg cg                                                              12

<210> SEQ ID NO 97
<211> LENGTH: 12
<212> TYPE: DNA
<213> ORGANISM: Artificial Sequence
<220> FEATURE:
<223> OTHER INFORMATION: Description of Artificial Sequence:
      Illustrative nucleotide sequence

<400> SEQUENCE: 97
gcgcgctggg cg                                                              12
```